US007932030B2

(12) United States Patent
Hollenbach et al.

(10) Patent No.: US 7,932,030 B2

(45) Date of Patent: Apr. 26, 2011

(54) SYSTEM FOR PULLING OUT REGULATORY ELEMENTS USING YEAST

(75) Inventors: Andrew D. Hollenbach, New Orleans, LA (US); Kelly E. Johanson, New Orleans, LA (US)

(73) Assignee: The Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 636 days.

(21) Appl. No.: 11/697,113

(22) Filed: Apr. 5, 2007

(65) Prior Publication Data

US 2008/0248467 A1 Oct. 9, 2008

(51) Int. Cl.

*C12Q 1/68* (2006.01)
*C12N 15/63* (2006.01)
*C12N 1/19* (2006.01)

(52) U.S. Cl. ........................................ 435/6; 435/320.1

(58) Field of Classification Search ........................ None
See application file for complete search history.

(56) References Cited

U.S. PATENT DOCUMENTS

| | | | | |
|---|---|---|---|---|
| 5,024,941 | A * | 6/1991 | Maine et al. | 435/69.9 |
| 5,955,280 | A | 9/1999 | Vidal et al. | |
| 6,664,048 | B1 | 12/2003 | Wanker et al. | |
| 6,709,861 | B2 | 3/2004 | Mead et al. | |
| 7,153,665 | B2 | 12/2006 | Ferrick et al. | |
| 2003/0044787 | A1 | 3/2003 | Joung | |
| 2004/0244065 | A1 * | 12/2004 | Mead et al. | 800/8 |

OTHER PUBLICATIONS

Meijer et al. Vectors for transcription factor cloning and target site identification by means of genetic selection in yeast. Yeast. Nov. 1998;14(15):1407-15.*

Bonneaud et al. A family of low and high copy replicative, integrative and single-stranded *S. cerevisiae/E. coli* shuttle vectors. Yeast. Aug.-Sep. 1991;7(6):609-15.*

Fields, S. & Song, O. A novel genetic system to detect protein-protein interactions. Nature. 340(6230), 245-46 (1989).

Li, J.J. & Herskowitz, I. Isolation of ORC6, a component of the yeast origin recognition complex by a one-hybrid system. Science. 262(5141), 1870-74 (1993).

Orlando, V., Strutt, H., & Paro, R. Analysis of chromatin structure by in vivo formaldehyde cross-linking. Methods. 11 (2), 205-14 (1997).

Wei, C.L., Wu, Q., Vega, V.B., Chiu, K.P., Ng, P., Zhang, T., Shabab, A., Yong H.C., Fu, Y., Weng, Z., Liu, J., Zhao, X.D., Chew, J.L., Lee., Y.L., Kuznetzov, V.A., Sung, W.K., Miller, L.D., Lim, B., Liu, E.T., Yu, Q., Ng, H.H., & Ruan, Y. A global map of p53 transcription-factor binding sites in the human genome. Cell. 124(1), 207-19 (2006).

Ren, B., Robert, F., Wyrick, J.J., Aparicio, O., Jennings, E.G., Simon, I., Zeitlinger, J., Schreiber, J., Hannett, N., Kanin, E., Volkert, T.L., Wilson, C.J., Bell, S.P., & Young, R.A. Genome-Wide Location and Function of DNA Binding Proteins. Science. 290(5500), 2306-09 (2000).

Mastick, G.S., McKay, R., Oligino, T., Donovan, K. & Lopez, A.J. Identification of target genes regulated by homeotic proteins in Drosophila melanogaster through genetic selection of Ultrabithorax protein-binding sites in yeast. Genetics. 139, 349-63 (1995).

Ausubel, F.M., Brent, R., Kingston, R.E., Moore, D.D., Seidman, J.G., Smith, J.A. & Struhl, K. Current protocols in molecular biology, (John Wiley & Sons, Boston, MA, 1996).

Margue, C.M., Bernasconi, M., Barr, F.G., & Schafer, B.W. Transcriptional modulation of the anti-apoptotic protein BCL-XL by the paired box transcription factors PAX3 and PAX3/FKHR. Oncogene. 19(25), 2921-29 (2000).

Epstein, J.A., Shapiro, D.N., Cheng, J., Lam, P.Y. & Maas, R.L. Pax3 modulates expression of the c-Met receptor during limb muscle development. Proceedings of the National Academy of Sciences of the United States of America. 93, 4213-4218 (1996).

Galibert, M.D., Yavuzer, U., Dexter, T.J. & Goding, C.R. Pax3 and regulation of the melanocyte-specific tyrosinase-related protein-1 promoter. Journal of Biological Chemistry. 274, 26894-900 (1999).

Epstein, J., Cai, J., Glaser, T., Jepeal, L. & Maas, R. Identification of a Pax paired domain recognition sequence and evidence for DNA-dependent conformational changes. Journal of Biological Chemistry. 269, 8355-61 (1994).

Bouvet, P. Determination of nucleic acid recognition sequences by SELEX. Methods in Molecular Biology. 148, 603-10 (2001).

Vasyutina, E., Stebler, J., Brand-Saberi, B., Schulz, S., Raz, E. & Birchmeier, C. CXCR4 and Gab1 cooperate to control the development of migrating muscle progenitor cells. Genes & Development. 19, 2187-98 (2005).

Mood, K., Saucier, C., Bong, Y.S., Lee, H.S., Park, M. & Daar, I.O. Gab1 is required for cell cycle transition, cell proliferation, and transformation induced by an oncogenic met receptor. Molecular and Cellular Biology. 17, 3717-28 (2006).

Fan, S., Ma, Y.X., Gao, M., Yuan, R.Q., Meng, Q., Goldberg, I.D. & Rosen, E.M. The multisubstrate adapter Gab1 regulates hepatocyte growth factor (scatter factor)-c-Met signaling for cell survival and DNA repair. Molecular and Cellular Biology. 21, 4968-84 (2001).

Wilson T E et al: "Identification of the DNA Binding Site for NGFI-B by Genetic Selection in Yeast" Science, American Association for the Advancement of Science, US, Washington, DC, vol. 252, May 31, 1991, pp. 1296-1300, XP002061509 ISSN: 0036-8075.

Ostrowski Jerzy et al: "Heterogeneous nuclear ribonucleoprotein K protein associates with multiple mitochondrial transcripts within the organelle" Journal of Biological Chemistry, vol. 277, No. 8, Feb. 22, 2002, pp. 6303-6310, XP002496345 ISSN: 0021-9258.

Sengupta et al: "Identification of RNAs that bind to a specific protein using the yeast three-hybrid system" RNA, Cold Spring Harbor Laboratory Press, Woodbury, NY, US vol. 5, Jan. 1, 1999, pp. 596-601, XP002985922 ISSN: 1355-8382 abstract.

(Continued)

*Primary Examiner* — Michele K Joike

(74) *Attorney, Agent, or Firm* — Jason P. Mueller; Adams and Reese LLP

(57) ABSTRACT

Disclosed are methods for identifying molecular interactions between DNA sequences and proteins in vivo. The methods of the invention employ known or suspected DNA-binding proteins and genomic DNA in a plasmid library. Interacting molecules direct the expression of a reporter gene, the expression of which is then assayed. Also disclosed are genetic constructs useful in practicing the methods of the invention.

3 Claims, 10 Drawing Sheets

OTHER PUBLICATIONS

Park Kyoungsook et al: "A split enhanced green fluorescent protein-based reporter in yeast two-hybrid system." The Protein Journal Feb. 2007, vol. 26, No. 2, Feb. 2007, pp. 107-116, XP002496347 ISSN: 1572-3887 abstract.

Lee et al: "Foxd3 mediates zebrafish myf5 expression during early somitogenesis" Developmental Biology, Academic Press, New York, NY, US, vol. 290, No. 2 Feb. 15, 2006, pp. 359-372, XP005265888 ISSN: 0012-1606.

Hollenbach Andrew D et al: "The Pax3-FKHR oncoprotein is unresponsive to the Pax3-associated repressor hDaxx" EMBO (European Molecular Biology Organziation) Journal, vol. 18, No. 13, Jul. 1, 1999, pp. 3702-3711, XP002496379 ISSN: 0261-4189.

Zeng Jue et al: "Genome wide screens in yeast to identify potential binding sites and target genes of DNA-binding proteins" Nucleic Acids Research, vol. 36, No. 1, Jan. 2008, page Article No.: e8, XP002496348 ISSN: 0305-1048.

* cited by examiner

SYSTEM FOR PULLING OUT REGULATORY ELEMENTS USING YEAST

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON COMPACT DISC

The Sequence Listing, which is a part of the present disclosure and is submitted in conformity with 37 CFR §§1.821-1.825, includes a computer readable form and a written sequence listing comprising nucleotide and/or amino acid sequences of the present invention. The sequence listing information recorded in computer readable form (created: 3 Apr. 2007; filename: Sequence_Listing_Yeast_PORE_ST25; size: 54.3 KB) is identical to the written sequence listing. No new matter has been introduced. The subject matter of the Sequence Listing is incorporated herein by reference in its entirety.

BACKGROUND OF THE INVENTION

1. Field of the Invention

The present invention relates to processes of using microorganisms to measure or test interaction between nucleic acids and protein. The present invention more specifically relates to an improved method for the in vivo identification and optional characterization of genomic DNA sequences that interact with DNA-binding proteins. The present invention further relates to a kit useful for carrying out the method of the invention. The present invention further provides vectors and vector components configured for expression of fusion proteins in yeast and bacteria, or for cloning of genomic DNA. The present invention also provides vectors and vector components that allow inserted nucleic acid sequences that are deleterious to a host cell to be cloned successfully.

2. Description of Related Art

Numerous biologically important functions involve transient interactions between DNA molecules and proteins, RNA molecules and proteins, two or more proteins or RNA molecules, or ligands and receptors. Recognition and binding of sequence-specific DNA-binding proteins (e.g., transcription factors) to regulatory elements within the genome—which often lie outside the regions of the genome that are contained within cDNA libraries—is a critical component of the spatio-temporal control of gene expression, directing epigenetic controls important for proper cellular function in all organisms. Conservation of these control mechanisms ensures proper replication and cell division. Conversely, their alteration (e.g., modifications causing changes in the expression or binding capacity of transcription factors) is often implicated in a cell's transition to a malignant state.

For example, alveolar rhabdomyosarcoma (ARMS) is a form of cancer characterized by a t(2;13)(q35;q14) chromosomal translocation that results in the fusion of two myogenic transcription factors: Pax3 and FKHR (FOX01a). The term "transcription factor" describes any protein required to initiate or regulate DNA transcription in eukaryotes. ARMS is an aggressive solid muscle tumor occurring predominantly in children. It has a poor prognosis, and an approximate event-free four-year survival rate of only 17%. Despite the identification and characterization of the oncogenic fusion protein Pax3-FKHR, little is known about the genes directly regulated by Pax3 or FKHR, or how their expression may be altered by the Pax3-FKHR fusion protein.

While many techniques exist to investigate the possible gene targets and binding specificities of different transcription factors, they either are too labor-intensive to be useful in a genomic screen, fail to use and cannot be adapted to use genomic DNA, or are subject to such levels of inherent inefficiency as to be inadequate.

Many genes of higher eukaryotes are transcribed into mRNA only in specific cell-types. For example, reticulocytes (immature red blood cells) contain mRNA for hemoglobin—the iron-containing oxygen-transport metalloprotein in red blood cells—while nerve cells do not. The particular DNA sequences that encode the mRNA in a cell can be cloned by using retroviral reverse transcriptase to make DNA copies of the mRNA (the copies are called "complimentary DNA," or cDNA clones) isolated from the cell. These single-stranded cDNA clones are converted into double-stranded DNAs and cloned into plasmid vectors, creating a cDNA library for that particular cell-type. cDNA libraries contain only sequences expressed as mRNA in the particular cell-type used to generate the library, but they lack the intronic (intragenic), non-coding sequences of genomic DNA, which were spliced out of the transcribed RNA seqeunces by posttranscriptional modification. cDNA libraries also contain 5' and 3' untranslated regions (5'-UTR and 3'-UTR), which are non-coding nucleotide regions at either end of each mRNA molecule, and derive from DNA adjacent to the gene. The 5'- and 3'-UTRs may contain protein binding sites, and can be involved in regulating expression of the adjacent gene.

In many eukaryotes, a large percentage of the total genome is comprised of non-coding DNA that does not lie near any gene. It is also clear, however, that gene transcription is often stimulated by DNA regions called "enhancers," which contain protein binding sites and may be located in non-coding regions tens of thousands of base pairs upstream or downstream from the transcriptional start site. Many mammalian genes are regulated by more than one enhancer region, and their identification and characterization represents a difficult problem. While a cDNA library can help identify the chromosomal location of a gene, it cannot reveal the locations of enhancers. A cDNA library is also of limited use in identifying promoter-proximal elements, which are non-coding regions that lie much closer to transcriptional start sites (e.g., 100-200 base pairs upstream) and also provide protein binding sites, but which are not contained within mRNA, and so are not contained in cDNA libraries. Still, the relative proximity of promoter elements makes them easier to find than enhancers. Because enhancer and promoter elements are so fundamental to the regulation of transcription, and because the dysregulation of transcription can lead to disease, methods of identifying and characterizing enhancer and promoter have generated tremendous interest.

Study of DNA outside the immediate vicinity of genes—outside the regions covered by cDNA libraries—necessitates the use of genomic DNA libraries. Genomic DNA is all the DNA sequences comprising the genome (the total genetic information carried) of a cell or organism, and a genomic DNA library is a collection of clones that contains the entire genome Like cDNA libraries, genomic DNA libraries are often contained within plasmid vectors. However, genomic DNA libraries are derived directly from genomic DNA, not mRNA, and so contain non-coding DNA (including introns) as well as coding DNA (exons). Creating genomic DNA libraries is difficult, however, because of the relatively low efficiency of *E. coli* transformation and the number of colonies that can be grown on a culture plate. A genomic DNA library must contain a sufficient number of independently-derived clones that the probability is high (≧95%) that every DNA sequence of the organism is contained within the library. The difficulty of creating such libraries is compounded by the effects of some cloned genomic DNA fragments, which may contain promoter or enhancer elements, sequences that encode toxic peptides, or other unstable elements. For example, a clone containing a promoter or enhancer may drive transcription into the plasmid vector, thus interfering with the vector's replication or expression of drug resistance. The resulting library would lack genomic DNA clones bearing those sequences because bacteria bearing those clones would die, yet those are some of the very sequences that are the object of study by the methods of this invention.

Mutation of either a DNA-binding protein or a genomic regulatory element may disrupt their ability to interact, thereby producing dire consequences by altering the biological processes under their control. Such mutations can form the basis of congenital diseases, or of certain cancers. While many DNA-binding proteins and the nucleic acid sequences they recognize have been identified, there remains a need for improved methods to investigate and identify the manner in which they interact, the genomic contexts of these sequences, the downstream genes they in turn control, the biological processes they regulate.

Therefore, identifying the regulatory elements in a genomic DNA context is critical not only for understanding their role in normal biological activities but in determining the underlying molecular mechanisms that contribute to genetic disorders and the diseased state.

Classical methods for identifying interactions between nucleic acids and proteins—e.g., co-immunoprecipitation, cross-linking, or gel-shift mobility assay—are not available for all proteins, and may not be sufficiently sensitive. Furthermore, these methods are difficult, time-consuming, involve hazardous materials, and are not amenable to screening large populations of potentially interacting partners. The yeast two-hybrid (Y2H) system (Fields and Song 1989; see also U.S. Pat. No. 5,955,280) represented a ground-breaking development in the identification of novel protein-protein interactions, and points the way to methods for identifying interactions between nucleic acids and proteins.

The Y2H system allows rapid demonstration of in vivo interactions between proteins, along with easy isolation of the nucleic acid sequences that encode the interacting proteins. The Y2H system exploits one of the features shared by many eukaryotic transcription factors that carry two separable, functional domains: a first domain serves to recognize and bind to specific DNA sequences (the DNA binding domain, or "DB"); and a second domain activates the RNA-polymerase complex (the activation domain, or "AD"). In a typical Y2H screening paradigm, a "bait" protein is expressed in yeast cells as a fusion protein comprising a DNA binding domain (e.g., the GAL4 DB) and a protein of interest ("X"). Concurrently, the same yeast cell expresses a "fish" protein as a fusion protein comprising an activation domain (e.g., the GAL4 AD) and another protein of interest ("Y"). Any interaction between the X and Y moieties of the bait and fish fusion proteins, respectively, also brings the DNA binding and activation domains of the fusion proteins into close proximity. The result is a protein complex comprising X, Y, a DNA binding domain, and an activation domain. The DNA binding domain of the complex binds a cognate DNA sequence, while the activation domain of that complex triggers expression of a reporter gene (e.g., HIS3 or lacZ).

Expression of the reporter gene allows identification and selection of yeast cells containing interacting proteins X and Y. For example, by culturing yeast that are auxotrophic for histidine on media lacking histidine, only yeast cells bearing interacting X and Y proteins will grow and form colonies because only those cells will express histidine. Such colonies can be identified visually on solid media, isolated, and subjected to further analysis. For example, the genetic sequence corresponding to protein X may be determined by isolating the corresponding plasmid DNA and subjecting it to sequence analysis.

Many variants of the Y2H system exist (see, e.g., U.S. Pat. No. 5,955,280). For example, a "reverse two-hybrid" (R2H) system permits identification of interaction between proteins (just as with the traditional Y2H system), but through counterselection techniques also allows testing of the relative strength of that interaction. For example, expression of the URA3 gene, which encodes orotidine-5'-phosphate, is lethal to yeast in the presence of medium containing 5-fluoroorotic acid (5-FOA). Yeast expressing URA3 can also be identified by growing them on media lacking uracil. Thus, depending on growth medium composition, URA3 can be used either for positive or negative selection—it is a selectable/counterselectable reporter gene.

Furthermore, expression of a counterselectable reporter gene is useful in identifying mutations that disrupt interactions between proteins. For example, if the interaction of X and Y moieties (on bait and fish fusion proteins, respectively) triggers expression of the URA3 gene, yeast expressing X and Y will not grow on media containing 5-FOA. However, if X and Y can no longer interact (e.g., because of a fortuitous or an intentional mutation in either moiety), yeast expressing the disruptive mutation(s) will now be able to grow on media containing 5-FOA but will not be able to grow on media lacking uracil. Thus, these techniques enable not just identification of interacting proteins, but also the analysis of points of contact between partners.

Although eukaryotic protein-protein interactions can be studied with relative ease using Y2H systems, identifying interactions between genomic DNA and proteins remains difficult. While many DNA-binding proteins and their cognate nucleic acid sequences are known, the genomic context of these sequences, the genes they regulate, and the biological processes they control remain unknown. Furthermore, screening of genomic libraries for sequences recognized by DNA-binding proteins using conventional techniques is simply too expensive, cumbersome, time-consuming, and unreliable.

The yeast one-hybrid (Y1H) system (Li and Herskowitz, 1993), derived from the Y2H system for detecting protein-protein interactions, provided the first in vivo method to isolate and identify a protein that interacts with a known DNA sequence. Briefly, a library of genomic yeast DNA sequences was cloned into an expression vector upstream of and in frame with a GAL4 activation domain sequence, producing protein coding sequences fused to the GAL4 AD—an expression library. The expression library was transformed into a yeast reporter strain containing a lacZ reporter gene under the control of four copies of a yeast autonomous replicating sequence (ARS) consensus sequence (ACS). Hybrid proteins that recognized the ACS binding site activated transcription of lacZ, turning the cell blue in a β-galactosidase assay.

The methods of the present invention bear similarities to the yeast one-hybrid system (Li & Herskowitz, 1993). The yeast one-hybrid system uses an oligonucleotide, containing a known DNA recognition site, as "bait" for unknown DNA-binding proteins. In contrast, the methods of the present invention employ known or putative DNA-binding proteins as "bait" to screen a stable genomic DNA library containing all DNA recognition sites within the genome, both known and unknown. The yeast one-hybrid system described above uses a genomic DNA library contained in an expression vector, a system that inherently introduces bias to the screening method. In contrast, the methods of the present invention use a stable genomic library designed to eliminate such bias.

While it is theoretically possible to reverse the standard Y1H screen, using unknown genomic DNA fragments to identify promoter elements directly bound by a known DNA-binding protein (e.g., a transcription factor), all prior reports of Y1H screens have failed to appreciate or anticipate that the expression library used is biased because the plasmid vector itself can drive transcription and translation of the inserted DNA, resulting in sequence rearrangements, small deletions in the insert, or outright loss of the insert. Additionally, the DNA-binding protein expressed from the inserted DNA may be toxic to host cell. Furthermore, fusion of the yeast transcriptional activation domain to the carboxyl terminus of the DNA-binding protein expressed from the DNA inserted in to a vector may inhibit the ability of the DNA-binding protein to interact with its recognition sequence, while its fusion to the amino terminus of the DNA-binding protein expressed from the DNA inserted in to a vector may be toxic to host cells. Alternatively, if genomic DNA inserted into a vector contains a promoter or enhancer sequence itself, it too may drive transcription and result in unintended or toxic effects. Therefore, such genomic DNA sequences will not be identified to any DNA-binding protein because the deleterious effects they produce in conventional Y1H systems will delete them from the genomic library. Unfortunately, such missing sequences are likely the very objects of a Y1H screen. Thus, the prior art fails to recognize that potentially meaningful and important interaction candidates are eliminated from most Y2H and Y1H library screens, for numerous reasons, and fails to teach methods of overcoming this limitation.

Another conventional method of identifying genomic regulatory elements that are recognized and bound by specific DNA-binding proteins is chromatin immunoprecipitation (ChIP), and its variants: ChIP paired-end diTag (ChIP-PET) sequencing; and ChIP microarray (ChIP-chip). ChIP (Orlando et al., 1997) is a procedure used to determine whether a known protein binds to or is localized to a specific genomic DNA sequence in vivo (e.g., in mammalian cells). Using formaldehyde (a process known as "fixation"), DNA-binding proteins are crosslinked to DNA in vivo (i.e., host cells are "fixed" with formaldehyde). Chromatin from the cells is isolated, and the DNA is sheared or restriction-digested into small fragments (some of which are also comprised of crosslinked DNA). Crosslinked DNA-binding proteins are immunoprecipitated using protein-specific antibodies, and so co-immunoprecipitating any attached DNA attached to the proteins. The crosslinking is reversed, and polymerase chain reaction (PCR) is used to amplify specific DNA sequences to identify those that were bound to the protein and co-immunoprecipitated with the antibody. Alternatively, the isolated fragments can be cloned into a plasmid vector for subsequent sequence analysis. Either method provides a population of DNA fragments that are able to interact with the particular DNA-binding protein used. ChIP-PET (Wei et al., 2006) is an enhanced ChIP technique whereby two 18 base-pair sequence tags, one from each end of a DNA fragment isolated by ChIP, are extracted and joined together. The joined tags are then sequenced to identify transcription factor binding sites. Finally, ChIP and ChIP-PET techniques may be enhanced further by hybridizing the extracted sequences to a microarray chip (ChIP-chip) (Ren et al., 2000).

While ChIP and its variants can provide valuable information regarding binding sites for DNA-binding proteins—transcription factors in particular—the methods suffer significant limitations. ChIP analysis requires extensive cellular manipulations with multiple steps that must be optimized for each individual DNA-binding protein to be analyzed. ChIP analysis is also dependent on the ability to express the desired DNA-binding protein in a suitable cell type. The major disadvantage of ChIP techniques is the requirement for highly specific antibodies for each protein to be tested. The immunoprecipitation steps of ChIP analysis can be limited severely by the lack of suitable antibodies specific for the DNA-binding protein, and so may require the creation of an epitope-tagged protein (e.g., incorporating an HA or c-Myc moiety at the C- or N-terminus of the DNA-binding protein). In the absence of an antibody specific for the protein tested, any epitope tag added may be masked when the DNA-binding protein is bound to the DNA, severely inhibiting the ability of the epitope-specific antibody to immunoprecipitate the DNA-binding protein. Because ChIP is performed in a cellular context, the analysis is limited to identifying regulatory elements active only in that particular cell type. In the ChIP-chip procedure, analysis is limited to the regions of genomic DNA present on the microarray chips. Finally, ChIP-chip analysis requires the purchase and maintenance of expensive microarray systems, in addition to experienced personnel to assist in analyzing the results.

Therefore, although certain elements of the present invention bear similarities to existing methods, the methods of the present invention are distinct from other methods in that they involve a stable genomic library present in a plasmid vector and are directed at identifying DNA regulatory elements, not just at identifying a synthetic DNA recognition sequence homolog or an unknown DNA-binding protein.

The technical problem underlying the present invention was therefore to overcome these prior art difficulties, furnishing a system that reliably produces clones bearing interacting DNA-binding proteins and their cognate DNA binding sites, and is suitable for large-scale protein-versus-library screens.

The solution to the technical problem above is provided by the embodiments characterized in the claims.

BRIEF SUMMARY OF THE INVENTION

The ability to easily and quickly screen an entire genome for potential targets of a specific transcription factor would provide valuable information about some of the molecular mechanisms behind cancers, such as ARMS, as well as the sequences and genomic locations of the DNA-binding domains. To this end, we developed an improved method for in vivo screening of genomic DNA libraries in yeast—a system for "pulling out regulatory elements" in yeast, or "Yeast PORE"—starting with Pax3, FKHR, and Pax3-FKHR as a model system. The improved methods of this invention encompass general methods that can be adapted to identify the targets of any known or suspected transcription factor or other DNA-binding protein. Our assay provides a method of identifying specific gene targets of transcription factors or other DNA-binding proteins by testing their ability to directly bind genomic elements in vivo. This method has distinct advantages over other screening methods presently available in that it involves an assay that is directly dependent on the binding of known or suspected DNA-binding proteins (e.g., Pax3, FKHR, or Pax3-FKHR) to the promoter elements that they control, made available in a stable genomic DNA library, and therefore allows for a full examination of the natural, in vivo genomic DNA substrates of any protein.

Accordingly, the present invention features, in one aspect, a method for determining whether a test protein interacts with a test nucleic acid sequence, the method comprising: (a) providing a population of competent cells wherein a plurality of the cells of said population contain: (i) a reporter gene operably linked to a test nucleic acid sequence; (ii) a fusion gene, wherein the fusion gene expresses a hybrid protein, said hybrid protein comprising a test protein covalently bonded to a gene activating moiety; and (b) detecting expression of the reporter gene as a measure of the ability of the test protein to interact with the test nucleic acid sequence, wherein the test nucleic acid sequence in the population of competent cells is derived from a genomic DNA library.

Preferably, the genomic DNA library is a stable genomic DNA library. In addition, the reporter gene may be selected from the group consisting of selectable reporter genes, counters electable reporter genes, and selectable/counterselectable reporter genes. The reporter gene may also be selected from the group consisting of amino acid biosynthetic genes, nucleic acid biosynthetic genes, and antibiotic resistance genes. The reporter gene may also be selected from the group consisting of LEU2, HIS3, TRP1, and URA3. Furthermore, the reporter gene and test nucleic acid sequence may be located on a first plasmid, and the first plasmid may comprise one or more transcription terminators upstream of the test nucleic acid sequence and one or more transcription terminators downstream of the reporter gene. Preferably, the first plasmid is a low copy number plasmid, and may further comprise a first selectable marker. Most preferably, the first plasmid is pKAD202. In yet another embodiment of the invention, the fusion gene may be located on a second plasmid. Preferably, the second plasmid comprises an ADH1 terminator and a terminator selected from the group consisting of T3 terminator, T7 terminator, and TonB terminator, downstream of the fusion gene, and wherein the second plasmid further comprises a second selectable marker, wherein the second selectable marker is not the same as the first selectable marker. If desired, the second plasmid may be a high copy number plasmid, or it may be a low copy number plasmid. Preferably, if the second plasmid is a high copy number plasmid, it is pSMACK601 or pSPANK201. Preferably, if the second plasmid is a low copy number plasmid, it is pSMACK701 or pSPANK301.

In this aspect of the invention, the test nucleic acid sequence preferably comprises genomic DNA, wherein the genomic DNA is comprised of genomic DNA fragments, and wherein the genomic DNA fragments are cloned into the first plasmid. If desired, the test nucleic acid sequence may comprise a randomly generated sequence and/or an intentionally designed sequence. In yet another embodiment of this aspect of the invention, the test protein comprises an intentionally designed sequence. Preferably, the test protein is selected from the group consisting of known DNA-binding proteins and suspected DNA-binding proteins. Most preferably, the test protein is selected from the group consisting of Pax3, FKHR, and Pax3-FKHR. Preferably, the population of competent cells is yeast cells, and more preferably *S. cerevisiae* cells. Also preferably, the gene activating moiety comprises the transcription activation domain of a protein selected from the group consisting of GAL4 and B42.

This aspect of the invention further comprises isolating a cell that expresses the reporter gene, thereby producing an isolated cell. Plasmid DNA may be isolated from the isolated cell, at least a portion of a test nucleic acid sequence of the isolated cell may by amplified, and at least a portion of a test nucleic acid sequence of the isolated cell may be sequenced. If desired, a probe may be hybridized to the DNA of the isolated cell. Genomic DNA of interest derived from the methods and processes of the present invention can be used as a probe in a DNA hybridization assay against DNA extracted from yeast colonies and organized on a solid support (e.g., a nitrocellulose filter). By identifying a yeast colony to which the DNA of interest hybridizes, one immediately has identified a yeast strain containing a molecule which interacts with the protein of interest encoded by the DNA of interest. The regulatory element that interacts with the protein of interest can then be cloned from a yeast cell derived from a hybridization positive colony.

In a second aspect, the invention features a cell comprising: (i) a reporter gene operably linked to a test nucleic acid sequence; (ii) a fusion gene, wherein the fusion gene expresses a hybrid protein, said hybrid protein comprising a test protein covalently bonded to a gene activating moiety; and (b) wherein the test nucleic acid sequence in the population of competent cells is derived from a genomic DNA library.

Preferably, the genomic DNA library is a stable genomic DNA library. In addition, the reporter gene may be selected from the group consisting of selectable reporter genes, counterselectable reporter genes, and selectable/counterselectable reporter genes. The reporter gene may also be selected from the group consisting of amino acid biosynthetic genes, nucleic acid biosynthetic genes, and antibiotic resistance genes. The reporter gene may also be selected from the group consisting of LEU2, HIS3, TRP1, and URA3. Furthermore, the reporter gene and test nucleic acid sequence may be located on a first plasmid, and the first plasmid may comprise one or more transcription terminators upstream of the test nucleic acid sequence and one or more transcription terminators downstream of the reporter gene. Preferably, the first plasmid is a low copy number plasmid, and may further comprise a first selectable marker. Most preferably, the first plasmid is pKAD202. In yet another embodiment of this aspect, the fusion gene may be located on a second plasmid. Preferably, the second plasmid comprises an ADH1 terminator and a terminator selected from the group consisting of T3 terminator, T7 terminator, and TonB terminator, downstream of the fusion gene, and wherein the second plasmid further comprises a second selectable marker, wherein the second selectable marker is not the same as the first selectable marker. If desired, the second plasmid may be a high copy number plasmid, or it may be a low copy number plasmid. Preferably, if the second plasmid is a high copy number plasmid, it is pSMACK601 or pSPANK201. Preferably, if the second plasmid is a low copy number plasmid, it is pSMACK701 or pSPANK301.

In this aspect of the invention, the test nucleic acid sequence preferably comprises genomic DNA, wherein the genomic DNA is comprised of genomic DNA fragments, and wherein the genomic DNA fragments are cloned into the first plasmid. If desired, the test nucleic acid sequence may comprise a randomly generated sequence and/or an intentionally designed sequence. In yet another embodiment of this aspect of the invention, the test protein comprises an intentionally designed sequence. Preferably, the test protein is selected from the group consisting of known DNA-binding proteins and suspected DNA-binding proteins. Most preferably, the test protein is selected from the group consisting of Pax3, FKHR, and Pax3-FKHR. Preferably, the cell is a yeast cell, and more preferably an *S. cerevisiae* cell. Also preferably, the gene activating moiety comprises the transcription activation domain of a protein selected from the group consisting of GAL4 and B42.

The invention further features several genetic constructs—plasmids—which are useful in practicing various aspects of the invention. In one aspect, the genetic construct comprises a circular plasmid, further comprising: (a) a protein expression cassette, wherein the protein expression cassette comprises: (i) a GAL1 promoter operably linked to a multiple cloning site, a nuclear localization signal, a B42 acid blob domain, and an epitope tag; (b) a bacterial origin of replication; (c) at least one transcriptional terminator between said protein expression cassette and said origin of replication; (d) a marker gene; (e) a ROP gene between said bacterial origin of replication and said marker gene; (f) a reporter gene; (g) and an element. A preferred 5' to 3' order for the protein expression cassette is: GAL1 promoter, multiple cloning site, nuclear localization signal, B42 acid blob domain, epitope tag, transcriptional terminator; and another preferred 5' to 3' order is: GAL1 promoter, nuclear localization signal, B42 acid blob domain, epitope tag, multiple cloning site, transcriptional terminator. Preferably, the at least one transcriptional terminator is configured to terminate RNA transcripts entering said bacterial origin of replication from said protein expression cassette. As desired, the marker gene is selected from the group consisting of ampicillin resistance gene, kanamycin resistance gene, and chloramphenicol acetyltransferase gene. As desired, the reporter gene is selected from the group consisting of LEU2, HIS3, TRP1, and URA 3. As desired, the element may be a 2μ sequence or a CEN4 centromeric sequence and an ARS6 origin of replication (CEN4/ARS6 origin of replication). Preferably, the genetic construct is pSMACK601, pSMACK701, pSPANK201, or pSPANK301.

In another aspect, the genetic construct comprises a circular plasmid, further comprising: a multiple cloning site (MCS) upstream of a minimal promoter operably linked to a reporter gene; a bacterial origin of replication; a yeast origin of replication; a first marker gene, a repressor of primer (ROP) gene; a second marker gene; and one or more transcription terminators. Preferably, the 5' to 3' order of the features is: MCS; minimal promoter operably linked to a reporter gene; first transcription terminator; first marker gene; ROP gene; second marker gene; yeast origin of replication; second transcription terminator; bacterial origin of replication; and third transcription terminator. As desired, the minimal promoter and reporter gene may be a minimal HIS3 promoter and HIS3, respectively. As desired, the first marker gene may be an ampicillin resistance gene, or a kanamycin resistance gene. As desired, the second marker gene may be selected from the group consisting of LEU2, HIS3, TRP1, and URA 3. The yeast origin of replication may be 2μ, but is preferably CEN4/ARS6. The bacterial origin of replication may be ColE1; the transcription terminators may be selected from the group consisting of T7, T3, TonB, and ADH1 terminator sequences. Most preferably, the genetic construct is pKAD202.

DEFINITIONS

In the following description, terms relating to recombinant DNA technology are used.

The following definitions are provided to give a clear understanding of the specification and appended claims.

By "gene" is meant a nucleic acid (e.g., deoxyribonucleic acid, or "DNA") sequence that comprises coding sequences necessary for the production of a polypeptide or precursor (e.g., messenger RNA, or "mRNA"). The polypeptide may be encoded by a full length coding sequence or by any portion of the coding sequence, so long as the desired activity or functional properties (e.g., enzymatic activity, ligand binding, signal transduction, etc.) are retained. The term also encompasses the coding region of a structural gene and the sequences located adjacent to the coding region on both the 5' and 3' ends, for a distance of about 1 kb on either end, such that the gene is capable of being transcribed into a full-length mRNA. The sequences located 5' of the coding region and which are present on the mRNA are referred to as 5' untranslated sequences, and form the 5' untranslated region (5' UTR). The sequences located 3' or downstream of the coding region and which are present on the mRNA are referred to as 3' non-translated sequences, and form the 3' untranslated region (3' UTR). The term "gene" encompasses both cDNA and genomic forms of a gene. The genomic form or clone of a gene usually contains the coding region interrupted with non-coding sequences termed "introns" (also called "intervening regions" or "intervening sequences"). Introns are segments of a gene which are transcribed into nuclear RNA (hnRNA); introns may contain regulatory elements such as enhancers. Introns are removed or "spliced out" from the nuclear or primary transcript, and therefore are absent from the mRNA transcript. mRNA functions during translation to specify the sequence or order of amino acids in a nascent polypeptide.

By "nucleotide" is meant a monomeric structural unit of nucleic acid (e.g., DNA or RNA) consisting of a sugar moiety (a pentose: ribose, or deoxyribose), a phosphate group, and a nitrogenous heterocyclic base. The base is linked to the sugar moiety via a glycosidic bond (at the 1' carbon of the pentose ring) and the combination of base and sugar is called a nucleoside. When the nucleoside contains a phosphate group bonded to the 3' or 5' position of the pentose, it is referred to as a nucleotide. When the nucleotide contains one such phosphate group, it is referred to as a nucleotide monophosphate; with the addition of two or three such phosphate groups, it is called a nucleotide diphosphate or triphosphate, respectively. The most common, nucleotide bases are derivatives of purine or pyrimidine, with the most common purines being adenine and guanine, and the most common pyrimidines being thymidine, uracil, and cytosine. A sequence of operatively linked nucleotides is typically referred to herein as a "base sequence" or "nucleotide sequence" or "nucleic acid sequence," and is represented herein by a formula whose left-to-right orientation is in the conventional direction of 5'-terminus to 3'-terminus. A "test nucleic acid sequence" is a nucleic acid sequence used according to the methods of the present invention to measure or test interaction between said nucleic acid sequence and a protein. The test nucleic acid sequence may be a genomic DNA fragment.

By "polynucleotide molecule" is meant a molecule comprised of multiple nucleotides. Nucleotides are the basic unit of DNA, and consist of a nitrogenous base (adenine, guanine, cytosine, or thymine), a phosphate molecule, and a deoxyribose molecule. When linked together, they form polynucleotide molecules.

DNA molecules are said to have “5' ends” and “3' ends” because mononucleotides are joined to make oligonucleotides in a manner such that the 5' phosphate of one mononucleotide pentose ring is attached to the 3' oxygen of its neighbor in one direction, via a phosphodiester linkage. Therefore, an end of an oligonucleotide is referred to as the “5' end” if its 5'-phosphate is not linked to the 3' oxygen of a mononucleotide pentose ring. Alternatively, it is the “3' end” if its 3' oxygen is not linked to a 5' phosphate of a subsequent mononucleotide pentose ring. These ends are also referred to as “free” ends because they are not linked to upstream or downstream mononucleotides, respectively. A double stranded nucleic acid molecule may also be said to have 5'- and 3' ends, wherein the “5'” refers to the end containing the accepted beginning of the particular region, gene, or structure, and the “3'” refers to the end downstream of the 5' end. A nucleic acid sequence, even if internal to a larger oligonucleotide, may also be said to have 5' and 3' ends, although these ends are not free ends. In such a case, the 5' and 3' ends of the internal nucleic acid sequence refer to the 5' and 3' ends that said fragment would have were it isolated from the larger oligonucleotide. In either a linear or circular DNA molecule, discrete elements may be referred to as being “upstream” or 5' of the “downstream” or 3' elements. Ends are said to “compatible” if: a) they are both blunt or contain complementary single strand extensions (such as that created after digestion with a restriction endonuclease); and b) at least one of the ends contains a 5' phosphate group. Compatible ends are therefore capable of being ligated by a double stranded DNA ligase (e.g., T4 DNA ligase) under standard conditions. Nevertheless, blunt ends may also be ligated.

By “promoter” is meant a DNA sequence usually found at the 5' region of a gene, proximal to the start codon. Transcription of an adjacent gene is initiated at the promoter region. If the promoter is an inducible promoter, the rate of transcription increases in response to an inducing agent.

By “minimal promoter” is meant a promoter is the noncoding sequence upstream (5' direction) of a gene, providing a site for RNA polymerase to bind and initiate transcription. A minimal promoter is the minimal elements of a promoter, including a TATA box and transcription initiation site, and is inactive unless regulatory enhancer elements are situated upstream.

By “enhancer” is meant a regulatory sequence of DNA that may be located a great distance (thousands of base pairs) upstream or downstream from the gene it controls, or even within an intron of the gene it controls. Binding of DNA-binding proteins to an enhancer influences the rate of transcription of the associated gene.

By “operably linked” is meant that nucleic acid sequences or proteins are operably linked when placed into a functional relationship with another nucleic acid sequence or protein. For example, a promoter sequence is operably linked to a coding sequence if the promoter promotes transcription of the coding sequence. As a further example, a repressor protein and a nucleic acid sequence are operably linked if the repressor protein binds to the nucleic acid sequence. Additionally, a protein may be operably linked to a first and a second nucleic acid sequence if the protein binds to the first nucleic acid sequence and so influences transcription of the second, separate nucleic acid sequence. Generally, “operably linked” means that the DNA sequences being linked are contiguous, although they need not be, and that a gene and a regulatory sequence or sequences (e.g., a promoter) are connected in such a way as to permit gene expression when the appropriate molecules (e.g., transcriptional activator proteins—transcription factors—or proteins which include transcriptional activator domains) are bound to the regulatory sequence or sequences.

By “genomic DNA” is meant all the DNA sequences comprising the genome (the total genetic information carried) of a cell or organism By “genomic DNA library” is meant a collection of genomic DNA that includes all the DNA sequences of a given species (e.g., a human genomic DNA library, or a simply human genomic library). For example, human genomic double-stranded DNA is cleaved with restriction endonuclease or mechanically sheared (e.g., by sonication), generating millions of “genomic DNA fragments.” These fragments are cloned (inserted via ligation) into plasmids, thus creating recombinant DNA molecules. The recombinant molecules are introduced in to bacteria by standard means known in the art, generating millions of different colonies of transfected bacterial cells. Each of these colonies is clonally derived from a single ancestor cell, and so contains many copies of a particular region of the fragmented genome. The plasmids are referred to as containing a genomic DNA clone, and the collection of plasmids is a genomic DNA library. A genomic DNA library is said to be “stable” when the library is constructed in such a manner that the genomic DNA insert does not promote unwanted transcription into the vector housing the library, which would induce recombination and destabilization of the vector, and the vector is maintained at a low copy number. For example, but without limitation, the vector may lack a promoter upstream of the inserted genomic DNA, it may contain terminator sequences configured to flank the inserted genomic DNA, and it may contain a CEN4/ARS6 low-copy-number yeast origin of replication. A preferred example of such a vector is pKAD202, described more fully below.

By “genomic DNA ligand” is meant a stretch of genomic DNA that provides or represents a binding site for a DNA-binding protein (i.e., a segment of DNA that is necessary and sufficient to specifically interact with a given polypeptide, such as a DNA-binding protein). The portion of the DNA-binding protein that specifically interacts with the genomic DNA ligand is referred to as a “ligand binding domain” or “DNA-binding domain.”

By “DNA-binding protein” is meant any of numerous proteins which can or may specifically interact with a nucleic acid. For example, a DNA-binding protein used in the invention can be the portion of a transcription factor which specifically interacts with a nucleic acid sequence in the promoter of a gene. Alternatively, the DNA-binding protein can be any protein which specifically interacts with a sequence which is naturally-occurring or artificially inserted into the promoter of a reporter gene. Where protein/DNA interactions are characterized, the DNA-binding protein can be covalently bonded to a solid support (e.g., the DNA-binding protein may be expressed as a fusion protein, bearing an epitope tag, which epitope tag may facilitate binding to the solid support, which may be agarose beads). A “test protein” may be shown to be a “DNA-binding protein” by the methods of the invention.

By “fusion” or “hybrid” protein, DNA molecule, or gene is meant a chimera of at least two covalently bonded polypeptides or DNA molecules By “DNA-binding domain” or “DNA-binding moiety” is meant a polypeptide sequence or cluster which is capable of directing specific polypeptide binding to a particular DNA sequence (i.e., to a genomic DNA ligand). The term “domain” in this context is not intended to be limited to a single discrete folding domain. Rather, consideration of a polypeptide as a “DNA-binding domain” for use in the methods of this invention can be made simply by the observation that the polypeptide has specific DNA binding activity or that the polypeptide shares sequence similarity with proteins having known DNA-binding activity.

By "gene activating moiety" or "transcription activation domain" is meant a stretch of amino acids that is covalently bonded to a test protein (i.e., as a fusion protein), wherein the gene activating moiety is capable of inducing the expression of a gene (e.g., a reporter gene) that is operably linked to an upstream test nucleic acid sequence when the test nucleic acid sequence contains a genomic DNA ligand for the test protein and the protein binds to the genomic DNA ligand.

By "protein" or "polypeptide" is meant a sequence of amino acids of any length, constituting all or a part of a naturally-occurring polypeptide or peptide, or constituting a non-naturally occurring polypeptide or peptide (e.g., a randomly generated peptide sequence or one of an intentionally designed collection of peptide sequences). A "test protein" or "test polypeptide" is a protein used according to the methods of the present invention to measure or test interaction between nucleic acids and said test protein or test polypeptide.

By "expression" or "gene expression" is meant transcription (e.g., from a gene) and, in some cases, translation of a gene into a protein, or "gene product." In the process of expression, a DNA chain coding for the sequence of gene product is first transcribed to a complementary RNA, which is often a messenger RNA, and, in some cases, the transcribed messenger RNA is then translated into the gene product—a protein. The terms are also used to mean the degree to which a gene is active in a cell or tissue, measured by the amount of mRNA in the tissue and/or the amount of protein expressed.

As used herein, the terms "vector" or "plasmid" or "plasmid vector" are used in reference to extra-chromosomal nucleic acid molecules capable of replication in a cell and to which an insert sequence can be operatively linked so as to bring about replication of the insert sequence. Vectors are used to transport DNA sequences into a cell, and some vectors may have properties tailored to produce protein expression in a cell, while others may not. A vector may include expression signals such as a promoter and/or a terminator, a selectable marker such as a gene conferring resistance to an antibiotic, and one or more restriction sites into which insert sequences can be cloned. Vectors can have other unique features (such as the size of DNA insert they can accommodate). A plasmid or plasmid vector is an autonomously replicating, extrachromosomal, circular DNA molecule (usually double-stranded) found mostly in bacterial and protozoan cells. Plasmids are distinct from the bacterial genome, although they can be incorporated into a genome, and are often used as vectors in recombinant DNA technology.

The term "prokaryotic termination sequence," "transcriptional terminator," "terminator sequence," or "terminator" refers to a nucleic acid sequence, recognized by an RNA polymerase, that results in the termination of transcription. Prokaryotic termination sequences commonly comprise a GC-rich region that has a twofold symmetry, followed by an AT-rich sequence. Commonly used prokaryotic termination sequences are the ADH1, T7, T3, and TonB termination sequences. A variety of termination sequences are known in the art and may be employed in the nucleic acid constructs of the present invention, including the $T_{INT}$, $T_{L1}$, $T_{L2}$, $T_{R1}$, $R_{R2}$, $T_{6S}$ termination signals derived from the bacteriophage lambda, and termination signals derived from bacterial genes such as the trp gene of *E. coli*.

By "reporter gene" is meant a gene whose expression can be assayed as a measure of the ability of two test molecules to interact (i.e., as a measure of protein/DNA interactions). A useful reporter gene is operably linked to an upstream test nucleic acid sequence, which may or may not contain a DNA-binding-protein recognition site, to which a reconstituted transcription factor or DNA-binding protein of interest or test protein binds. Such genes include, without limitation, lacZ, amino acid biosynthetic genes (e.g., the yeast LEU2, HIS3, LYS2, or TRP1), URA3 genes, nucleic acid biosynthetic genes, the bacterial chloramphenicol transacetylase (CAT) gene, and the bacterial gus gene. Certain reporter genes are considered to be "selectable," "counterselectable," or "selectable/counterselectable" reporter genes, as is described below By "selectable" reporter gene is meant a reporter gene which, when it is expressed under a certain set of conditions, confers a growth advantage on cells containing it. Examples of selectable reporter genes include LEU2 and TRP1.

By "counterselectable" reporter gene is meant a reporter gene which, when it is expressed under a certain set of conditions, prevents the growth of a cell containing it. Examples of counterselectable reporter genes include URA3, LYS2, GAL1, CYH2, and CAN1.

By "selectable/counterselectable" reporter gene is meant a reporter gene which, when it is expressed under a certain set of conditions, is lethal to a cell containing it, and when it is expressed a different set of conditions, confers a selective growth advantage on cells containing it. Thus, a single gene can be used as both a selectable reporter gene and a counterselectable reporter gene. Examples of selectable/counterselectable reporter genes include URA3, LYS2, and GAL1. In each aspect of the invention where a selectable/counterselectable reporter gene is employed, a combination of a selectable reporter gene and a counterselectable reporter gene can be used in lieu of a single selectable/counterselectable reporter gene. For example, yeast cells may first be transfected with plasmid bearing a selectable reporter gene, and transformants identified by their growth on appropriate media (e.g, synthetic complete media lacking leucine). These transformants could then be transformed with a second plasmid bearing a counterselectable reporter gene, and double-transformants identified by their growth on appropriate media (e.g., synthetic complete media lacking leucine and uracil, but containing 5-FOA).

As used herein, the terms "selectable marker," "selectable marker sequence," "selectable marker gene," or "marker gene" refers to a gene or other DNA fragment that encodes or provides an activity conferring the ability to grow or survive in what would otherwise be a deleterious environment. For example, a selectable marker may confer resistance to an antibiotic or drug (e.g., ampicillin or kanamycin) upon the host cell in which the selectable marker is expressed. An origin of replication (Ori) may also be used as a selectable marker enabling propagation of a plasmid vector. Further examples include, without limitation, kanamycin resistance genes, ampicillin resistance genes, LEU2, TRP1, and HIS3.

By "ROP gene" is meant a gene encoding the repressor of primer protein, which regulates plasmid DNA replication by modulating the initiation of transcription. It is used to keep plasmid copy number low, thus preventing or minimizing potentially toxic effects to host cells that may arise from cloned genomic DNA fragments.

The term "expression vector" as used herein refers to a recombinant DNA molecule containing a desired coding sequence and appropriate nucleic acid sequences necessary for expression of the operably linked coding sequence (e.g., an insert sequence that codes for a product) in a particular host cell. Nucleic acid sequences necessary for expression in prokaryotes usually include a promoter, an operator (optional), and a ribosome binding site, often along with other sequences.

The term "epitope tag" is meant to include, but not be limited to a GST (glutathione-S-transferase) tag, an HA (haemagglutinin) tag, a Myc tag, a FLAG tag, and a His tag. The preceding listing of such epitope tag polypeptides is meant to be illustrative and not limiting, and there is a large and ever-increasing selection of such epitope polypeptides that are substitutable for substitution with those specifically described herein. One skilled in the art is capable of making desired substitutions without undue experimentation.

As used herein, the term "origin of replication" or "ori" refers to a DNA sequence conferring functional replication capabilities in a host cell. Examples include, but are not limited to, normal or non-conditional origin of replications such as the ColE1 origin, and its derivatives, which are functional in a broad range of host cells. An origin of replication may be a "high copy number" or "low copy number" origin of replication.

As used herein, the term "non-promoter sequence" refers to any nucleic acid sequence that is unable to serve as an operable promoter element for initiating transcription in a given host cell, such as a bacterial host cell, or a eukaryotic host cell. In preferred embodiments, the host cell in which the non-promoter sequence is unable to serve as an operable promoter is an *E. coli* host cell.

As used herein, the terms "insert sequence" or "foreign DNA" refer to any nucleic acid sequences that are capable of being placed in a vector. Examples include, but are not limited to, random DNA libraries and known nucleic acid sequences. A particular "insert sequence" or "foreign DNA" may refer to a pool or a member of a pool of identical nucleic acid molecules, a pool or a member of a pool of non-identical nucleic acid molecules, or a specific individual nucleic acid molecule (e.g., nucleotide sequences encoding Pax3, FKHR, or other proteins).

By "covalently bonded" is meant that two molecules (e.g., DNA molecules or proteins) are joined by covalent bonds, directly or indirectly. For example, the "covalently bonded" proteins or protein moieties may be immediately contiguous, or they may be separated by stretches of one or more amino acids within the same hybrid protein.

By "target protein" or "target DNA molecule" is meant a peptide, protein, domain of a protein, or nucleic acid molecule whose function (i.e., whose ability to interact with a second molecule) is being characterized with the methods of the invention. A target protein may further comprise an epitope tag, and so exist as a fusion protein. Such a fusion protein or target fusion protein may also be "immobilized" on a solid support (e.g., agarose or Sepharose®), which means that the fusion protein has been purified or isolated by affinity chromatography, using a solid support that has attached to it a moiety (e.g., glutathione) with affinity for the epitope tag (e.g., a GST epitope tag).

The terms "interact" and "interacting" are meant to include detectable interactions between molecules, and are intended to include protein interactions with nucleic acid, detectable by the methods of the present invention.

The terms "identification," "identifying," "determining," and "detecting" relate to the ability of the person skilled in the art to detect and distinguish interaction between genomic DNA ligands and target proteins from false positive interactions due to non-specific interaction, and optionally to characterize at least one of said interacting genomic DNA ligands by one or a set of unambiguous features including but not limited to direct sequencing. Preferably, said genomic DNA ligands are characterized by the DNA sequence encoding them, upon isolation, polymerase chain reaction amplification, and sequencing of the respective DNA molecules, according to the methods of the present invention.

By "putative" or "suspected" is meant that the primary, secondary, or tertiary structure of a DNA fragment or a protein bears regions that match primary, secondary, or tertiary structure of known DNA-binding proteins or DNA ligands.

As used herein, the term "host cell" or "competent cell" refers to any cell that can be transformed with heterologous DNA (such as a plasmid vector). Examples of host cells include, but are not limited to: *Saccharomyces cerevisiae* strains W303 (ATCC #200060), K2346 (ATCC #200864), K2348 (ATCC #200865), DY150 (ATCC #96029), K699 (ATCC #200903), K700 (ATCC #201741), or any other strain that has a functional GAL4 and GAL80 gene and is auxotrophic for histidine, leucine, and tryptophan; and *E. coli* strains that contain the F or F' factor (e.g., DH5αF or DH5αF') or *E. coli* strains that lack the F or F' factor (e.g., DH10B).

The term "population" in the context of competent cells or host cells refers to the whole number of such cells in a given sample, colony, or clone. It may be the total of such cells occupying an area on solid medium or some other limited and separated space (e.g., an eppendorf flask). It may also refer to a body, grouping, or cluster of such cells having a particular characteristic in common (e.g., Leucine auxotrophy), or a group of such cells from which samples are taken for measurement.

The term "isolated cell" as used herein refers to a host cell that is selected from amongst other host cells according to at least one identifiable phenotype (e.g., expression of a reporter gene conferring ability to grow on synthetic medium lacking leucine), and set apart from other host cells (e.g., by manually removing and transferring a colony from a plate on which cultures are grown). The processes involved in identifying, selecting and setting apart an isolated cell comprise "isolating a cell."

The term "isolating plasmid DNA" as used herein refers to removing cellular material, or culture medium when the plasmid DNA is produced by recombinant techniques, or removing chemical precursors or other chemicals when chemically synthesized (e.g., after PCR). An "isolated plasmid DNA," then, is substantially free of culture medium, cellular material, chemical precursors, or other chemicals, depending on the method of production.

The term "transformation" or "transfection" as used herein refers to the introduction of foreign DNA into cells (e.g., prokaryotic cells, or host cells). Transformation may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

By "restriction endonuclease" and "restriction enzyme" is meant enzymes (e.g., bacterial enzymes), each of which cut double-stranded DNA at or near a specific nucleotide sequence (a cognate restriction site). Examples include, but are not limited to, BamHI, EcoRV, HindIII, HincII, NcoI, San, and NotI.

By "restriction" is meant cleavage of DNA by a restriction enzyme at its cognate restriction site.

By "restriction site" is meant a particular DNA sequence recognized by its cognate restriction endonuclease.

As used herein, the term "purified" or "to purify" refers to the removal of contaminants from a sample. For example, plasmids are grown in bacterial host cells and the plasmids are purified by the removal of host cell proteins, bacterial genomic DNA, and other contaminants. The percent of plasmid DNA is thereby increased in the sample. In the case of nucleic acid sequences, "purify" refers to isolation of the individual nucleic acid sequences from each other.

As used herein, the terms "sequencing" or "DNA sequence analysis" refers to the process of determining the linear order of nucleotides bases in a nucleic acid sequence (e.g., insert sequence) or clone. These units are the C, T, A, and G bases. Generally, to sequence a section of DNA, the DNA sequence of a short flanking region, i.e., a primer binding site, must be known beforehand. One method for sequencing is called dideoxy sequencing (or Sanger sequencing). One example for performing dideoxy sequencing uses the following reagents: 1) the DNA that will be used as a template (e.g., insert sequence); 2) a primer that corresponds to a known sequence that flanks the unknown sequence; 3) DNA nucleotides, to synthesize and elongate a new DNA strand; 4) dideoxynucleotides that mimic the G, A, T, and C building blocks to incorporate into DNA, but that prevent chain elongation, thus acting as termination bases for a DNA polymerase (the four different dideoxynucleotides also may be labeled with different fluorescent dyes for automated DNA sequence analysis); and 5) a nucleic acid polymerizing agent (e.g., DNA polymerase or Taq polymerase, both of which are enzymes that catalyze synthesis of a DNA strand from another DNA template strand). When these reagents are mixed, the primer aligns with and binds the template at the primer binding site. The polymerizing agent then initiates DNA elongation by adding the nucleotide building blocks to the 3' end of the primer. Randomly, a dideoxynucleotide will integrate into a growing chain. When this happens, chain elongation stops and, if the dideoxynucleotide is fluorescently labeled, the label will be also be attached to the newly generated DNA strand. Multiple strands are generated from each template, each strand terminating at a different base of the template. Thus, a population is produced with strands of different sizes and different fluorescent labels, depending on the terminal dideoxynucleotide incorporated as the final base. This entire mix may, for example, be loaded onto a DNA sequencing instrument that separates DNA strands based on size and simultaneously uses a laser to detect the fluorescent label on each strand, beginning with the shortest. The sequence of the fluorescent labels, read from the shortest fragment to the longest, corresponds to the sequence of the template. The reading may be done automatically, and the sequence may be captured and analyzed using appropriate software. The term "shotgun cloning" refers to the multi-step process of randomly fragmenting target DNA into smaller pieces and cloning them en masse into plasmid vectors.

As used herein, the terms "to clone," "cloned," or "cloning" when used in reference to an insert sequence and vector, mean ligation of the insert sequence into a vector capable of replicating in a host cell. The terms "to clone," "cloned," or "cloning" when used in reference to an insert sequence, a vector, and a host cell, refer generally to making copies of a given insert sequence. In this regard, to clone a piece of DNA (e.g., insert sequence), one would insert it into a vector (e.g., ligate it into a plasmid, creating a vector-insert construct) which may then be put into a host (usually a bacterium) so that the plasmid and insert replicate with the host. An individual bacterium is grown until visible as a single colony on nutrient media. The colony is picked and grown in liquid culture, and the plasmid containing the "cloned" DNA (the sequences inserted into the vector) is re-isolated from the bacteria, at which point there may be many millions of copies of the vector-insert construct. The term "clone" can also refer either to a bacterium carrying a cloned DNA, or to the cloned DNA itself.

As used herein, the term "library" refers to a collection of insert sequences residing in transfected cells, each of which contains a single insert sequence from a genome, sub-cloned into a vector.

The term "electrophoresis" refers to the use of electrical fields to separate charged biomolecules such as DNA, RNA, and proteins. DNA and RNA carry a net negative charge because of the numerous phosphate groups in their structure. Proteins carry a charge that changes with pH, but becomes negative in the presence of certain chemical detergents. In the process of "gel electrophoresis," biomolecules are put into wells of a solid matrix typically made of an inert porous substance such as agarose. When this gel is placed into a bath and an electrical charge applied across the gel, the biomolecules migrate and separate according to size, in proportion to the amount of charge they carry. The biomolecules can be stained for viewing (e.g., with ethidium bromide or with Coomassie dye) and isolated and purified from the gels for further analysis. Electrophoresis can be used to isolate pure biomolecules from a mixture, or to analyze biomolecules (such as for DNA sequencing).

As used herein, the terms "PCR" and "amplifying" refer to the polymerase chain reaction method of enzymatically "amplifying" or copying a region of DNA. This exponential amplification procedure is based on repeated cycles of denaturation, oligonucleotide primer annealing, and primer extension by a DNA polymerizing agent such as a thermostable DNA polymerase (e.g., the Taq or Tfl DNA polymerase enzymes isolated from *Thermus aquaticus* or *Thermus flavus*, respectively).

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "primer" refers to an oligonucleotide, whether occurring naturally as in a purified restriction digest or produced synthetically, which is capable of acting as a point of initiation of nucleic acid synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucieotide. The primer must be sufficiently long to prime the synthesis of extension products in the presence of the inducing agent. The exact lengths of the primers will depend on many factors, including temperature, source of primer, and the use of the method.

As used herein, the term "target," in regards to PCR, refers to the region of nucleic acid bounded by the primers. Thus, the "target" is sought to be sorted out from other nucleic acid sequences. A "segment" is defined as a region of nucleic acid within the target sequence.

As used herein, the terms "PCR product," "PCR fragment," and "amplification product" refer to the resultant mixture of compounds after two or more cycles of the PCR steps of denaturation, annealing, and extension are complete. These terms encompass the case where there has been amplification of one or more segments of one or more target sequences.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The following examples are offered by way of illustration and not by way of limitation.

Example 1

Yeast Strains

The yeast strains used in the invention can be grown and maintained with standard methods. *Saccharomyces cerevisiae* are particularly useful in the invention. *S. cerevisiae* strains with functional GAL4 and GAL80 genes and that are auxotrophic for histidine, leucine, and tryptophan are particularly useful in the invention. Examples of such strains include, without exception, strains W303 and K2346.

Example 2

Construction of bait vectors pSMACK601, pSMACK701, pSPANK201, and pSPANK301

Figure 1:
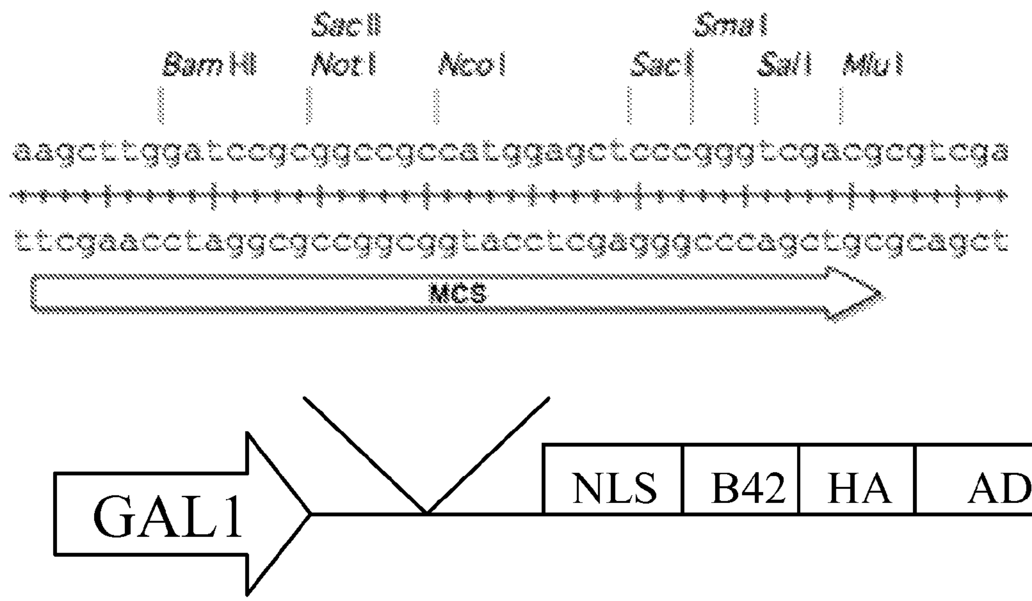
FIG. 1 is a schematic representation of the protein expression cassette in bait vectors pSMACK601 (SEQ ID NO: 1) and pSMACK701 (SEQ ID NO: 2), used for galactose-inducible expression of a transcription factor of interest with a C-terminal fusion tag.
Figure 2:
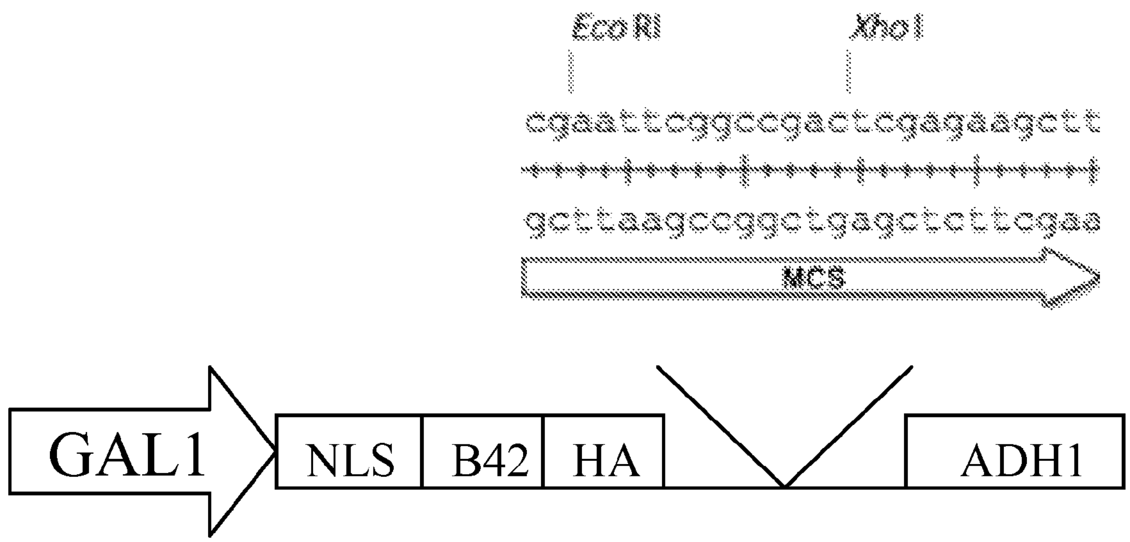
FIG. 2 is a schematic representation of the protein expression cassette in bait vectors pSPANK201 (SEQ ID NO: 13) and pSPANK301 (SEQ ID NO: 14), used for galactose-inducible expression of a transcription factor of interest with an N-terminal fusion tag.

The four bait vectors are derivatives of the pSMART®LC-Amp cloning vector (Lucigen Corp., Middleton, Wis.), and are designed to allow for galactose-inducible expression of a transcription factor of interest cloned into a multiple cloning ("multi-cloning") site. The expressed protein is fused to a tag containing a yeast nuclear localization signal, the B42 acid blob domain, and an HA tag at either the carboxyl- or amino-terminus of the protein (FIGS. 1 and 2, respectively). All four plasmids offer the following features: (i) the LEU2 gene, which acts as a selectable marker in yeast; (ii) the Ampicillin resistance gene and Col E1 origin of replication to allow for selection and propagation in *E. coli*.; (iii) a protein expression cassette comprising a GAL1 promoter, which allows for galactose inducible expression, a multiple cloning site, a hemagglutinin (HA) epitope tag, a nuclear localization signal, and a B42 acid blob domain; (iv) an ADH1 terminator; (v) TonB, T7, and T3 terminator sequences; (vi) a repressor of primer (ROP) gene; and (vii) either a CEN4/ARS1 yeast origin of replication, which allows the plasmid to be maintained at low copy numbers, or a 2μ yeast origin of replication, which allows the plasmid to be maintained at high copy number plasmids.

Figure 3:
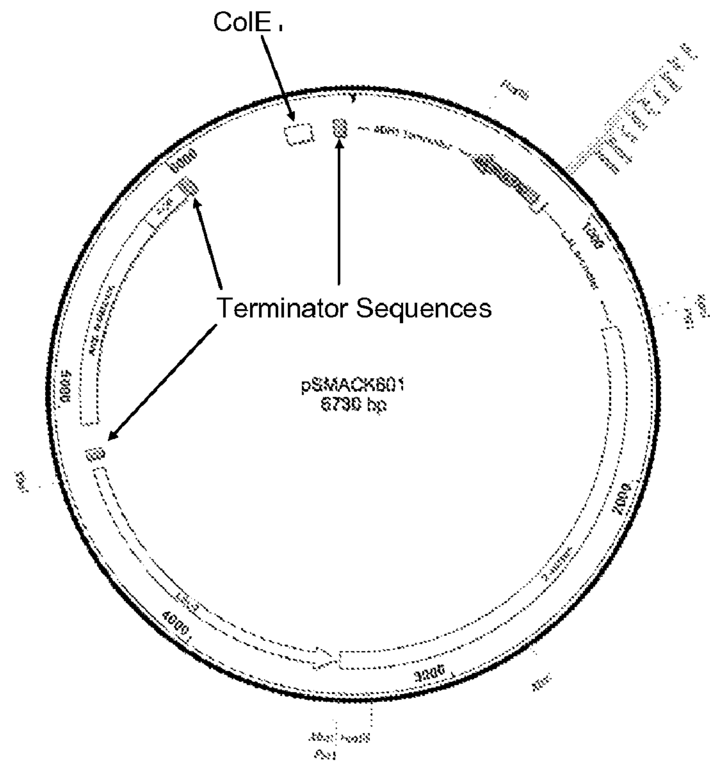
FIG. 3 is a map of bait vector pSMACK601, which uses the C-terminal fusion expression cassette and contains the 2μ high-copy number yeast origin of replication.
Figure 4:
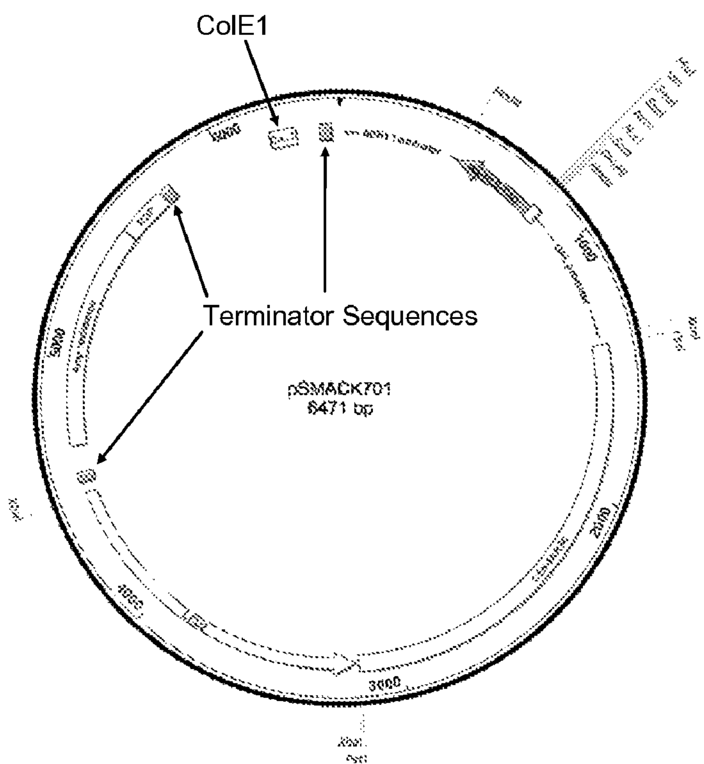
FIG. 4 is a map of bait vector pSMACK701, which uses the C-terminal fusion expression cassette and contains the CEN4/ARS6 low-copy number yeast origin of replication.

The plasmids pSMACK601 (FIG. 3, TABLE 1, and SEQ ID NO:1) and pSMACK701 (FIG. 4, TABLE 2, and SEQ ID NO:2) are designed to express the transcription factor of interest with a carboxyl-terminal fusion of the tag described above. pSMACK601 also contains the 2μ sequence, which allows the plasmid to be maintained at high copy numbers in yeast, while pSMACK701 contains the yeast ARS6 origin of replication and the CEN4 centromeric sequence, yielding a low copy number in yeast.

Both vectors were constructed by first amplifying the LEU2 gene from the plasmid pGADT7-Rec2 using LEU2F primer (5'-CGTCTAGACCTACCCTATGAACATATTCC-3') (SEQ ID NO:3) and LEU2R primer (5'-CGTCTAGACCTATTGTTTTTTTCCAATAGG-3') (SEQ ID NO:4), which added an XbaI site to each end of the resulting PCR product. The PCR product was digested with XbaI and subsequently ligated into the XbaI site of pSMART LC AMP to generate the intermediate plasmid, pSL101.

Next, an oligonucleotide MPT (5'-AATTGCTGCAGC-3') (SEQ ID NO:5) was self-annealed to create a linker with MfeI ends and an internal PstI site. This linker was ligated into the EcoRI site of the pSL101 construct, destroying the EcoRI site and adding a unique PstI site to generate the intermediate, pSL102.

The oligonucleotide, mHB (5'-AGCTGCGAGATCTCGC-3') (SEQ ID NO:6) was then self-annealed to create a linker with modified HindIII ends and an internal BglII site. This linker was ligated into the HindIII site of pSL102, destroying the HindIII site and adding a unique BglII site resulting in the intermediate, pSL103.

The protein expression cassette (bp 6446-1330) containing the GAL1 promoter, fusion region, and ADH1 terminator sequence was amplified from pJG4-5 using the primers pJGF (5'-CGGATCCGCTCGGTACCCCATTATCTTAGCG-3') (SEQ ID NO:7) and pGJR (5'-CGGATCCGTGTGGAAGAACGATTAC-3') (SEQ ID NO:8), which added a BamHI site to each end of the cassette. The PCR product was digested and ligated into the BglII site of pSL103, destroying both the BamHI and BglII sites and yielding the intermediate, pSM101.

The plasmid pSM101 was then used as a template to amplify the 300 bp fusion tag described in the first paragraph with primers MCSF: (5'-CGCAAGCTTGGATCCGCGGCCGCCATGGAGCTCCCGGGTCGACGCGTCGAATCCGG TGCTCCTCCAAAAAAGAGAAAGG-3') (SEQ ID NO:9) and MCSR (5'-CGCAAGCTTTTAGGGAGAGGCATAATCTGGCACATCATAAGG-3') (SEQ ID NO:10), which added a HindIII site to each end of the tag and a unique multi-cloning site at the 5' end. The plasmid pSM101 was then digested with HindIII to remove the original fusion tag, and the PCR-generated tag was digested and ligated into the HindIII site resulting in the intermediate, pSMC101. Correct orientation of the new fusion tag was determined by PCR using the primers pJGF and MCSR.

The pSMC101 intermediate is the base vector for both pSMACK601 and pSMACK701, they deviate only in the choice of gene used for yeast replication. To generate pSMACK 601, the 2μ sequence was isolated from pJG4-5 by digestion with PstI and ligated into the PstI site of pSMC101.

TABLE 1

| pSMACK601 (6730 bp) | |
|---|---|
| Feature | Location |
| GAL1 minimal promoter | 1387-851 |
| Multiple Cloning Site | 850-811 |
| HA-NLS-B42 tag | 810-480 |
| ADH1 Terminator | 479-21 |
| 2μ yeast ori | 1414-3419 |
| LEU2 5' UTR | 4745-4633 |
| LEU2 coding sequence | 4632-3538 |
| LEU2 3' UTR | 3537-3431 |
| TonB terminator sequence | 4788-4825 |
| Ampicillin resistance gene | 4930-5789 |
| Repressor Of Primer (ROP) | 5790-5981 |
| T7 terminator sequence | 5992-6033 |
| ColE1 bacterial ori | 6458-6560 |
| T3 terminator sequence | 6654-6697 |

The creation of pSMACK701 (FIG. 4, TABLE 2, and SEQ ID NO:2) was a two-step process. First, the oligonucleotides PEPT (5'-GGATATCCAG-3') (SEQ ID NO:11) and PEPB (5'-CTGGATATCCTGCA-3') (SEQ ID NO:12) were annealed, digested with PstI and ligated into the PstI site of pSMC101 to create pSMC102. This construct now contains a unique PvuII site, flanked by EcoRV sites within the original PstI site. Next, the region containing both the CEN4 and ARS6 genes was removed form the plasmid pHis2 with PvuII and ligated into the PvuII site of pSMC102 to yield pSMACK701.

TABLE 2

| pSMACK701 (6471 bp) | |
|---|---|
| Feature | Location |
| GAL1 minimal promoter | 1387-851 |
| Multiple Cloning Site | 850-811 |
| HA-NLS-B42 tag | 810-480 |
| ADH1 Terminator | 479-21 |
| CEN4/ARS6 yeast ori | 1412-3161 |
| LEU2 5' UTR | 4486-4374 |
| LEU2 coding | 4373-3279 |
| LEU2 3' UTR | 3278-3172 |
| TonB terminator sequence | 4529-4566 |
| Ampicillin resistance gene | 4671-5530 |
| Repressor Of Primer (ROP) | 5531-5722 |
| T7 terminator sequence | 5733-5774 |
| ColE1 bacterial ori | 6199-6301 |
| T3 terminator sequence | 6395-6438 |

Figure 5:
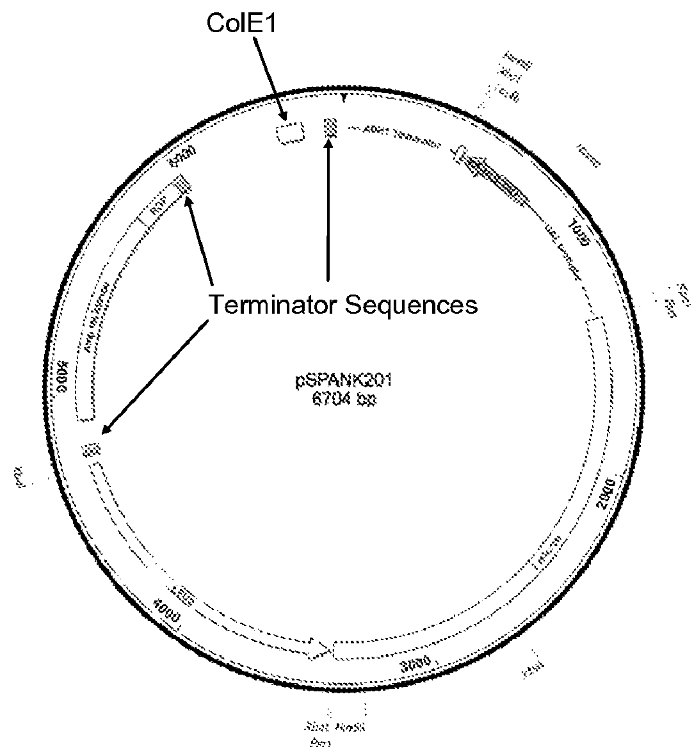
FIG. 5 is a map of bait vector pSPANK201, which uses the N-terminal fusion expression cassette and contains the 2μ high-copy number yeast origin of replication.
Figure 6:
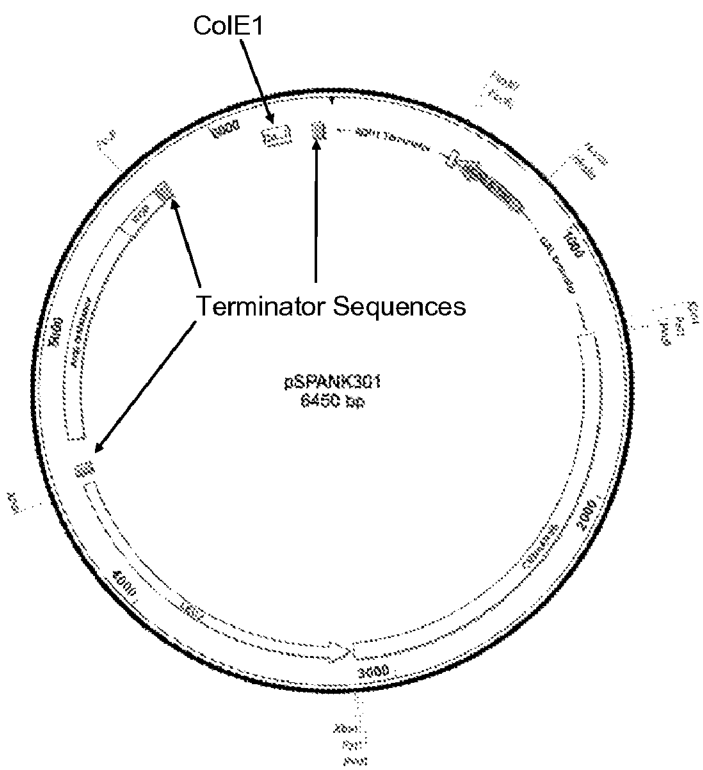
FIG. 6 is a map of bait vector pSPANK301, which uses the N-terminal fusion expression cassette and contains the CEN4/ARS6 low-copy number yeast origin of replication.

The plasmids pSPANK201 (FIG. 5, TABLE 3, and SEQ ID NO:13) and pSPANK301 (FIG. 6, TABLE 4, and SEQ ID NO:14) contain the original N-terminal fusion tag from pJG4-5 and are high copy and low copy, respectively. The pSM101 intermediate is the base vector for both plasmids.

To generate pSPANK201 (SEQ ID NO:13), the 2μ yeast origin of replication sequence was isolated from pJG4-5 by digestion with PstI and ligated into the PstI site of pSM101.

TABLE 3

| pSPANK201 (6704 bp) | |
|---|---|
| Feature | Location |
| GAL1 minimal promoter | 1361-825 |
| HA-NLS-B42 tag | 824-504 |
| Multiple Cloning Site | 503-480 |
| ADH1 Terminator | 479-21 |
| 2μ yeast ori | 1388-3393 |
| LEU2 5' UTR | 4719-4607 |
| LEU2 coding sequence | 4606-3512 |
| LEU2 3' UTR | 3511-3405 |
| TonB terminator sequence | 4762-4799 |
| Ampicillin resistance gene | 4904-5763 |
| Repressor Of Primer (ROP) | 5764-5955 |
| T7 terminator sequence | 5966-6007 |
| ColE1 bacterial ori | 6432-6534 |
| T3 terminator sequence | 6628-6671 |

The creation of pSPANK301 (SEQ ID NO:14) was again a two-step process. As with pSMACK701, the oligonucleotides PEPT and PEPB were annealed, digested with PstI and ligated into the PstI site of pSM101 to create pSM102. Next, the region containing both the CEN4 and ARS6 genes was removed form the plasmid pHis2 with PvuII and ligated into the PvuII site of pSM102 to yield pSPANK301.

TABLE 4

| pSPANK301 (6450 bp) | |
|---|---|
| Feature | Location |
| GAL1 minimal promoter | 1366-830 |
| HA-NLS-B42 tag | 829-504 |
| Multiple Cloning Site | 503-480 |
| ADH1 Terminator | 479-21 |
| CEN4/ARS6 yeast ori | 1391-3140 |
| LEU2 5' UTR | 4465-4353 |
| LEU2 coding sequence | 4352-3268 |
| LEU2 3' UTR | 3267-3151 |
| TonB terminator sequence | 4508-4545 |
| Ampicillin resistance gene | 4650-5509 |
| Repressor Of Primer (ROP) | 5510-5701 |
| T7 terminator sequence | 5712-5753 |
| ColE1 bacterial ori | 6178-6280 |
| T3 terminator sequence | 6374-6417 |

Figure 7:
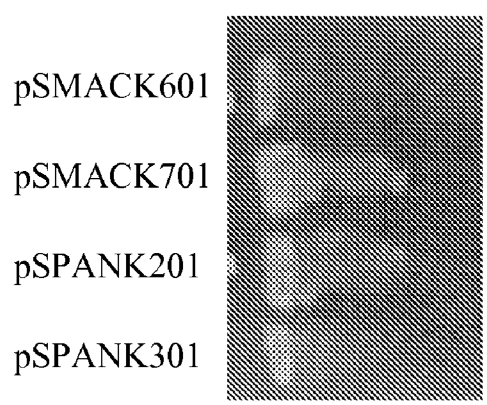
FIG. 7 is a photograph of yeast cells that have been transformed with pSMACK601, pSMACK701, pSPANK201, and pSPANK301, respectively, plated on synthetic complete media lacking leucine.

The four bait vectors (pSMACK601, pSMACK701, pSPANK201, and pSPANK301) were transformed by standard methods into the wild-type yeast strain W303, and plated on synthetic complete medium lacking leucine (Sc-L) to test the ability of the plasmid-borne LEU2 gene to express a functional protein, and to test the ability of the 2μ (pSMACK601; pSPANK201) or CEN4/ARS6 (pSMACK701; pSPANK301) elements to allow for replication of the plasmid in yeast (FIG. 7). FIG. 7 demonstrates that expression of a LEU2 gene can be induced in cells and confers a Leu$^+$ phenotype on cells. FIG. 7 also demonstrates the ability of the transformed yeast to grow on Sc-L whether the plasmid contains 2μ or CEN4/ARS6 elements.

Example 3

Creation of Reporter Vector pKAD202

Figure 8:
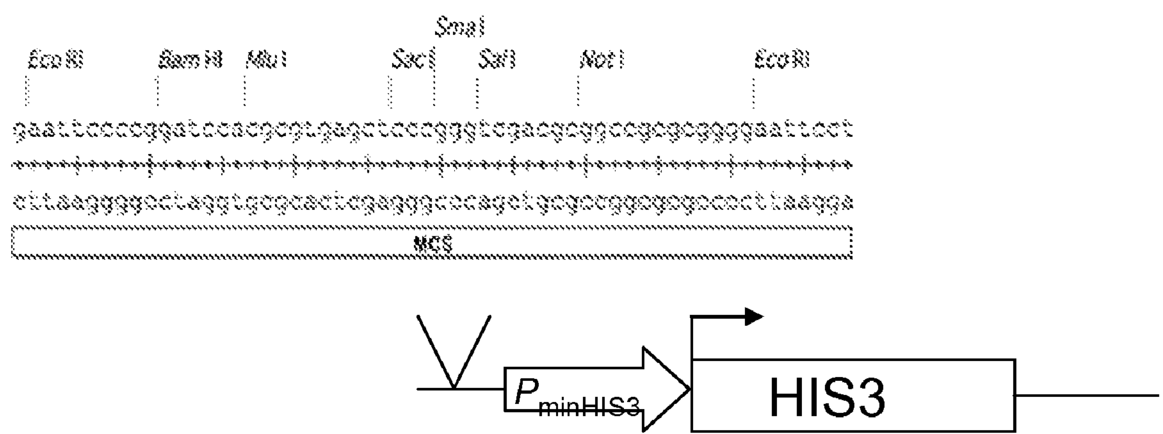
FIG. 8 is a schematic representation of the HIS3 reporter gene that operably linked to the minimal HIS3 promoter in reporter vector pKAD202 (SEQ ID NO: 15).
Figure 9:
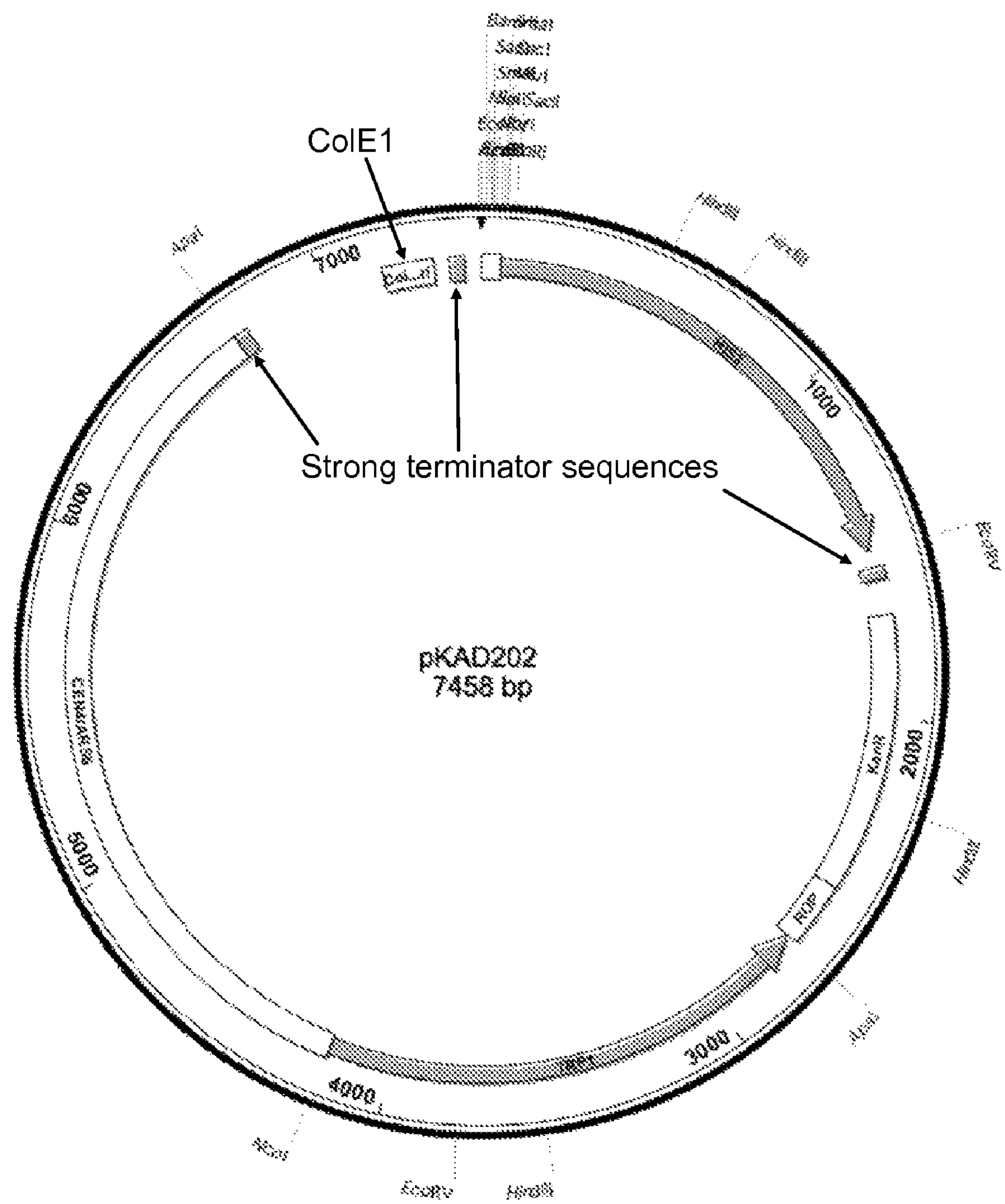
FIG. 9 is a map of reporter vector pKAD202, which contains the histidine reporter gene.

We designed a novel plasmid, pKAD202 (FIG. 9, TABLE 5, and SEQ ID NO:15), that contains a histidine reporter gene under the control of the minimal HIS3 promoter. Within the promoter region, a unique multiple cloning site allows for the insertion of genomic sequences or DNA sequences that contain known transcription factor binding sites for use as positive controls (FIG. 8). Plasmid pKAD202 also contains: (i) the TRP1 gene, which acts as a selectable marker in yeast; (ii) the Kanamycin gene and Col E1 bacterial origin of replication to allow for selection on plates containing kanamycin and propagation, respectively, in *E. coli*.; and (iii) the yeast ARS6 origin of replication and the CEN4 centromeric sequence (FIG. 9).

FIG. 8 shows a schematic representation of the HIS3 reporter gene that operably linked to the minimal HIS3 promoter in reporter vector pKAD202. This sequence also contains a novel multiple cloning site to allow the insertion of a genomic DNA library or sequences with known DNA-binding recognition sequences for use as positive controls. Finally, the strong termination sequences are indicated by the arrows and are as follows: 1) the TonB termination sequence is located immediately 3' of the HIS3 gene; 2) the T7 termination sequence is located immediately 3' of the CEN4/ARS6 sequence; and 3) the T3 termination sequence is located between the ColE1 bacterial origin of replication and the multiple cloning site. The features of reporter vector pKAD202 and their relative positions are shown in FIG. 9 and TABLE 5.

The vector was constructed by first amplifying the CEN4/ARS6 region from the plasmid pHR307a (Mastick et al., 1995; Accession #DQ012948) using NCOARSL primer 5'-ACTCACACCATGGCAGACATCTGT-GAATCGCTTCACGACCA-3' (SEQ ID NO:16) and APAARSR primer 5'-ACTCACAGGGCCCATGTGT-CAAAGGTTTTCACCGTCATCACCGA-3' (SEQ ID NO:17). These primers added NcoI (NCOARSL) and ApaI (APAARSR) ends to the PCR amplification product, flanking the CEN4/ARS6 region.

Next, the TRP1 gene was amplified from pHR307a using APATRPL primer 5'-ACTCACAGGGCCCTGGAATTAAT-TCCACATGTTAAATAGTGA-3' (SEQ ID NO:18) and NCOTRPR primer 5'-ACTGTGCCCTCCATGGAATTAAT-TCGGTCGA-3' (SEQ ID NO:19). These primers also added NcoI (NCOTRPR) and ApaI (APATRPL) ends to the PCR amplification product, flanking the TRP1 gene.

The CEN4/ARS6 and TRP1 fragments were digested with NcoI and ApaI restriction endonucleases, and a three-way ligation was performed with ApaI-digested pSMART®LCKan to generate an intermediate plasmid, denoted pKS101.

The HIS3 reporter cassette, which contains the minimal HIS3 promoter sequence, the HIS3 coding sequence, the HIS3 3'-untranslated region (UTR), and minimal HIS3 termination sequence, was amplified from the plasmid pHIS2 (BD Biosciences, Palo Alto, Calif.) using HISF primer 5'-GAATTCCCGGGGAGCTCA-3' (SEQ ID NO:20) and HISR primer 5'-CAATTGGTCGACGCTCTCCCTTA-3' (SEQ ID NO:21). These primers added an EcoRI site to the 5' end (HISF) of the amplified product and a MfeI site to the 3' (HISR) end of the amplified product, flanking the HIS3 reporter cassette. The PCR product was digested with EcoRI and ligated into the EcoRI site of pKS101, destroying the EcoRI site at the 3' end of the reporter cassette. This intermediate was denoted pKS102.

Figure 10:
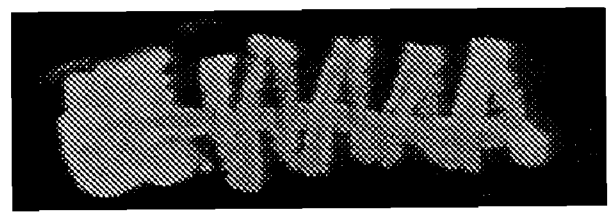
FIG. 10 is a photograph of yeast cells that have been transformed with pKAD202 and plated on synthetic complete media lacking tryptophan.

To create the novel multiple cloning site, we engineered MKC oligonucleotide 5'-AATTCCCCGGATCCACGCGT-GAGCTCCCGGGTCGACGCGGCCGCGCGGGG-3' (SEQ ID NO:22). This oligonucleotide was self-annealed to generate a double-stranded DNA fragment that contains EcoRI ends. The self-annealed fragment was cloned into the remaining EcoRI site of pKS102 to yield the plasmid pKAD202 (FIG. 9; SEQ ID NO:15). Reporter vector pKAD202 was transformed into the wild-type yeast strain W303 by standard methods, and plated on synthetic minimal media lacking tryptophan. The result is shown in FIG. 10, which is a photograph of yeast cells that have been transformed with pKAD202 and plated on synthetic complete media lacking tryptophan. FIG. 10 demonstrates that pKAD202 is functional in yeast; the TRP1 gene expresses a functional protein, and that the CEN4/ARS6 allows for replication of the plasmid.

TABLE 5 pKAD202 Reporter Vector

| Feature | Location |
|---|---|
| Multiple Cloning Site | 1-56 |
| Minimal HIS3 promoter | 57-201 |
| HIS3 coding sequence | 202-861 |
| HIS3 3' UTR | 862-1508 |
| TonB termination sequences | 1558-1595 |
| Kanamycin resistance gene | 1700-2515 |
| Repressor Of Primer (ROP) | 2516-2707 |
| TRP1 5' UTR | 4183-4078 |
| TRP1 coding sequence | 4077-3451 |
| TRP1 3' UTR | 3450-2711 |
| CEN4/ARS6 yeast ori | 4184-6702 |
| T7 termination sequences | 6704-6745 |
| ColE1 bacterial ori | 7170-7319 |
| T3 termination sequences | 7366-7409 |

Example 4

Creation of Pax3 Bait Vector Positive Controls

Pax3 was cloned into the four bait vectors with and without its transcriptional activation domain. Full length Pax3 was first cloned into pSMACK601 and pSMACK701 by PCR amplifying the entire Pax3 coding region using PAX3F primer 5'-CGGGATCCATGACCACGCTGGCCGGC-3' (SEQ ID NO:23) and PAX3R primer 5'-GCCGTCGACGTGCAATATCTGGCTTGAGATAATGAAAGGC-3' (SEQ ID NO:24). PCR amplification using these primers added a BamHI and SalI site to the 5' and 3' ends of Pax3, respectively. The PAX3R primer was also engineered to create a carboxyl-terminal fusion between Pax3 and the haemagglutinin (HA) epitope tag, yeast nuclear localization sequence, and the yeast transcriptional activation domain present in the pSMACK vectors. The resulting Pax3 product was digested with these restriction enzymes and directionally ligated into BamHI and SalI digested pSMACK601 and pSMACK701.

A truncated version of Pax3 was cloned in a similar fashion. The PAX3F primer (SEQ ID NO:23) and PAX3T primer 5'-CGGGTCGACCTGAATTCTGAGGTGAGACGCC-3' (SEQ ID NO:25) were used to PCR amplify a truncated coding sequence of Pax3 lacking the Pax3 transcriptional activation domain. The PAX3T primer was also engineered to create a carboxyl-terminal fusion between Pax3 and the haemagglutinin (HA) epitope tag, yeast nuclear localization sequence, and the yeast transcriptional activation domain present in the pSMACK vectors. The resulting PCR fragment was digested with BamHI and San and directionally ligated into the BamHI/SalI sites of pSMACK601 and pSMACK701.

Full length Pax3 was cloned into pSPANK201 and pSPANK301 using a two-step process. First, BKET oligonucleotide 5'-AATCCGGTACCG-3' (SEQ ID NO:26) and BKEB oligonucleotide 5'-GGATCCCGGTACCG-3' (SEQ ID NO:27) were annealed to generate a linker with BamHI and EcoRI ends and an internal KpnI site. This linker was ligated to the Pax3 BamHI/XhoI fragment containing the Pax3 coding region, resulting in a Pax3 DNA sequence with EcoRI and XhoI ends. The ligation reaction was then briefly digested with EcoRI to remove excess linkers and purified using a QIAGEN nucleotide removal kit. The resulting Pax3 insert was then ligated into the EcoRI/XhoI sites of pSPANK201 and pSPANK301.

Truncated Pax3 was cloned into pSPANK201 and pSPANK301 by ligating an EcoRI/XhoI fragment containing the truncated sequence into the EcoRI/XhoI sites of both vectors.

Example 5

Creation of FKHR Bait Vector Positive Controls

Full-length FKHR was cloned into pSMACK601 and pSMACK701 by amplifying the entire coding region using FKF primer 5'-CGGGATCCATGGCCGAAGCGCCCCAGGTG-3' (SEQ ID NO:28) and FKR primer 5'-GCCGTCGACGGCCTGACACCCAGCTATGTGTCG-3'(SEQ ID NO:29). PCR amplification using these primers added a BamHI and San site to the 5' and 3' ends of FKHR, respectively. The resulting FKHR product was digested and ligated into BamHI and SalI digested pSMACK601 and pSMACK701. Full length FKHR was cloned into pSPANK201 and pSPANK301 using a two-step process. First, oligonucleotides BKET (SEQ ID NO:26) and BKEB (SEQ ID NO:27) were annealed to generate a linker with BamHI and EcoRI ends and an internal KpnI site. This linker was ligated to a BamHI/XhoI fragment containing the FKHR coding region, resulting in a FKHR DNA sequence with EcoRI and XhoI ends. The ligation reaction was then briefly digested with EcoRI to remove excess linkers, and purified using a QIAGEN nucleotide removal kit. The resulting FKHR insert was then ligated into the EcoRI/XhoI sites of pSPANK201 and pSPANK301.

Example 6

Transformation of Bait Vector Constructs into Yeast

All of the constructs present in the pSMACK and pSPANK bait vectors were subsequently transformed into yeast strain W303 (MAT$\alpha$/MAT$\alpha$ADE2/ade2 CAN1/can1-100 CYH2/cyh2 his3-11,15/his3-11,15 LEU1/leu1-c LEU2/leu2-3,112 trp1-1:URA3:trp1-3'$\Delta$/trp1-1 ura3-1/ura3-1) using standard transformation methods (Ausubel, 1996). This yeast strain is auxotrophic for tryptophan, leucine, and histidine and will not grow in the absence of these nutrients or in the absence of the expression of the proper nutritional marker (e.g., the LEU2 gene present on the bait vectors). The resulting yeast transformants were grown on synthetic agar plates lacking leucine to select for yeast that were successfully transformed with the vectors.

Example 7

Creation of Reporter Vector Positive Controls—Pax3 Recognition Sites

Several in vivo targets of Pax3 have been identified including the anti-apoptotic protein BCL-$X_L$ (Margue et al., 2000); c-MET, a receptor tyrosine kinase involved in growth and motility signaling (Epstein et al., 1996); and Tyrosinase Related Protein-1 (TRP-1), a molecule involved in the genesis of pigmentation (Galibert et al., 1999). In addition, prior investigations have determined a consensus sequence for both the paired (5'-CGTCACGCTTA) (nucleotides 20-30 of SEQ ID NO: 30; nucleotides 17-27 of SEQ ID NO: 32; nucleotides 48-58 of SEQ ID NO: 32) and homeodomain (5'-ATTA) (nucleotides 12-15 of SEQ ID NO: 30; nucleotides 9-12 of SEQ ID NO: 32; nucleotides 40-43 of SEQ ID NO: 32) binding regions of Pax3 with the following configuration: 5'-ATTA($N_{4-5}$)CGTCACGCTTA (nucleotides 12-30 of SEQ ID NO: 30; nucleotides 9-27 of SEQ ID NO: 32; nucleotides 40-58 of SEQ ID NO: 32) (Epstein et al., 1994). Using this information, we generated several constructs (pSMACK601 (SEQ ID NO: 1), pSMACK701 (SEQ ID NO: 2), pSPANK201 (SEQ ID NO: 13), pSPANK301 (SEQ ID NO: 14), and pKAD202 (SEQ ID NO: 15)) to test the ability of Pax3 to activate the HIS3 reporter in the yeast PORE system.

The Pax3 reporter control that contains one copy of the Pax3 DNA recognition sequence was created by annealing oligonucleotide 1×S 5'-ATCCAGTGACGATTAGCACCGT-CACGCTTAGATATG-3' (SEQ ID NO:30) and oligonucleotide 1×AS 5'-TCGACATATCAAAGCGTGACGGT-GCTAATCGTCACTG-3' (SEQ ID NO:31). The resulting double stranded oligonucleotide has BamHI and SalI ends, and was ligated directly into BamHI/SalI digested pKAD202. The ligation mix was transformed into chemically competent DH5α cells and plated on LB plates containing 10 mg/L Kanamycin (LBKan) for selection. Kanamycin resistant colonies were screened for the presence of the appropriate insert by digestion with EcoRI. Positive clones were then maxi-prepped and transformed into yeast using standard techniques (Ausubel et al., 1996).

The Pax3 reporter control that contains two copies of the Pax3 DNA recognition sequence was created by annealing oligonucleotide 2×S 5'-CAGTGACGATTAGCACCGT-CACGCTTAGATATAGTGACGATTAGCAC-CGTCACGCTTA GATATA-3' (SEQ ID NO:32) and oligonucleotide 2×AS 5'-CGCGTATATCTAAGCGTGACGGT-GCTAATCGTCACTATATCTAAGAGT-GACGGTGCTAATCGT CACTGAGCT-3' (SEQ ID NO:33). The resulting double stranded oligonucleotide has XhoI and MluI ends and was ligated directly into MluI/SalI digested pKAD202. Positive transformants were selected as described above.

The Bcl-XL promoter region (SEQ ID NO:34) was PCR amplified from mouse genomic DNA using BclF primer 5'-CAGGATCCCTGCAGGGGGCTCCAGAAGG-3' (SEQ ID NO:35) and BclR primer 5'-GCACGCGTTCATGAAT-TGCGAAGCTTAGGACCT-3' (SEQ ID NO:36); the Msx2 promoter region (SEQ ID NO:37) was PCR amplified from mouse genomic DNA using primer Msx2F 5'-CGGGATC-CGATATCTCTACCTAAATTCCCTGCTGAGGAGCTC-3' (SEQ ID NO:38) and primer Msx2R 5'-CGACGCGT-GATATCTAACCGTGAAGCGTTGAGCACAGA-3' (SEQ ID NO:39); and the Trp1 promoter region (SEQ ID NO:40) was PCR amplified from mouse genomic DNA using primer TrpF 5'-CGGGATCCGATATCAAGCTTTTACCACT-GTGCCTTCTCC-3' (SEQ ID NO:41) and primer TrpR 5'-CGACGCGTGATATCAGCTGTTAATTGC-CCGAAGAG-3' (SEQ ID NO:42). All of these primers were engineered to contain a unique Bam HI site on the forward primer and a unique MluI site on the reverse primer. The resulting PCR-amplified products were TA-cloned by incubating 5 μl of the amplification product with 50 ng of the pCR®II linearized vector (Invitrogen, Carlsbad, Calif.) and 4.0 Weiss units of T4 DNA Ligase at 14° C. for a minimum of four hours. The pCR®II vector is a linearized vector with a one-base deoxythymidine overhang on the 3'-end of each vector strand. This vector is engineered to take advantage of the nontemplate-dependent activity of Taq polymerase that adds a single deoxyadenosine (A) to the 3'-ends of PCR products. The resulting ligated DNA was transformed into One Shot® Competent Cells (Invitrogen) and bacteria containing the ligated vector were selected on LB plates containing Ampicillin overnight at 37° C. Individual clones were picked, analyzed by restriction digest with EcoRV, and subsequently sequenced to confirm the PCR amplification process introduced no mutations. Finally, the regulatory elements were excised from pCR®II by BamHI/SalI digest and cloned into the same site of pKAD202.

Example 8

Creation of Reporter Vector Positive Controls—FKHR Recognition Sites

We have identified three classes of FKHR DNA recognition sites using a systematic evaluation of ligands by exponential enrichment (SELEX) (Bouvet, 2001). The three classes of FKHR sites are represented by FBS1 5'-GTAAA-CAACAACATGTTGAC-3' (SEQ ID NO:43), FBS2 5'-ACAACA($N_{11}$)ATAAACATGTTTAC-3' (SEQ ID NO:44), and FBS3 5'-TGTTTAC($N_7$)TGTTTAC-3' (SEQ ID NO:45), wherein "N" indicates any nucleotide A, T, C, or G, and the numeral subscript indicates the number of intervening nucleotides. These classes of sites differ in their affinity for FKHR with relative strength of binding as follows: FBS1>FBS2>FBS3. FBS1, FBS2, and FBS3, present in the pCR®II cloning vector, were released by EcoRI digest and subsequently ligated into EcoRI digested pKAD202.

Example 9

FKHR Regulatory Element Control

Sequence analysis of an individual clone isolated from a mouse genomic library present in the pSMART®LCKan vector (Lucigen Corp., Middleton, Wis.) fortuitously contained a copy of the FKHR DNA recognition site from class FBS3, listed above as Clone #14 (SEQ ID NO:46). A BLAST search of this fragment identified it as being part of intron 1 of the Gab-1 gene, a protein implicated in the regulation of myogenic differentiation (Vasyutina et al., 2005; Mood et al., 2006; and Fan et al., 2001). Taken together, these results suggested that this fragment would serve as a FKHR-dependent regulatory element and was subsequently used to clone into the pKAD202 vector for use as a positive control in the yeast PORE technique. As a negative control, a mouse genomic library clone that did not contain any of the classes of FKHR DNA recognition sequence was also used (Clone #14). Gab-1 was PCR amplified from the genomic DNA fragment present in pSMART LCKan using the SL1 (new) primer 5'-CGTGAAGGTGAGCCAGTGAGTTGATTG-CAGTCC-3' (SEQ ID NO:47) and SR2(new) primer 5'-CGT-GCCGATCAAGTCAAAAGCCTCCGGTCGG-3' (SEQ ID NO:48). The resulting PCR amplification product was TA-cloned into pCRII, as described above. The Gab-1 sequence was subsequently recovered from pCRII by EcoRI digest, and then cloned into the EcoRI site of pKAD202.

Example 10

Transformation of Reporter Vector Positive Controls into Yeast

Figure 11:
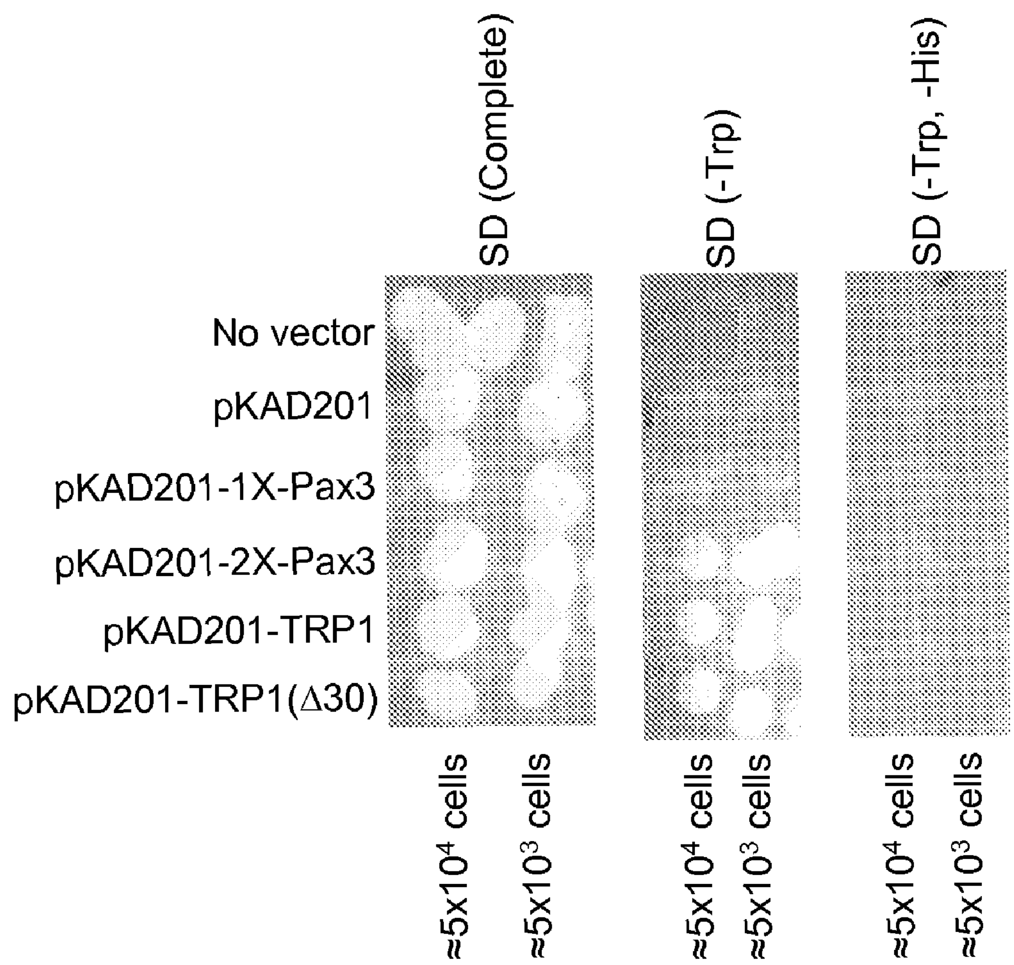
FIG. 11 shows yeast one-hybrid control DNA transformations. Yeast were transformed with the indicated pKAD202 constructs and plated onto galactose Synthetic Dropout (SD) media that contained all required amino acids (Complete) or SD media deficient for either tryptophan (-Trp) or tryptophan and histidine (-Trp, -His). The indicated number of yeast were grown for three days at 30° C.

As shown in FIG. 11, all of the positive controls—Pax3 and FKHR recognition sites, detailed above—present in pKAD202 were subsequently transformed into yeast strain W303 (MATα/MATαADE2/ade2 CAN1/can1-100 CYH2/cyh2 his3-11,15/his3-11,15 LEU1/leu1-c LEU2/leu2-3,112 trp1-1:URA3:trp1-3'Δ/trp1-1 ura3-1/ura3-1) using standard transformation methods (Ausubel et al., 1996). This yeast strain is auxotrophic for tryptophan, leucine, and histidine and will not grow in the absence of these nutrients or in the absence of the expression of the proper nutritional marker (i.e., the TRP1 gene present on pKAD202). The resulting yeast transformants were grown on synthetic agar plates lacking tryptophan to select for yeast that were successfully transformed with the vectors, and on synthetic agar plates lacking both tryptophan and histidine to demonstrate the lack of self-activation of the reporter constructs alone.

Figure 12:
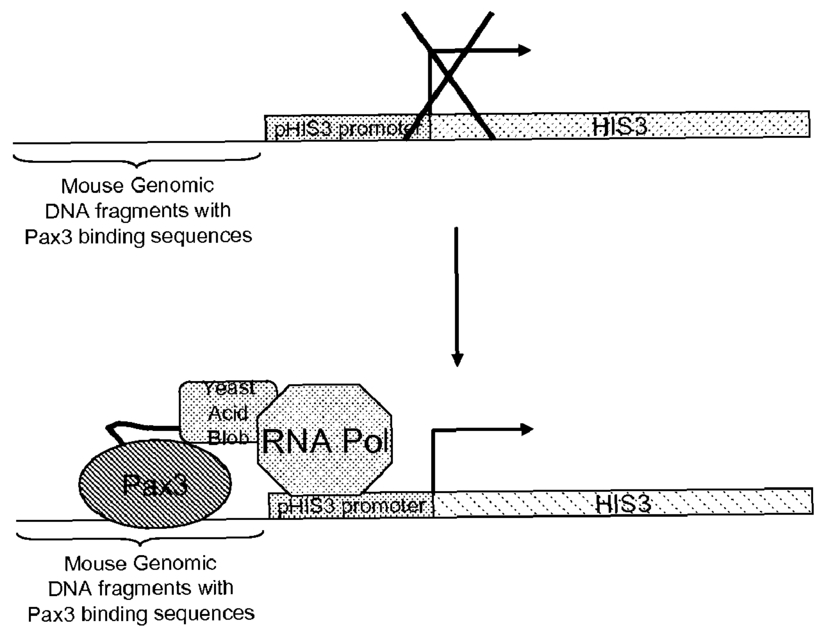
FIG. 12 is a schematic representation of the Yeast PORE technique according to the methods of the present invention, using Pax3 as a representative DNA-binding protein.

A schematic representation of the Yeast PORE technique according to the methods of the present invention, using Pax3 as a model DNA-binding protein, is shown in FIG. 12. In the absence of any DNA-binding protein to recognize and bind to the genomic DNA fragment inserted upstream of the HIS3 promoter, there is no transcription or expression of histidine (as represented schematically in FIG. 12 and as shown in practice in FIG. 11). In the presence of a DNA-binding protein (e.g., Pax3 expressed as a fusion protein with the yeast acid blob domain), RNA polymerase is recruited to the protein-DNA complex, transcription of HIS3 is initiated, and survival on plates lacking histidine is enabled. For the sake of simplicity, FIG. 12 does not show all elements (including, among other things, the vector backbone, the epitope tag, and the NLS) of the technique.

Figure 13:
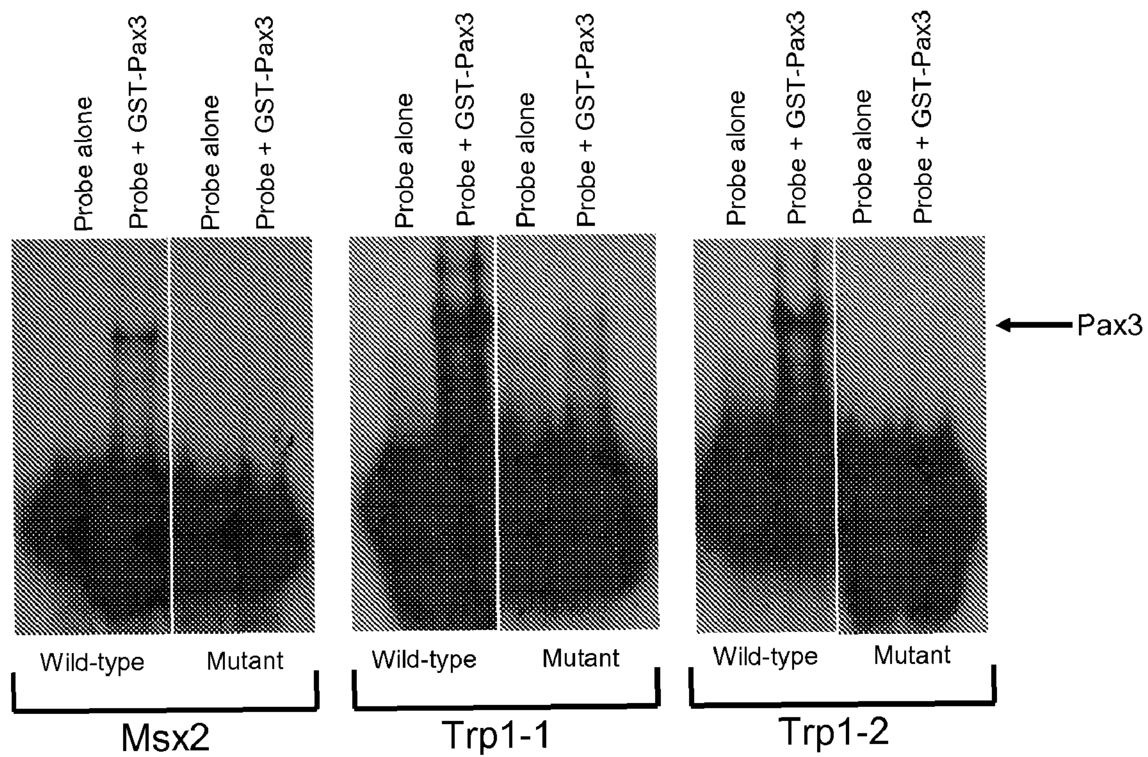
FIG. 13 shows the results of an electrophoretic mobility shift assay (EMSA) demonstrating the binding of Pax3 to physiologically relevant promoter elements, which include Msx2, Trp-1 with one Pax3 binding site (Trp1-1) and Trp-1 with two Pax3 binding sites (Trp1-2). The arrow indicates the mobility of the Pax3:DNA complex.

As shown in FIG. 13, Pax3 binds to physiologically relevant promoter elements, which include Msx2, Trp-1 with one Pax3 binding site (Trp1-1), and Trp-1 with two Pax3 binding sites (Trp1-2). We cloned the TRP-1 and Msx2 gene promoter sequences into the pSMART®HC-Kan vector as described above. These promoter elements were demonstrated to be bound and regulated by Pax3, and therefore serve as positive controls for the methods of the present invention. We used site directed mutagenesis to clone deletion mutants of these three promoter elements into pSMART®HC-Kan. These mutants have specifically removed the Pax3 recognition sequences and will serve as the negative control for the methods of the present invention. To confirm that these promoter regions interact with Pax3 in vitro, approximately 80-100 by surrounding the region of the identified Pax3 binding sites was PCR amplified using [α-$^{32}$P]-dCTP. These radioactively amplified fragments were then tested for binding in an electrophoretic mobility shift assay, as shown in FIG. 13. We observed a specific shift of the probe in the presence of GST-Pax3 for Msx2 and for both of the identified Pax3 binding sites present in TRP1 (FIG. 13, arrow). This shift was not observed in the presence of the mutated promoter elements, demonstrating that bacterially expressed and purified Pax3 can bind to its DNA recognition sequence in vitro when this sequence is present in a larger promoter context.

Figure 14:
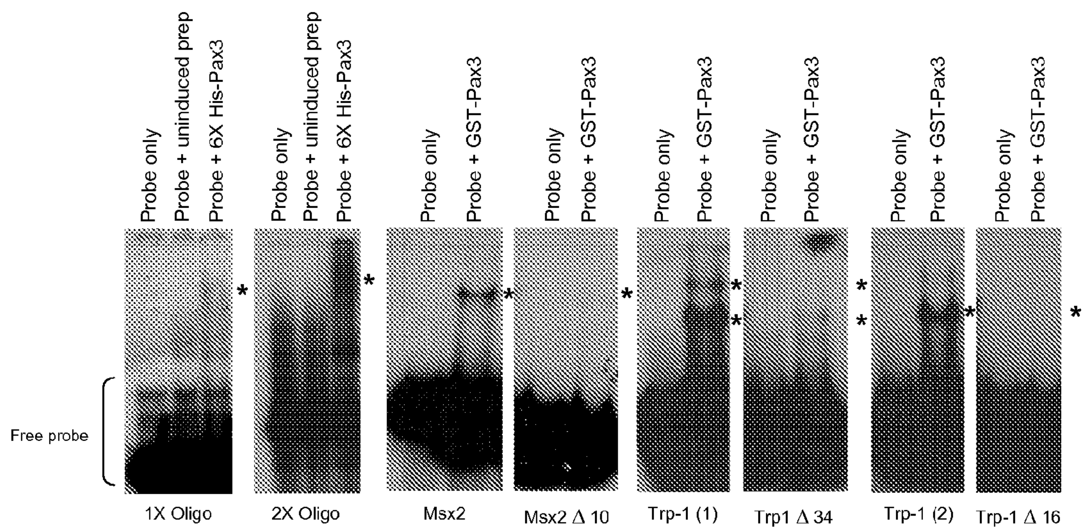
FIG. 14 shows the results of an EMSA demonstrating that Pax3 binds oligonucleotide sequences (1× Oligo and 2× Oligo), regions of thePax3-regulated mouse promoter elements Msx2, Trp-1 (1), which contains one Pax3 recognition sequence and Trp-1 (2), which contains two Pax3 recognition sequences), and the respective promoter deletion mutants that have had the Pax3 recognition sequence specifically deleted (Msx2Δ10, Trp-1 Δ34, and Trp-1 Δ16) cloned into pKAD202. Probes were generated by end-labeling double-stranded oligonucleotides with $\gamma^{32}$P-dATP or PCR labeling with $\alpha^{32}$P-dGTP. Probes were incubated with or without 6×-His-Pax3 or GST-PAX3 at 25° C., and the complexes were resolved on a 6% Tris-glycine polyacrylamide gel. The free probes are designated by the bottom bracket, and the shifted Pax3:DNA complex by the asterisk to the right of each gel.

Furthermore, as shown in FIG. 14, Pax3 binds oligonucleotide sequences (1× Oligo and 2× Oligo), regions of thePax3-regulated mouse promoter elements Msx2, Trp-1 (1), which contains one Pax3 recognition sequence and Trp-1 (2), which contains two Pax3 recognition sequences), but not the respective promoter deletion mutants that have had the Pax3 recognition sequence specifically deleted (Msx2Δ10, Trp-1 Δ 34, and Trp-1 Δ 16) cloned into pKAD202. Probes were generated by end labeling double-stranded oligonucleotides with γ$^{32}$P-dATP or PCR labeling with α$^{32}$P-dGTP. Probes were incubated with or without 6×-His-Pax3 or GST-PAX3 at 25° C., and the complexes were resolved on a 6% Tris-glycine polyacrylamide gel. The location of the free probes is indicated by the bracket at left, and the shifted Pax3:DNA complexes by the asterisks to the right of each gel.

Example 11

Empty Bait Vector does not Activate pKAD202 HIS Reporter

Figure 15:
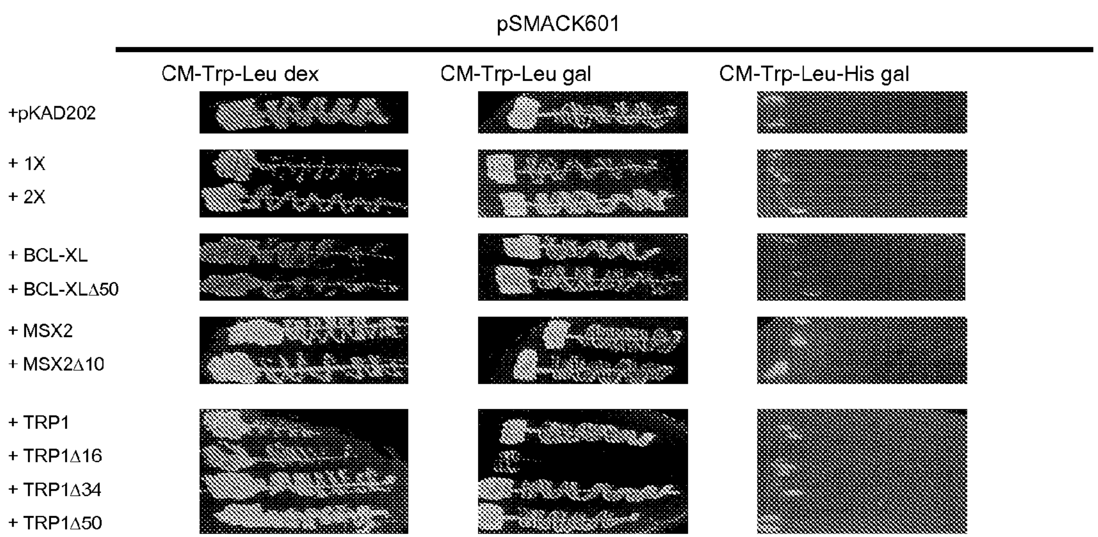
FIG. 15 shows that the pSMACK601 vector does not activate the HIS reporter in the presence of the pKAD202 constructs. The pSMACK601 plasmid was co-transformed with all pKAD202 constructs into wild type yeast (W303) and transformants selected on CM-Trp-Leu plates containing dextrose. Positive transformants were then plated on CM-Trp-Leu plates containing dextrose (left) or galactose (middle). Activation of the H is reporter was tested by plating on CM-Trp-Leu-His plates containing galactose (right). The pKAD202 constructs used are listed on the left.

As shown in FIG. 15, empty pSMACK601 bait vector does not activate the HIS reporter of pKAD202 in the presence of the pKAD202 constructs listed on the left. The pSMACK601 plasmid was co-transformed with all pKAD202 constructs indicated into wild type yeast (W303), and transformants plated on synthetic complete media lacking tryptophan and leucine (Sc-Trp-Leu) but containing dextrose. Positive transformants were then plated on Sc-Trp-Leu plates containing dextrose (left) or galactose (middle). Activation of the HIS reporter was tested by plating on Sc-Trp-Leu plates also lacking histidine (-His) but containing galactose (right). This demonstrates that, in the absence of a DNA-binding protein (which would be encoded by a sequence inserted into the bait vector's multiple cloning site), the HIS reporter of the pKAD202 vector is not activated, as expected.

Example 12

Preparation of Mouse Genomic DNA Library

Mouse genomic DNA is sheared by sonication, end-repaired with a DNA Terminator®End Repair Kit (Lucigen, Middleton, Wis.), and separated on a 1% agarose gel. Plasmid vector pKAD202 is restriction digested with San, and end-repaired with a DNA Terminator® End Repair Kit (Lucigen, Middleton, Wis.) to create blunt ends. Genomic DNA fragments between 0.5-2.0 kb are gel purified and cloned into the prepared blunt cloning site of pKAD202. The resulting ligated DNA is electroporated into ElectroMAX DH10B *E. coli* cells (Invitrogen, Carlsbad, Calif.). An aliquot of the transformed bacteria is plated onto Luria broth (LB) agar plates containing kanamycin, and the remainder of the cells are saved as a frozen glycerol stock. A representative sample of colonies (about twenty) are selected and cultured separately in liquid LB medium containing kanamycin. Plasmid DNA is isolated from each liquid culture, subjected to restriction digest with SmaI, and separated on a 1% agarose gel to determine insert frequency and size. This analysis demonstrates the prevalence of clones containing genomic DNA inserts between 0.65-2.0 kb. Sequencing of the inserts with SL1 forward primer 5'-CAGTCCAGTTACGCTGGAGTC-3' (SEQ ID NO:49) demonstrates whether the clones isolated are derived from unique pieces of genomic DNA. A genomic library created in this manner contains approximately 3 to 8×10$^{6}$ independent clones, with DNA inserts between 0.65-2.0 kb, providing an approximate 1.7- to 4.5-fold over-representation of the entire mouse genome. It will be appreciated by those skilled in the art that the above technique, as applied to mouse genomic DNA, is equally applicable to other mammalian genomic DNA, including human genomic DNA.

Example 13

Expansion of a Genomic DNA Library

A mouse genomic library, prepared as described above, is expanded by plating the glycerol stock of bacteria (after determining the library titer as described above), reserved from above and containing the library, onto 24.5×24.5 cm LB agar plates containing kanamycin, and incubating the plates at 37° C. overnight. The colony density is limited to approximately 20,000 colonies per plate to avoid overcrowding. The resulting colonies are scraped from the plate, and the DNA is isolated using a Qiagen Maxiprep kit (Qiagen, Valencia, Calif.). The resulting DNA is aliquoted and stored at −80° C.

Example 14

Yeast Transformation

Yeast were transformed using an established protocol (Ausubel et al., 1996). Briefly, yeast strain W303 (MATα/MATαADE2/ade2 CAN1/can1-100 CYH2/cyh2 his3-11,15/his3-11,15 LEU1/leu1-c LEU2/leu2-3,112 trp1-1:URA3: trp1-3'Δ/trp1-1 ura3-1/ura3-1; ATCC #200060) or K2346 (MATa ade2-1 ade3 trp1-1 leu2-3,112 his3-11,15 ura3 ssd1; ATCC #200864) were grown in YPD media (6 g yeast extract, 12 g peptone, 12 g glucose, 60 mg adenine hemisulphate, 600 mL $H_2O$, pH 7.0) overnight at 30° C. with continual shaking. Alternatively, to create bait-plus-library vector double-transformants, yeast previously transformed with one of the bait vectors were grown in Synthetic Dropout (SD) media (see Ausubel) lacking tryptophan (Trp). The next morning the yeast culture was diluted to an optical density ($OD_{600}$) of 0.10 (late lag phase of growth) and incubated at 30° C. with continual shaking until the cells reach mid-log phase growth ($OD_{600}$=0.4–0.6). The cells were harvested by centrifugation for five minutes at 1500×g and washed two times by resuspending the cell pellet in 30 ml of water and centrifuging again as just described. After the second water wash, the cell pellet was resuspended in 1.5 ml of TE buffer (10 mM Tris-Cl to pH7.5, plus 1 mM ethylenediaminetetraacetic acid) containing 0.1M lithium acetate (LiOAc). Into a separate 1.5 ml eppendorf tube was added 1 μg of the desired yeast vector, and 50 μg of high-quality sheared salmon sperm carrier DNA. 50 μl of the yeast/TE/LiOAc solution was then added to the vector/carrier DNA solution. 300 μl of sterile 40% PEG 4000 in TE buffer (pH7.5) containing 0.1M LiOAc was then added, the sample mixed thoroughly by inversion, and then incubated at 30° C. for 30 minutes. After incubation, DMSO was added to 10% final volume (approximately 40 μl) and mixed thoroughly by inversion. This mixture was then heat shocked at 42° C. for 10 minutes. The heat shocked yeast were then plated on SD media lacking amino acid(s) required for the selection process (e.g., lacking Trp if transformation was performed with a bait vector alone; lacking leucine (Leu) if transformation was performed with a library vector; and lacking both Leu and Trp if transformation was performed with both bait and library vectors).

Example 15

Figure 16:
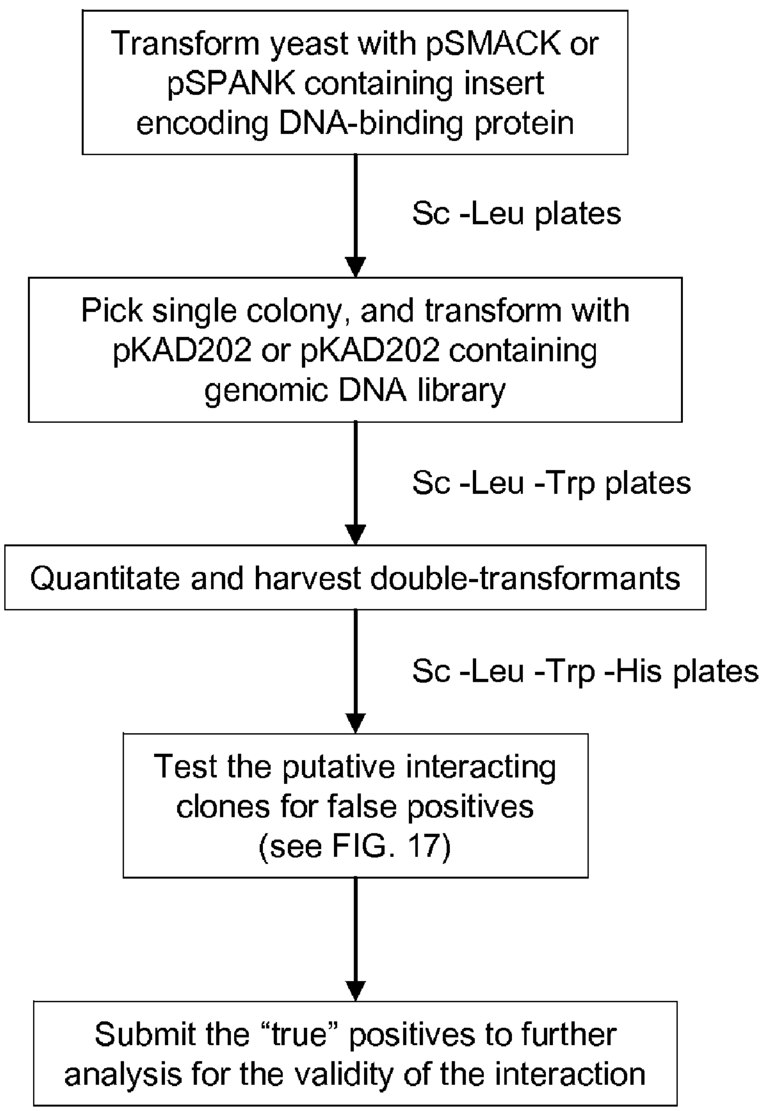
FIG. 16 is a schematic diagram of the yeast one-hybrid screen according to the methods of the present invention.

Yeast PORE Genomic Screen, Including Elimination or Reduction of False Positives Wild-type yeast are first transformed using standard techniques with the chosen bait vector carrying the coding sequence of the DNA-binding protein to be studied (FIG. 16). Positive transformants are selected by plating on synthetic minimal media lacking leucine. One colony is then selected and used to propagate a new batch of cells, which are then transformed with a pool of reporter vectors (pKAD202) containing the randomly generated genomic DNA library. Serial dilutions of yeast containing both the bait and library vectors are then plated on synthetic minimal dextrose media lacking leucine and tryptophan to calculate the transformation efficiency and ensure accurate representation of the genomic library. Once the optimal number of transformations necessary to saturate the library is calculated, the double transformation is repeated, and the yeast are plated on synthetic minimal galactose media lacking leucine, tryptophan, and histidine. The resulting colonies are then replica-plated onto plates containing an optimal concentration of 3-aminotriazole ("3-AT," where the optimal concentration is determined in control experiments). Only those colonies that grow under these conditions will be considered putative interacting clones, or "positive" (FIG. 16).

Figure 17:
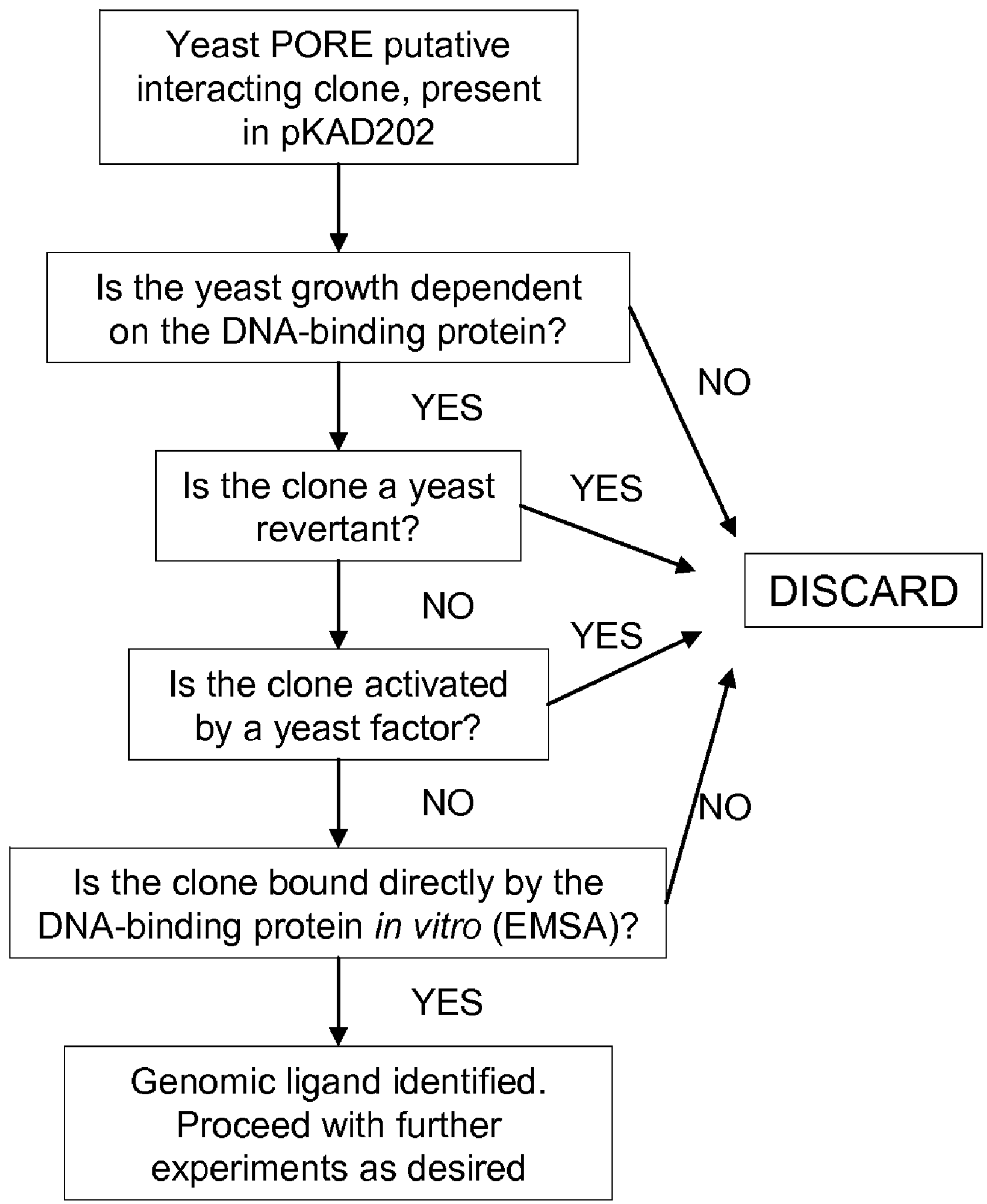
FIG. 17 is a schematic diagram of the tests designed to eliminate false positive clones, and is to be read in conjunction with FIG. 16.

The putative positives identified in the first round of the Yeast PORE process are further tested according to the steps below, and represented schematically in FIG. 17, to reduce or eliminate the number of false positives.

First, activation of the HIS3 reporter, resulting from the binding of Pax3 or FKHR to genomic DNA cloned into pKAD202, is confirmed. This is accomplished by re-plating the putative positive clones onto galactose plates lacking leucine, tyrptophan, and histidine, and supplemented with the optimal 3-AT concentration, to verify the results form the first screen.

Second, the positive colonies are streaked onto dextrose plates lacking leucine, tryptophan, and histidine. As the expression of Pax3 and FKHR is under the control of a galactose-inducible promoter, the positive clones should not grow on the dextrose plates. The pKAD202 vector is then isolated from the colonies that pass the second round of screening. Briefly, the positive colonies are grown in minimal media, and standard techniques are used to isolate plasmid DNA from the yeast. The resulting plasmid DNA—the pKAD202 vector containing a genomic DNA ligand—is transformed into *E. coli*, which are selected for by growth on LB plates containing kanamycin.

Third, the isolated reporter vector is re-transformed into yeast alone (i.e., without any other vector). The single transformants are tested using the initial screening process (FIG. 16), as described, but with the addition of leucine to all media. The pKAD202 vector should not rescue the cells grown under the selective conditions (lacking histidine, but containing 3-AT). Finally, the isolated reporter vector is then co-transformed with the bait vector into a fresh growth of yeast, and the double transformants are tested as described previously (FIG. 16). This test confirms that the original ability to grow in the absence of histidine did not result from a yeast reversion.

Clones that pass all rounds of false-positive tests are considered true positive interactions. The multiple cloning site of the pKAD202 vector from each positive colony is then sequenced to identify the genomic sequence bound by the transcription factor.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A method for determining whether a test protein interacts with a test nucleic acid sequence, the method comprising:

(a) providing a population of competent cells wherein a plurality of the cells of said population contain:
   (i) a reporter gene operably linked to a test nucleic acid sequence;
   (ii) a fusion gene, wherein the fusion gene expresses a hybrid protein, said hybrid protein comprising a test protein covalently bonded to a gene activating moiety; and (b) detecting expression of the reporter gene as a measure of the ability of the test protein to interact with the test nucleic acid sequence, wherein the test nucleic acid sequence in the population of competent cells is derived from genomic DNA library, wherein the genomic DNA library is a stable genomic DNA library;

wherein the reporter gene and test nucleic acid sequence are located on a plasmid; and wherein the plasmid is pKAD202.

2. A method for determining whether a test protein interacts with a test nucleic acid sequence, the method comprising:

(a) providing a population of competent cells wherein a plurality of the cells of said population contain:
   (i) a reporter gene operably linked to a test nucleic acid sequence;
   (ii) a fusion gene, wherein the fusion gene expresses a hybrid protein, said hybrid protein comprising a test protein covalently bonded to a gene activating moiety; and (b) detecting expression of the reporter gene as a measure of the ability of the test protein to interact with the test nucleic acid sequence, wherein the test nucleic acid sequence in the population of competent cells is derived from a genomic DNA library, wherein the genomic DNA library is a stable genomic DNA library;

wherein the reporter gene and test nucleic acid sequence are located on a first plasmid;

wherein the fusion gene is located on a second plasmid; and wherein the second plasmid is selected from one of pSMACK701 or pSPANK301.

3. A method for determining whether a test protein interacts with a test nucleic acid sequence, the method comprising:

(a) providing a population of competent cells wherein a plurality of the cells of said population contain:

(i) a reporter gene operably linked to a test nucleic acid sequence;

(ii) a fusion gene, wherein the fusion gene expresses a hybrid protein, said hybrid protein comprising a test protein covalently bonded to a gene activating moiety; and (b) detecting expression of the reporter gene as a measure of the ability of the test protein to interact with the test nucleic acid sequence, wherein the test nucleic acid sequence in the population of competent cells is derived from a genomic DNA library, wherein the genomic DNA library is a stable genomic DNA library;

wherein the reporter gene and test nucleic acid sequence are located on a first plasmid;

wherein the fusion gene is located on a second plasmid; and wherein the second plasmid is selected from one of pSMACK601 or pSPANK201.

* * * * *

SEQUENCE LISTING

<160> NUMBER OF SEQ ID NOS: 49

<210> SEQ ID NO 1
<211> LENGTH: 6730
<212> TYPE: DNA
<213> ORGANISM: Artificial
<220> FEATURE:
<223> OTHER INFORMATION: Circular plasmid DNA

<400> SEQUENCE: 1

```
gaatgatatc aaagctgcga ccgtgtggaa gaacgattac aacaggtgtt gtcctctgag     60
gacataaaat acacaccgag attcatcaac tcattgctgg agttagcata tctacaattg    120
ggtgaaatgg ggagcgattt gcaggcattt gctcggcatg ccggtagagg tgtggtcaat    180
aagagcgacc tcatgctata cctgagaaag caacctgacc tacaggaaag agttactcaa    240
gaacaagaat tttcgtttta aaacctaaga gtcactttaa aatttgtata cacttatttt    300
ttttataact tatttaataa taaaaatcat aaatcataag aaattcgctt atttagaagt    360
gtcaacaacg tatctaccaa cgatttgacc cttttccatc ttttcgtaaa tttctggcaa    420
ggtagacaag ccgacaacct tgattggaga cttgaccaaa cctctggcga agaagtccaa    480
agcttttagg gagaggcata atctggcaca tcataagggt aggaggcatc tccactcagc    540
aagaggctgg tatcgttaac atccgcttca atttcatgaa aaccattcga tttcagccag    600
tcaggctgga tcggcggccc ggcgtgaaga atggttttcg gcgtcatgcc cggcaccacg    660
ttaatcgcct gatccgccat ttccatcggc atctcctgtc cggtgcgcag gtagtcgata    720
aactgctcaa tgatggcatt gcactcctcg atatctttat tgataccagc tacctttctc    780
ttcttttttg gaggagcacc ggattcgacg cgtcgacccg ggagctccat ggcggccgcg    840
gatccaagct taattcctcc ttgacgttaa agtatagagg tatattaaca atttttttgtt   900
gatactttta ttacatttga ataagaagta atacaaaccg aaaatgttga aagtattagt    960
taaagtggtt atgcagtttt tgcatttata tatctgttaa tagatcaaaa atcatcgctt   1020
cgctgattaa ttaccccaga aataaggcta aaaaactaat cgcattatca tcctatggtt   1080
gttaatttga ttcgttcatt tgaaggtttg tggggccagg ttactgccaa tttttcctct   1140
tcataaccat aaaagctagt attgtagaat ctttattgtt cggagcagtg cggcgcgagg   1200
cacatctgcg tttcaggaac gcgaccggtg aagacgagga cgcacggagg agagtcttcc   1260
ttcggagggc tgtcacccgc tcggcggctt ctaatccgta cttcaatata gcaatgagca   1320
gttaagcgta ttactgaaag ttccaaagag aaggtttttt taggctaaga taatggggta   1380
ccggatcatc tcgcagcttg aattgcgcct gcagtgcagc ttctcaatga tattcgaata   1440
cgctttgagg agatacagcc taatatccga caaactgttt tacagattta cgatcgtact   1500
tgttacccat cattgaattt tgaacatccg aacctgggag ttttccctga aacagatagt   1560
atatttgaac ctgtataata atatatagtc tagcgcttta cggaagacaa tgtatgtatt   1620
tcggttcctg gagaaactat tgcatctatt gcataggtaa tcttgcacgt cgcatccccg   1680
gttcattttc tgcgtttcca tcttgcactt caatagcata tctttgttaa cgaagcatct   1740
gtgcttcatt ttgtagaaca aaaatgcaac gcgagagcgc taatttttca aacaaagaat   1800
ctgagctgca tttttacaga acagaaatgc aacgcgaaag cgctatttta ccaacgaaga   1860
atctgtgctt catttttgta aaacaaaaat gcaacgcgag agcgctaatt tttcaaacaa   1920
agaatctgag ctgcattttt acagaacaga aatgcaacgc gagagcgcta ttttaccaac   1980
```

```
aaagaatcta tacttctttt ttgttctaca aaaatgcatc ccgagagcgc tatttttcta   2040
acaaagcatc ttagattact ttttttctcc tttgtgcgct ctataatgca gtctcttgat   2100
aactttttgc actgtaggtc cgttaaggtt agaagaaggc tactttggtg tctatttcct   2160
cttccataaa aaaagcctga ctccacttcc cgcgtttact gattactagc gaagctgcgg   2220
gtgcattttt tcaagataaa ggcatccccg attatattct ataccgatgt ggattgcgca   2280
tactttgtga acagaaagtg atagcgttga tgattcttca ttggtcagaa aattatgaac   2340
ggtttcttct attttgtctc tatatactac gtataggaaa tgtttacatt ttcgtattgt   2400
tttcgattca ctctatgaat agttcttact acaatttttt tgtctaaaga gtaatactag   2460
agataaacat aaaaaatgta gaggtcgagt ttagatgcaa gttcaaggag cgaaaggtgg   2520
atgggtaggt tatataggga tatagcacag agatatatag caaagagata cttttgagca   2580
atgtttgtgg aagcggtatt cgcaatattt tagtagctcg ttacagtccg gtgcgttttt   2640
ggtttttga aagtgcgtct tcagagcgct tttggttttc aaaagcgctc tgaagttcct   2700
atactttcta gagaatagga acttcggaat aggaacttca aagcgtttcc gaaaacgagc   2760
gcttccgaaa atgcaacgcg agctgcgcac atacagctca ctgttcacgt cgcacctata   2820
tctgcgtgtt gcctgtatat atatatacat gagaagaacg gcatagtgcg tgtttatgct   2880
taaatgcgta cttatatgcg tctatttatg taggatgaaa ggtagtctag tacctcctgt   2940
gatattatcc cattccatgc ggggtatcgt atgcttcctt cagcactacc ctttagctgt   3000
tctatatgct gccactcctc aattggatta gtctcatcct tcaatgctat catttccttt   3060
gatattggat catatgcata gtaccgagaa actagtgcga agtagtgatc aggtattgct   3120
gttatctgat gagtatacgt tgtcctggcc acggcagaag cacgcttatc gctccaattt   3180
cccacaacat tagtcaactc cgttaggccc ttcattgaaa gaaatgaggt catcaaatgt   3240
cttccaatgt gagattttgg gccatttttt atagcaaaga ttgaataagg cgcatttttc   3300
ttcaaagctt tattgtacga tctgactaag ttatctttta ataattggta ttcctgttta   3360
ttgcttgaag aattgccggt cctatttact cgttttagga ctggttcaga attgctgcag   3420
gcgcaattct ctagacctac cctatgaaca tattccattt tgtaatttcg tgtcgtttct   3480
attatgaatt tcatttataa agtttatgta caaatatcat aaaaaaagag aatcttttta   3540
agcaaggatt ttcttaactt cttcggcgac agcatcaccg acttcggtgg tactgttgga   3600
accacctaaa tcaccagttc tgatacctgc atccaaaacc tttttaactg catcttcaat   3660
ggccttacct tcttcaggca agttcaatga caatttcaac atcattgcag cagacaagat   3720
agtggcgata gggttgacct tattctttgg caaatctgga gcagaaccgt ggcatggttc   3780
gtacaaacca aatgcggtgt tcttgtctgg caaagaggcc aaggacgcag atggcaacaa   3840
acccaaggaa cctgggataa cggaggcttc atcggagatg atatcaccaa acatgttgct   3900
ggtgattata ataccattta ggtgggttgg gttcttaact aggatcatgg cggcagaatc   3960
aatcaattga tgttgaacct tcaatgtagg aaattcgttc ttgatggttt cctccacagt   4020
ttttctccat aatcttgaag aggccaaaac attagcttta tccaaggacc aaataggcaa   4080
tggtggctca tgttgtaggg ccatgaaagc ggccattctt gtgattcttt gcacttctgg   4140
aacggtgtat tgttcactat cccaagcgac accatcacca tcgtcttcct ttctcttacc   4200
aaagtaaata cctcccacta attctctgac aacaacgaag tcagtacctt tagcaaattg   4260
tggcttgatt ggagataagt ctaaaagaga gtcggatgca aagttacatg gtcttaagtt   4320
ggcgtacaat tgaagttctt tacggatttt tagtaaacct tgttcaggtc taacactacc   4380
```

-continued

```
tgtaccccat ttaggaccac ccacagcacc taacaaaacg gcatcaacct tcttggaggc   4440
ttccagcgcc tcatctggaa gtgggacacc tgtagcgtcg atagcagcac caccaattaa   4500
atgattttcg aaatcgaact tgacattgga acgaacatca gaaatagctt taagaacctt   4560
aatggcttcg gctgtgattt cttgaccaac gtggtcacct ggcaaaacga cgatcttctt   4620
aggggcagac attagaatgg tatatccttg aaatatatat atatattgct gaaatgtaaa   4680
aggtaagaaa agttagaaag taagacgatt gctaaccacc tattggaaaa aacaataggt   4740
ctagatatcg ctcaatactg accatttaaa tcatacctga cctccatagc agaaagtcaa   4800
aagcctccga ccggaggctt ttgacttgat cggcacgtaa gaggttccaa ctttcaccat   4860
aatgaaataa gatcactacc gggcgtattt tttgagttat cgagattttc aggagctaag   4920
gaagctaaaa tgagtattca acatttccgt gtcgccctta ttcccttttt tgcggcattt   4980
tgccttcctg tttttgctca cccagaaacg ctggtgaaag taaaagatgc tgaagatcag   5040
ttgggtgcac gagtgggtta catcgaactg gatctcaaca gcggtaagat ccttgagagt   5100
ttacgccccg aagaacgttt tccaatgatg agcactttta aagttctgct atgtggcgcg   5160
gtattatccc gtattgacgc cgggcaagag caactcggtc gccgcataca ctattctcag   5220
aatgacttgg ttgagtactc accagtcaca gaaaagcatc tcacggatgg catgacagta   5280
agagaattat gcagtgctgc cataaccatg agtgataaca ctgcggccaa cttacttctg   5340
gcaacgatcg gaggaccgaa ggagctaacc gcttttttgc acaacatggg ggatcatgta   5400
actcgccttg atcgttggga accggagctg aatgaagcca taccaaacga cgagcgtgac   5460
accacgatgc ctgtagcaat ggcaacaacg ttgcgcaaac tattaactgg cgaactactt   5520
actctagctt cccggcaaca attaatagac tggatggagg cggataaagt tgcaggatca   5580
cttctgcgct cggccctccc ggctggctgg tttattgctg ataaatctgg agccggtgag   5640
cgtgggtctc gcggtatcat tgcagcactg gggccagatg gtaagccctc ccgcatcgta   5700
gttatctaca cgacggggag tcaggcaact atggatgaac gaaatagaca gatcgctgag   5760
ataggtgcct cactgattaa gcattggtaa gtgaccaaac aggaaaaaac cgcccttaac   5820
atggcccgct ttatcagaag ccagacatta acgcttctgg agaaactcaa cgagctggac   5880
gcggatgaac aggcagacat ctgtgaatcg cttcacgacc acgctgatga gctttaccgc   5940
agctgcctcg cgcgtttcgg tgatgacggt gaaaacctct gatgagggcc caaatgtaat   6000
cacctggctc accttcgggt gggcctttct gcgttgctgg cgtttttcca taggctccgc   6060
ccccctgacg agcatcacaa aaatcgatgc tcaagtcaga ggtggcgaaa cccgacagga   6120
ctataaagat accaggcgtt tccccctgga agctccctcg tgcgctctcc tgttccgacc   6180
ctgccgctta ccggatacct gtccgccttt ctcccttcgg gaagcgtggc gctttctcat   6240
agctcacgct gtaggtatct cagttcggtg taggtcgttc gctccaagct gggctgtgtg   6300
cacgaacccc ccgttcagcc cgaccgctgc gccttatccg gtaactatcg tcttgagtcc   6360
aacccggtaa gacacgactt atcgccactg gcagcagcca ctggtaacag gattagcaga   6420
gcgaggtatg taggcggtgc tacagagttc ttgaagtggt ggcctaacta cggctacact   6480
agaagaacag tatttggtat ctgcgctctg ctgaagccag ttacctcgga aaaagagttg   6540
gtagctcttg atccggcaaa caaaccaccg ctggtagcgg tggttttttt gtttgcaagc   6600
agcagattac gcgcagaaaa aaaggatctc aagaagatcc tttgatcttt taccgaagaa   6660
aggcccaccc gtgaaggtga gccagtgagt tgattgcagt ccagttacgc tggagtctga   6720
ggctcgtcct                                                          6730
```

<210> SEQ ID NO 2
<211> LENGTH: 6471
<212> TYPE: DNA
<213> ORGANISM: Artificial
<220> FEATURE:
<223> OTHER INFORMATION: Circular plasmid DNA

<400> SEQUENCE: 2

```
gaatgatatc aaagctgcga ccgtgtggaa gaacgattac aacaggtgtt gtcctctgag     60

gacataaaat acacaccgag attcatcaac tcattgctgg agttagcata tctacaattg    120

ggtgaaatgg ggagcgattt gcaggcattt gctcggcatg ccggtagagg tgtggtcaat    180

aagagcgacc tcatgctata cctgagaaag caacctgacc tacaggaaag agttactcaa    240

gaacaagaat tttcgtttta aaacctaaga gtcactttaa aatttgtata cacttatttt    300

ttttataact tatttaataa taaaaatcat aaatcataag aaattcgctt atttagaagt    360

gtcaacaacg tatctaccaa cgatttgacc cttttccatc ttttcgtaaa tttctggcaa    420

ggtagacaag ccgacaacct tgattggaga cttgaccaaa cctctggcga agaagtccaa    480

agcttttagg gagaggcata atctggcaca tcataagggt aggaggcatc tccactcagc    540

aagaggctgg tatcgttaac atccgcttca atttcatgaa aaccattcga tttcagccag    600

tcaggctgga tcggcggccc ggcgtgaaga atggttttcg gcgtcatgcc cggcaccacg    660

ttaatcgcct gatccgccat ttccatcggc atctcctgtc cggtgcgcag gtagtcgata    720

aactgctcaa tgatggcatt gcactcctcg atatctttat tgataccagc tacctttctc    780

ttcttttttg gaggagcacc ggattcgacg cgtcgacccg ggagctccat ggcggccgcg    840

gatccaagct taattcctcc ttgacgttaa agtatagagg tatattaaca atttttttgtt    900

gatactttta ttacatttga ataagaagta atacaaaccg aaaatgttga aagtattagt    960

taaagtggtt atgcagtttt tgcatttata tatctgttaa tagatcaaaa atcatcgctt   1020

cgctgattaa ttaccccaga aataaggcta aaaaactaat cgcattatca tcctatggtt   1080

gttaatttga ttcgttcatt tgaaggtttg tggggccagg ttactgccaa tttttcctct   1140

tcataaccat aaaagctagt attgtagaat ctttattgtt cggagcagtg cggcgcgagg   1200

cacatctgcg tttcaggaac gcgaccggtg aagacgagga cgcacggagg agagtcttcc   1260

ttcggagggc tgtcacccgc tcggcggctt ctaatccgta cttcaatata gcaatgagca   1320

gttaagcgta ttactgaaag ttccaaagag aaggtttttt taggctaaga taatggggta   1380

ccggatcatc tcgcagcttg aattgcgcct gctgcaggat atccagctgc gcaaggaacg   1440

cccgtcgtgg ccagccacga tagccgcgct gcctcgtctt gcagttcatt cagggcaccg   1500

gacaggtcgg tcttgacaaa aagaaccggg cgcccctgcg ctgacagccg gaacacggcg   1560

gcatcagagc agccgattgt ctgttgtgcc cagtcatagc cgaatagcct ctccacccaa   1620

gcggccggag aacctgcgtg caatccatct tgttcaatca tactcttcct tttcaatat    1680

tattgaagca tttatcaggg ttattgtctc atgagcggat acatatttga atgtatttag   1740

aaaaataaac aaataggggt tccgcgcaca tttccccgaa aagtgccacc tgcggacgga   1800

tcgcttgcct gtaacttaca cgcgcctcgt atcttttaat gatggaataa tttgggaatt   1860

tactctgtgt ttatttattt ttatgttttg tatttggatt ttagaaagta aataaagagt   1920

agaagagtta cggaatgaag aaaaaaaaat aaacaaaggt ttaaaaaatt tcaacaaaaa   1980

gcgtacttta catatatatt tattagacaa gaaaagcaga ttaaatagat atacattcga   2040

ttaacgataa gtaaaatgta aaatcacagg attttcgtgt gtggtcttct acacagacaa   2100
```

```
gatgaaacaa ttcggcatta atacctgaga gcaggaagag caagataaaa ggtagtattt   2160
gttggcgatc cccctagagt cttttacatc ttcggaaaac aaaaactatt ttttctttaa   2220
tttctttttt tactttctat ttttaattta tatatttata ttaaaaaatt taaattataa   2280
ttatttttat agcacgtgat gaaaaggacc gacgtctaag aaaccattat tatcatgaca   2340
ttaacctata aaaataggcg tatcacgagg ccctttcgtc tcgcgcgttt cggtgatgac   2400
ggtgaaaacc tctgacacat gcagctcccg gagacggtca cagcttgtct gtaagcggat   2460
gccgggagca gacaagcccg tcagggcgcg tcagcgggtg ttggcgggtg tcggggctgg   2520
cttaactatg cggcatcaga gcagattgta ctgagagtgc accatatgcg gtgtgaaata   2580
ccgcacagat gcgtaaggag aaaataccgc atcaggaaat tgtaaacgtt aatattttgt   2640
taaaattcgc gttaaatttt tgttaaatca gctcattttt taaccaatag gccgaaatcg   2700
gcaaaatccc ttataaatca aaagaataga ccgagatagg gttgagtgtt gttccagttt   2760
ggaacaagag tccactatta aagaacgtgg actccaacgt caaagggcga aaaaccgtct   2820
atcagggcga tggcccacta cgtgaaccat caccctaatc aagttttttg gggtcgaggt   2880
gccgtaaagc actaaatcgg aaccctaaag ggagcccccg atttagagct tgacggggaa   2940
agccggcgaa cgtggcgaga aaggaaggga agaaagcgaa aggagcgggc gctagggcgc   3000
tggcaagtgt agcggtcacg ctgcgcgtaa ccaccacacc cgccgcgctt aatgcgccgc   3060
tacagggcgc gtcgcgccat tcgccattca ggctgcgcaa ctgttgggaa gggcgatcgg   3120
tgcgggcctc ttcgctatta cgccagctgg atatcctgca ggcgcaattc tctagaccta   3180
ccctatgaac atattccatt ttgtaatttc gtgtcgtttc tattatgaat ttcatttata   3240
aagtttatgt acaaatatca taaaaaaaga gaatcttttt aagcaaggat tttcttaact   3300
tcttcggcga cagcatcacc gacttcggtg gtactgttgg aaccacctaa atcaccagtt   3360
ctgatacctg catccaaaac ctttttaact gcatcttcaa tggccttacc ttcttcaggc   3420
aagttcaatg acaatttcaa catcattgca gcagacaaga tagtggcgat agggttgacc   3480
ttattctttg gcaaatctgg agcagaaccg tggcatggtt cgtacaaacc aaatgcggtg   3540
ttcttgtctg gcaaagaggc caaggacgca gatggcaaca aacccaagga acctgggata   3600
acggaggctt catcggagat gatatcacca aacatgttgc tggtgattat aataccattt   3660
aggtgggttg ggttcttaac taggatcatg gcggcagaat caatcaattg atgttgaacc   3720
ttcaatgtag gaaattcgtt cttgatggtt tcctccacag tttttctcca taatcttgaa   3780
gaggccaaaa cattagcttt atccaaggac caaataggca atggtggctc atgttgtagg   3840
gccatgaaag cggccattct tgtgattctt tgcacttctg gaacggtgta ttgttcacta   3900
tcccaagcga caccatcacc atcgtcttcc tttctcttac caaagtaaat acctcccact   3960
aattctctga caacaacgaa gtcagtacct ttagcaaatt gtggcttgat tggagataag   4020
tctaaaagag agtcggatgc aaagttacat ggtcttaagt tggcgtacaa ttgaagttct   4080
ttacggattt ttagtaaacc ttgttcaggt ctaacactac ctgtacccca tttaggacca   4140
cccacagcac ctaacaaaac ggcatcaacc ttcttggagg cttccagcgc ctcatctgga   4200
agtgggacac ctgtagcgtc gatagcagca ccaccaatta aatgattttc gaaatcgaac   4260
ttgacattgg aacgaacatc agaaatagct ttaagaacct taatggcttc ggctgtgatt   4320
tcttgaccaa cgtggtcacc tggcaaaacg acgatcttct taggggcaga cattagaatg   4380
gtatatcctt gaaatatata tatatattgc tgaaatgtaa aaggtaagaa aagttagaaa   4440
gtaagacgat tgctaaccac ctattggaaa aaacaatagg tctagatatc gctcaatact   4500
```

```
gaccatttaa atcatacctg acctccatag cagaaagtca aaagcctccg accggaggct   4560

tttgacttga tcggcacgta agaggttcca actttcacca taatgaaata agatcactac   4620

cgggcgtatt ttttgagtta tcgagatttt caggagctaa ggaagctaaa atgagtattc   4680

aacatttccg tgtcgccctt attccctttt ttgcggcatt ttgccttcct gtttttgctc   4740

acccagaaac gctggtgaaa gtaaaagatg ctgaagatca gttgggtgca cgagtgggtt   4800

acatcgaact ggatctcaac agcggtaaga tccttgagag tttacgcccc gaagaacgtt   4860

ttccaatgat gagcactttt aaagttctgc tatgtggcgc ggtattatcc cgtattgacg   4920

ccgggcaaga gcaactcggt cgccgcatac actattctca gaatgacttg gttgagtact   4980

caccagtcac agaaaagcat ctcacggatg gcatgacagt aagagaatta tgcagtgctg   5040

ccataaccat gagtgataac actgcggcca acttacttct ggcaacgatc ggaggaccga   5100

aggagctaac cgcttttttg cacaacatgg gggatcatgt aactcgcctt gatcgttggg   5160

aaccggagct gaatgaagcc ataccaaacg acgagcgtga caccacgatg cctgtagcaa   5220

tggcaacaac gttgcgcaaa ctattaactg gcgaactact tactctagct tcccggcaac   5280

aattaataga ctggatggag gcggataaag ttgcaggatc acttctgcgc tcggcccttcc   5340

cggctggctg gtttattgct gataaatctg gagccggtga gcgtgggtct cgcggtatca   5400

ttgcagcact ggggccagat ggtaagccct cccgcatcgt agttatctac acgacgggga   5460

gtcaggcaac tatggatgaa cgaaatagac agatcgctga gataggtgcc tcactgatta   5520

agcattggta agtgaccaaa caggaaaaaa ccgcccttaa catggcccgc tttatcagaa   5580

gccagacatt aacgcttctg gagaaactca acgagctgga cgcggatgaa caggcagaca   5640

tctgtgaatc gcttcacgac cacgctgatg agctttaccg cagctgcctc gcgcgtttcg   5700

gtgatgacgg tgaaaacctc tgatgagggc ccaaatgtaa tcacctggct caccttcggg   5760

tgggcctttc tgcgttgctg gcgtttttcc ataggctccg ccccccctgac gagcatcaca   5820

aaaatcgatg ctcaagtcag aggtggcgaa acccgacagg actataaaga taccaggcgt   5880

ttccccctgg aagctccctc gtgcgctctc ctgttccgac cctgccgctt accggatacc   5940

tgtccgcctt tctcccttcg ggaagcgtgg cgctttctca tagctcacgc tgtaggtatc   6000

tcagttcggt gtaggtcgtt cgctccaagc tgggctgtgt gcacgaaccc cccgttcagc   6060

ccgaccgctg cgccttatcc ggtaactatc gtcttgagtc caacccggta agacacgact   6120

tatcgccact ggcagcagcc actggtaaca ggattagcag agcgaggtat gtaggcggtg   6180

ctacagagtt cttgaagtgg tggcctaact acggctacac tagaagaaca gtatttggta   6240

tctgcgctct gctgaagcca gttacctcgg aaaaagagtt ggtagctctt gatccggcaa   6300

acaaaccacc gctggtagcg gtggtttttt tgtttgcaag cagcagatta cgcgcagaaa   6360

aaaaggatct caagaagatc ctttgatttt ctaccgaaga aaggcccacc cgtgaaggtg   6420

agccagtgag ttgattgcag tccagttacg ctggagtctg aggctcgtcc t             6471
```

<210> SEQ ID NO 3
<211> LENGTH: 29
<212> TYPE: DNA
<213> ORGANISM: Artificial
<220> FEATURE:
<223> OTHER INFORMATION: oligonucleotide primer

<400> SEQUENCE: 3

```
cgtctagacc taccctatga acatattcc                                     29
```

<210> SEQ ID NO 4

<211> LENGTH: 29
<212> TYPE: DNA
<213> ORGANISM: Artificial
<220> FEATURE:
<223> OTHER INFORMATION: oligonucleotide primer

<400> SEQUENCE: 4
cgtctagacc tattgttttt tccaatagg 29

<210> SEQ ID NO 5
<211> LENGTH: 12
<212> TYPE: DNA
<213> ORGANISM: Artificial
<220> FEATURE:
<223> OTHER INFORMATION: oligonucleotide linker

<400> SEQUENCE: 5
aattgctgca gc 12

<210> SEQ ID NO 6
<211> LENGTH: 16
<212> TYPE: DNA
<213> ORGANISM: Artificial
<220> FEATURE:
<223> OTHER INFORMATION: oligonucleotide linker

<400> SEQUENCE: 6
agctgcgaga tctcgc 16

<210> SEQ ID NO 7
<211> LENGTH: 31
<212> TYPE: DNA
<213> ORGANISM: Artificial
<220> FEATURE:
<223> OTHER INFORMATION: oligonucleotide primer

<400> SEQUENCE: 7
cggatccgct cggtacccca ttatcttagc g 31

<210> SEQ ID NO 8
<211> LENGTH: 25
<212> TYPE: DNA
<213> ORGANISM: Artificial
<220> FEATURE:
<223> OTHER INFORMATION: oligonucleotide primer

<400> SEQUENCE: 8
cggatccgtg tggaagaacg attac 25

<210> SEQ ID NO 9
<211> LENGTH: 79
<212> TYPE: DNA
<213> ORGANISM: artificial
<220> FEATURE:
<223> OTHER INFORMATION: oligonucleotide primer

<400> SEQUENCE: 9
cgcaagcttg gatccgcggc cgccatggag ctcccgggtc gacgcgtcga atccggtgct 60
cctccaaaaa agagaaagg 79

<210> SEQ ID NO 10
<211> LENGTH: 42
<212> TYPE: DNA
<213> ORGANISM: Artificial
<220> FEATURE:
<223> OTHER INFORMATION: olilgonucleotide primer

<400> SEQUENCE: 10
cgcaagcttt tagggagagg cataatctgg cacatcataa gg 42

<210> SEQ ID NO 11
<211> LENGTH: 10
<212> TYPE: DNA
<213> ORGANISM: artificial
<220> FEATURE:
<223> OTHER INFORMATION: oligonucleotide

<400> SEQUENCE: 11
ggatatccag 10

<210> SEQ ID NO 12
<211> LENGTH: 14
<212> TYPE: DNA
<213> ORGANISM: Artificial
<220> FEATURE:
<223> OTHER INFORMATION: oligonucleotide

<400> SEQUENCE: 12
ctggatatcc tgca 14

<210> SEQ ID NO 13
<211> LENGTH: 6704
<212> TYPE: DNA
<213> ORGANISM: Artificial
<220> FEATURE:
<223> OTHER INFORMATION: Circular plasmid DNA

<400> SEQUENCE: 13
gaatgatatc aaagctgcga ccgtgtggaa gaacgattac aacaggtgtt gtcctctgag 60
gacataaaat acacaccgag attcatcaac tcattgctgg agttagcata tctacaattg 120
ggtgaaatgg ggagcgattt gcaggcattt gctcggcatg ccggtagagg tgtggtcaat 180
aagagcgacc tcatgctata cctgagaaag caacctgacc tacaggaaag agttactcaa 240
gaacaagaat tttcgtttta aaacctaaga gtcactttaa aatttgtata cacttatttt 300
ttttataact tatttaataa taaaaatcat aaatcataag aaattcgctt atttagaagt 360
gtcaacaacg tatctaccaa cgatttgacc cttttccatc ttttcgtaaa tttctggcaa 420
ggtagacaag ccgacaacct tgattggaga cttgaccaaa cctctggcga agaagtccaa 480
agcttctcga gtcggccgaa ttcgggagag gcataatctg gcacatcata agggtaggag 540
gcatctccac tcagcaagag gctggtatcg ttaacatccg cttcaatttc atgaaaacca 600
ttcgatttca gccagtcagg ctggatcggc ggcccggcgt gaagaatggt tttcggcgtc 660
atgcccggca ccacgttaat cgcctgatcc gccatttcca tcggcatctc ctgtccggtg 720
cgcaggtagt cgataaactg ctcaatgatg gcattgcact cctcgatatc tttattgata 780
ccagctacct ttctcttctt ttttggagga gcacccataa gctttaattc ctccttgacg 840
ttaaagtata gaggtatatt aacaattttt tgttgatact tttattacat ttgaataaga 900
agtaatacaa accgaaaatg ttgaaagtat tagttaaagt ggttatgcag tttttgcatt 960
tatatatctg ttaatagatc aaaaatcatc gcttcgctga ttaattaccc cagaaataag 1020
gctaaaaaac taatcgcatt atcatcctat ggttgttaat ttgattcgtt catttgaagg 1080
tttgtggggc caggttactg ccaatttttc ctcttcataa ccataaaagc tagtattgta 1140
gaatctttat tgttcggagc agtgcggcgc gaggcacatc tgcgtttcag gaacgcgacc 1200
ggtgaagacg aggacgcacg gaggagagtc ttccttcgga gggctgtcac ccgctcggcg 1260

-continued

```
gcttctaatc cgtacttcaa tatagcaatg agcagttaag cgtattactg aaagttccaa   1320
agagaaggtt tttttaggct aagataatgg ggtaccggat catctcgcag cttgaattgc   1380
gcctgcagtg cagcttctca atgatattcg aatacgcttt gaggagatac agcctaatat   1440
ccgacaaact gttttacaga tttacgatcg tacttgttac ccatcattga attttgaaca   1500
tccgaacctg ggagttttcc ctgaaacaga tagtatattt gaacctgtat aataatatat   1560
agtctagcgc tttacggaag acaatgtatg tatttcggtt cctggagaaa ctattgcatc   1620
tattgcatag gtaatcttgc acgtcgcatc cccggttcat tttctgcgtt tccatcttgc   1680
acttcaatag catatctttg ttaacgaagc atctgtgctt cattttgtag aacaaaaatg   1740
caacgcgaga gcgctaattt ttcaaacaaa gaatctgagc tgcattttta cagaacagaa   1800
atgcaacgcg aaagcgctat tttaccaacg aagaatctgt gcttcatttt tgtaaaacaa   1860
aaatgcaacg cgagagcgct aatttttcaa acaaagaatc tgagctgcat tttacagaa   1920
cagaaatgca acgcgagagc gctattttac caacaaagaa tctatacttc tttttgttc   1980
tacaaaaatg catcccgaga gcgctatttt tctaacaaag catcttagat tacttttttt   2040
ctcctttgtg cgctctataa tgcagtctct tgataacttt ttgcactgta ggtccgttaa   2100
ggttagaaga aggctacttt ggtgtctatt ttctcttcca taaaaaaagc ctgactccac   2160
ttcccgcgtt tactgattac tagcgaagct gcgggtgcat tttttcaaga taaaggcatc   2220
cccgattata ttctataccg atgtggattg cgcatacttt gtgaacagaa agtgatagcg   2280
ttgatgattc ttcattggtc agaaaattat gaacggtttc ttctattttg tctctatata   2340
ctacgtatag gaaatgttta cattttcgta ttgttttcga ttcactctat gaatagttct   2400
tactacaatt tttttgtcta aagagtaata ctagagataa acataaaaaa tgtagaggtc   2460
gagtttagat gcaagttcaa ggagcgaaag gtggatgggt aggttatata gggatatagc   2520
acagagatat atagcaaaga gatacttttg agcaatgttt gtggaagcgg tattcgcaat   2580
attttagtag ctcgttacag tccggtgcgt ttttggtttt ttgaaagtgc gtcttcagag   2640
cgcttttggt tttcaaaagc gctctgaagt tcctatactt tctagagaat aggaacttcg   2700
gaataggaac ttcaaagcgt ttccgaaaac gagcgcttcc gaaaatgcaa cgcgagctgc   2760
gcacatacag ctcactgttc acgtcgcacc tatatctgcg tgttgcctgt atatatatat   2820
acatgagaag aacggcatag tgcgtgttta tgcttaaatg cgtacttata tgcgtctatt   2880
tatgtaggat gaaaggtagt ctagtacctc ctgtgatatt atcccattcc atgcggggta   2940
tcgtatgctt ccttcagcac taccctttag ctgttctata tgctgccact cctcaattgg   3000
attagtctca tccttcaatg ctatcatttc ctttgatatt ggatcatatg catagtaccg   3060
agaaactagt gcgaagtagt gatcaggtat tgctgttatc tgatgagtat acgttgtcct   3120
ggccacggca gaagcacgct tatcgctcca atttcccaca acattagtca actccgttag   3180
gcccttcatt gaaagaaatg aggtcatcaa atgtcttcca atgtgagatt ttgggccatt   3240
ttttatagca aagattgaat aaggcgcatt tttcttcaaa gctttattgt acgatctgac   3300
taagttatct tttaataatt ggtattcctg tttattgctt gaagaattgc cggtcctatt   3360
tactcgtttt aggactggtt cagaattgct gcaggcgcaa ttctctagac ctaccctatg   3420
aacatattcc attttgtaat ttcgtgtcgt ttctattatg aatttcattt ataaagttta   3480
tgtacaaata tcataaaaaa agagaatctt tttaagcaag gattttctta acttcttcgg   3540
cgacagcatc accgacttcg gtggtactgt tggaaccacc taaatcacca gttctgatac   3600
ctgcatccaa aacctttta actgcatctt caatggcctt accttcttca ggcaagttca   3660
```

-continued

```
atgacaattt caacatcatt gcagcagaca agatagtggc gatagggttg accttattct   3720
ttggcaaatc tggagcagaa ccgtggcatg gttcgtacaa accaaatgcg gtgttcttgt   3780
ctggcaaaga ggccaaggac gcagatggca acaaacccaa ggaacctggg ataacggagg   3840
cttcatcgga gatgatatca ccaaacatgt tgctggtgat tataatacca tttaggtggg   3900
ttgggttctt aactaggatc atggcggcag aatcaatcaa ttgatgttga accttcaatg   3960
taggaaattc gttcttgatg gtttcctcca cagtttttct ccataatctt gaagaggcca   4020
aaacattagc tttatccaag gaccaaatag gcaatggtgg ctcatgttgt agggccatga   4080
aagcggccat tcttgtgatt ctttgcactt ctggaacggt gtattgttca ctatcccaag   4140
cgacaccatc accatcgtct tcctttctct taccaaagta aatacctccc actaattctc   4200
tgacaacaac gaagtcagta cctttagcaa attgtggctt gattggagat aagtctaaaa   4260
gagagtcgga tgcaaagtta catggtctta agttggcgta caattgaagt tctttacgga   4320
tttttagtaa accttgttca ggtctaacac tacctgtacc ccatttagga ccacccacag   4380
cacctaacaa aacggcatca accttcttgg aggcttccag cgcctcatct ggaagtggga   4440
cacctgtagc gtcgatagca gcaccaccaa ttaaatgatt ttcgaaatcg aacttgacat   4500
tggaacgaac atcagaaata gctttaagaa ccttaatggc ttcggctgtg atttcttgac   4560
caacgtggtc acctggcaaa acgacgatct tcttaggggc agacattaga atggtatatc   4620
cttgaaatat atatatatat tgctgaaatg taaaaggtaa gaaaagttag aaagtaagac   4680
gattgctaac cacctattgg aaaaaacaat aggtctagat atcgctcaat actgaccatt   4740
taaatcatac ctgacctcca tagcagaaag tcaaaagcct ccgaccggag gcttttgact   4800
tgatcggcac gtaagaggtt ccaactttca ccataatgaa ataagatcac taccgggcgt   4860
atttttgag ttatcgagat tttcaggagc taaggaagct aaaatgagta ttcaacattt   4920
ccgtgtcgcc cttattccct tttttgcggc attttgcctt cctgtttttg ctcacccaga   4980
aacgctggtg aaagtaaaag atgctgaaga tcagttgggt gcacgagtgg gttacatcga   5040
actggatctc aacagcggta agatccttga gagtttacgc cccgaagaac gttttccaat   5100
gatgagcact tttaaagttc tgctatgtgg cgcggtatta tcccgtattg acgccgggca   5160
agagcaactc ggtcgccgca tacactattc tcagaatgac ttggttgagt actcaccagt   5220
cacagaaaag catctcacgg atggcatgac agtaagagaa ttatgcagtg ctgccataac   5280
catgagtgat aacactgcgg ccaacttact tctggcaacg atcggaggac cgaaggagct   5340
aaccgctttt ttgcacaaca tgggggatca tgtaactcgc cttgatcgtt gggaaccgga   5400
gctgaatgaa gccataccaa acgacgagcg tgacaccacg atgcctgtag caatggcaac   5460
aacgttgcgc aaactattaa ctggcgaact acttactcta gcttcccggc aacaattaat   5520
agactggatg gaggcggata aagttgcagg atcacttctg cgctcggccc tcccggctgg   5580
ctggtttatt gctgataaat ctggagccgg tgagcgtggg tctcgcggta tcattgcagc   5640
actggggcca gatggtaagc cctcccgcat cgtagttatc tacacgacgg ggagtcaggc   5700
aactatggat gaacgaaata gacagatcgc tgagataggt gcctcactga ttaagcattg   5760
gtaagtgacc aaacaggaaa aaccgccct taacatggcc cgctttatca gaagccagac   5820
attaacgctt ctggagaaac tcaacgagct ggacgcggat gaacaggcag acatctgtga   5880
atcgcttcac gaccacgctg atgagcttta ccgcagctgc ctcgcgcgtt tcggtgatga   5940
cggtgaaaac ctctgatgag ggcccaaatg taatcacctg gctcaccttc gggtgggcct   6000
ttctgcgttg ctggcgtttt tccataggct ccgccccccct gacgagcatc acaaaaatcg   6060
```

```
atgctcaagt cagaggtggc gaaacccgac aggactataa agataccagg cgtttccccc   6120

tggaagctcc ctcgtgcgct ctcctgttcc gaccctgccg cttaccggat acctgtccgc   6180

ctttctccct tcgggaagcg tggcgctttc tcatagctca cgctgtaggt atctcagttc   6240

ggtgtaggtc gttcgctcca agctgggctg tgtgcacgaa ccccccgttc agcccgaccg   6300

ctgcgcctta tccggtaact atcgtcttga gtccaacccg gtaagacacg acttatcgcc   6360

actggcagca gccactggta acaggattag cagagcgagg tatgtaggcg gtgctacaga   6420

gttcttgaag tggtggccta actacggcta cactagaaga acagtatttg gtatctgcgc   6480

tctgctgaag ccagttacct cggaaaaaga gttggtagct cttgatccgg caaacaaacc   6540

accgctggta gcggtggttt ttttgtttgc aagcagcaga ttacgcgcag aaaaaaagga   6600

tctcaagaag atcctttgat ttctaccga agaaaggccc acccgtgaag gtgagccagt   6660

gagttgattg cagtccagtt acgctggagt ctgaggctcg tcct                    6704
```

```
<210> SEQ ID NO 14
<211> LENGTH: 6450
<212> TYPE: DNA
<213> ORGANISM: Artificial
<220> FEATURE:
<223> OTHER INFORMATION: Circular plasmid DNA

<400> SEQUENCE: 14

gaatgatatc aaagctgcga ccgtgtggaa gaacgattac aacaggtgtt gtcctctgag     60

gacataaaat acacaccgag attcatcaac tcattgctgg agttagcata tctacaattg    120

ggtgaaatgg ggagcgattt gcaggcattt gctcggcatg ccggtagagg tgtggtcaat    180

aagagcgacc tcatgctata cctgagaaag caacctgacc tacaggaaag agttactcaa    240

gaacaagaat tttcgtttta aaacctaaga gtcactttaa aatttgtata cacttatttt    300

ttttataact tatttaataa taaaaatcat aaatcataag aaattcgctt atttagaagt    360

gtcaacaacg tatctaccaa cgatttgacc cttttccatc ttttcgtaaa tttctggcaa    420

ggtagacaag ccgacaacct tgattggaga cttgaccaaa cctctggcga agaagtccaa    480

agcttctcga gtcggccgaa ttcgggagag gcataatctg gcacatcata agggtaggag    540

gcatctccac tcagcaagag gctggtatcg ttaacatccg cttcaatttc atgaaaacca    600

ttcgatttca gccagtcagg ctggatcggc ggcccggcgt gaagaatggt tttcggcgtc    660

atgcccggca ccacgttaat cgcctgatcc gccatttcca tcggcatctc ctgtccggtg    720

cgcaggtagt cgataaactg ctcaatgatg gcattgcact cctcgatatc tttattgata    780

ccagctacct ttctcttctt ttttggagga gcacccataa gcttaagctt aattcctcct    840

tgacgttaaa gtatagaggt atattaacaa ttttttgttg atacttttat tacatttgaa    900

taagaagtaa tacaaaccga aaatgttgaa agtattagtt aaagtggtta tgcagttttt    960

gcatttatat atctgttaat agatcaaaaa tcatcgcttc gctgattaat taccccagaa   1020

ataaggctaa aaaactaatc gcattatcat cctatggttg ttaatttgat tcgttcattt   1080

gaaggtttgt ggggccaggt tactgccaat ttttcctctt cataaccata aaagctagta   1140

ttgtagaatc tttattgttc ggagcagtgc ggcgcgaggc acatctgcgt ttcaggaacg   1200

cgaccggtga agacgaggac gcacggagga gagtcttcct tcggagggct gtcacccgct   1260

cggcggcttc taatccgtac ttcaatatag caatgagcag ttaagcgtat tactgaaagt   1320

tccaaagaga aggttttttt aggctaagat aatggggtac cggatcatct cgcagcttga   1380

attgcgcctg ctgcaggata tccagctgcg caaggaacgc ccgtcgtggc cagccacgat   1440
```

-continued

```
agccgcgctg cctcgtcttg cagttcattc agggcaccgg acaggtcggt cttgacaaaa   1500

agaaccgggc gcccctgcgc tgacagccgg aacacggcgg catcagagca gccgattgtc   1560

tgttgtgccc agtcatagcc gaatagcctc tccacccaag cggccggaga acctgcgtgc   1620

aatccatctt gttcaatcat actcttcctt tttcaatatt attgaagcat ttatcagggt   1680

tattgtctca tgagcggata catatttgaa tgtatttaga aaaataaaca aataggggtt   1740

ccgcgcacat ttccccgaaa agtgccacct gcggacggat cgcttgcctg taacttacac   1800

gcgcctcgta tcttttaatg atggaataat ttgggaattt actctgtgtt tatttatttt   1860

tatgttttgt atttggattt tagaaagtaa ataaagagta gaagagttac ggaatgaaga   1920

aaaaaaaata aacaaaggtt taaaaaattt caacaaaaag cgtactttac atatatattt   1980

attagacaag aaaagcagat taaatagata tacattcgat taacgataag taaaatgtaa   2040

aatcacagga ttttcgtgtg tggtcttcta cacagacaag atgaaacaat tcggcattaa   2100

tacctgagag caggaagagc aagataaaag gtagtatttg ttggcgatcc ccctagagtc   2160

ttttacatct tcggaaaaca aaaactattt tttctttaat ttcttttttt actttctatt   2220

tttaatttat atatttatat taaaaaattt aaattataat tatttttata gcacgtgatg   2280

aaaaggaccg acgtctaaga aaccattatt atcatgacat taacctataa aaataggcgt   2340

atcacgaggc cctttcgtct cgcgcgtttc ggtgatgacg gtgaaaacct ctgacacatg   2400

cagctcccgg agacggtcac agcttgtctg taagcggatg ccgggagcag acaagcccgt   2460

cagggcgcgt cagcgggtgt tggcgggtgt cggggctggc ttaactatgc ggcatcagag   2520

cagattgtac tgagagtgca ccatatgcgg tgtgaaatac cgcacagatg cgtaaggaga   2580

aaataccgca tcaggaaatt gtaaacgtta atattttgtt aaaattcgcg ttaaattttt   2640

gttaaatcag ctcatttttt aaccaatagg ccgaaatcgg caaaatccct tataaatcaa   2700

aagaatagac cgagataggg ttgagtgttg ttccagtttg gaacaagagt ccactattaa   2760

agaacgtgga ctccaacgtc aaagggcgaa aaaccgtcta tcagggcgat ggcccactac   2820

gtgaaccatc accctaatca agttttttgg ggtcgaggtg ccgtaaagca ctaaatcgga   2880

accctaaagg gagcccccga tttagagctt gacggggaaa gccggcgaac gtggcgagaa   2940

aggaagggaa gaaagcgaaa ggagcgggcg ctagggcgct ggcaagtgta gcggtcacgc   3000

tgcgcgtaac caccacaccc gccgcgctta atgcgccgct acagggcgcg tcgcgccatt   3060

cgccattcag gctgcgcaac tgttgggaag ggcgatcggt gcgggcctct tcgctattac   3120

gccagctgga tatcctgcag gcgcaattct ctagacctac cctatgaaca tattccattt   3180

tgtaatttcg tgtcgtttct attatgaatt tcatttataa agtttatgta caaatatcat   3240

aaaaaaagag aatcttttta agcaaggatt ttcttaactt cttcggcgac agcatcaccg   3300

acttcggtgg tactgttgga accacctaaa tcaccagttc tgatacctgc atccaaaacc   3360

tttttaactg catcttcaat ggccttacct tcttcaggca agttcaatga caatttcaac   3420

atcattgcag cagacaagat agtggcgata gggttgacct tattctttgg caaatctgga   3480

gcagaaccgt ggcatggttc gtacaaacca aatgcggtgt tcttgtctgg caaagaggcc   3540

aaggacgcag atggcaacaa acccaaggaa cctgggataa cggaggcttc atcggagatg   3600

atatcaccaa acatgttgct ggtgattata ataccattta ggtgggttgg gttcttaact   3660

aggatcatgg cggcagaatc aatcaattga tgttgaacct tcaatgtagg aaattcgttc   3720

ttgatggttt cctccacagt tttctccat aatcttgaag aggccaaaac attagcttta   3780

tccaaggacc aaataggcaa tggtggctca tgttgtaggg ccatgaaagc ggccattctt   3840
```

```
gtgattcttt gcacttctgg aacggtgtat tgttcactat cccaagcgac accatcacca   3900
tcgtcttcct ttctcttacc aaagtaaata cctcccacta attctctgac aacaacgaag   3960
tcagtacctt tagcaaattg tggcttgatt ggagataagt ctaaaagaga gtcggatgca   4020
aagttacatg gtcttaagtt ggcgtacaat tgaagttctt tacggatttt tagtaaacct   4080
tgttcaggtc taacactacc tgtaccccat ttaggaccac ccacagcacc taacaaaacg   4140
gcatcaacct tcttggaggc ttccagcgcc tcatctggaa gtgggacacc tgtagcgtcg   4200
atagcagcac caccaattaa atgattttcg aaatcgaact tgacattgga acgaacatca   4260
gaaatagctt taagaacctt aatggcttcg gctgtgattt cttgaccaac gtggtcacct   4320
ggcaaaacga cgatcttctt aggggcagac attagaatgg tatatccttg aaatatatat   4380
atatattgct gaaatgtaaa aggtaagaaa agttagaaag taagacgatt gctaaccacc   4440
tattggaaaa aacaataggt ctagatatcg ctcaatactg accatttaaa tcatacctga   4500
cctccatagc agaaagtcaa aagcctccga ccggaggctt ttgacttgat cggcacgtaa   4560
gaggttccaa ctttcaccat aatgaaataa gatcactacc gggcgtattt tttgagttat   4620
cgagattttc aggagctaag gaagctaaaa tgagtattca acatttccgt gtcgccctta   4680
ttcccttttt tgcggcattt tgccttcctg tttttgctca cccagaaacg ctggtgaaag   4740
taaaagatgc tgaagatcag ttgggtgcac gagtgggtta catcgaactg gatctcaaca   4800
gcggtaagat ccttgagagt tttcgccccg aagaacgttt tccaatgatg agcactttta   4860
aagttctgct atgtggcgcg gtattatccc gtattgacgc cgggcaagag caactcggtc   4920
gccgcataca ctattctcag aatgacttgg ttgagtactc accagtcaca gaaaagcatc   4980
tcacggatgg catgacagta agagaattat gcagtgctgc cataaccatg agtgataaca   5040
ctgcggccaa cttacttctg gcaacgatcg gaggaccgaa ggagctaacc gcttttttgc   5100
acaacatggg ggatcatgta actcgccttg atcgttggga accggagctg aatgaagcca   5160
taccaaacga cgagcgtgac accacgatgc ctgtagcaat ggcaacaacg ttgcgcaaac   5220
tattaactgg cgaactactt actctagctt cccggcaaca attaatagac tggatggagg   5280
cggataaagt tgcaggatca cttctgcgct cggcccttcc ggctggctgg tttattgctg   5340
ataaatctgg agccggtgag cgtgggtctc gcggtatcat tgcagcactg gggccagatg   5400
gtaagccctc ccgcatcgta gttatctaca cgacggggag tcaggcaact atggatgaac   5460
gaaatagaca gatcgctgag ataggtgcct cactgattaa gcattggtaa gtgaccaaac   5520
aggaaaaaac cgcccttaac atggcccgct ttatcagaag ccagacatta acgcttctgg   5580
agaaactcaa cgagctggac gcggatgaac aggcagacat ctgtgaatcg cttcacgacc   5640
acgctgatga gctttaccgc agctgcctcg cgcgtttcgg tgatgacggt gaaaacctct   5700
gatgagggcc caaatgtaat cacctggctc accttcgggt gggcctttct gcgttgctgg   5760
cgtttttcca taggctccgc ccccctgacg agcatcacaa aaatcgatgc tcaagtcaga   5820
ggtggcgaaa cccgacagga ctataaagat accaggcgtt tccccctgga agctccctcg   5880
tgcgctctcc tgttccgacc ctgccgctta ccggatacct gtccgccttt ctcccttcgg   5940
gaagcgtggc gctttctcat agctcacgct gtaggtatct cagttcggtg taggtcgttc   6000
gctccaagct gggctgtgtg cacgaacccc ccgttcagcc cgaccgctgc gccttatccg   6060
gtaactatcg tcttgagtcc aacccggtaa gacacgactt atcgccactg gcagcagcca   6120
ctggtaacag gattagcaga gcgaggtatg taggcggtgc tacagagttc ttgaagtggt   6180
ggcctaacta cggctacact agaagaacag tatttggtat ctgcgctctg ctgaagccag   6240
```

ttacctcgga aaaagagttg gtagctcttg atccggcaaa caaaccaccg ctggtagcgg 6300
tggttttttt gtttgcaagc agcagattac gcgcagaaaa aaaggatctc aagaagatcc 6360
tttgattttc taccgaagaa aggcccaccc gtgaaggtga gccagtgagt tgattgcagt 6420
ccagttacgc tggagtctga ggctcgtcct 6450

<210> SEQ ID NO 15
<211> LENGTH: 7458
<212> TYPE: DNA
<213> ORGANISM: artificial
<220> FEATURE:
<223> OTHER INFORMATION: Circular plasmid DNA

<400> SEQUENCE: 15
gaattccccg gatccacgcg tgagctcccg ggtcgacgcg gccgcgcggg gaattcccgg 60
ggagctcacg cgttcgcgaa tcgatccgcg gtctagaaat tcctggcatt atcacataat 120
gaattataca ttatataaag taatgtgatt tcttcgaaga atatactaaa aaatgagcag 180
gcaagataaa cgaaggcaaa gatgacagag cagaaagccc tagtaaagcg tattacaaat 240
gaaaccaaga ttcagattgc gatctcttta aagggtggtc ccctagcgat agagcactcg 300
atcttcccag aaaaagaggc agaagcagta gcagaacagg ccacacaatc gcaagtgatt 360
aacgtccaca caggtatagg gtttctggac catatgatac atgctctggc caagcattcc 420
ggctggtcgc taatcgttga gtgcattggt gacttacaca tagacgacca tcacaccact 480
gaagactgcg ggattgctct cggtcaagct tttaaagagg ccctactggc gcgtggagta 540
aaaaggtttg gatcaggatt tgcgcctttg gatgaggcac tttccagagc ggtggtagat 600
ctttcgaaca ggccgtacgc agttgtcgaa cttggtttgc aaagggagaa agtaggagat 660
ctctcttgcg agatgatccc gcattttctt gaaagctttg cagaggctag cagaattacc 720
ctccacgttg attgtctgcg aggcaagaat gatcatcacc gtagtgagag tgcgttcaag 780
gctcttgcgg ttgccataag agaagccacc tcgcccaatg gtaccaacga tgttccctcc 840
accaaaggtg ttcttatgta gtgacaccga ttatttaaag ctgcagcata cgatatatat 900
acatgtgtat atatgtatac ctatgaatgt cagtaagtat gtatacgaac agtatgatac 960
tgaagatgac aaggtaatgc atcattctat acgtgtcatt ctgaacgagg cgcgctttcc 1020
ttttttcttt ttgctttttc tttttttttc tcttgaactc gagaaaaaaa atataaaaga 1080
gatggaggaa cgggaaaaag ttagttgtgg tgataggtgg caagtggtat tccgtaagaa 1140
caacaagaaa agcatttcat attatggctg aactgagcga acaagtgcaa aatttaagca 1200
tcaacgacaa caacgagaat ggttatgttc ctcctcactt aagaggaaaa ccaagaagtg 1260
ccagaaataa catgagcaac tacaataaca acaacggcgg ctacaacggt ggccgtggcg 1320
gtggcagctt ctttagcaac aaccgtcgtg gtggttacgg caacggtggt ttcttcggtg 1380
gaaacaacgg tggcagcaga tctaacggcc gttctggtgg tagatggatc gatggcaaac 1440
atgtcccagc tccaagaaac gaaaaggccg agatcgccat atttggtgtc cccgaggatc 1500
tgccaattct ctagatatcg ctcaatactg accatttaaa tcatacctga cctccatagc 1560
agaaagtcaa aagcctccga ccggaggctt ttgacttgat cggcacgtaa gaggttccaa 1620
ctttcaccat aatgaaataa gatcactacc gggcgtattt tttgagttat cgagattttc 1680
aggagctaag gaagctaaaa tgagccatat tcaacgggaa acgtcttgct cgaggccgcg 1740
attaaattcc aacatggatg ctgatttata tgggtataaa tgggctcgcg ataatgtcgg 1800
gcaatcaggt gcgacaatct atcgattgta tgggaagccc gatgcgccag agttgtttct 1860

-continued

```
gaaacatggc aaaggtagcg ttgccaatga tgttacagat gagatggtca ggctaaactg   1920
gctgacggaa tttatgcctc ttccgaccat caagcatttt atccgtactc ctgatgatgc   1980
atggttactc accactgcga tccccaggaa aacagcattc caggtattag aagaatatcc   2040
tgattcaggt gaaaatattg ttgatgcgct ggcagtgttc ctgcgccggt tgcattcgat   2100
tcctgtttgt aattgtcctt ttaacggcga tcgcgtattt cgtctcgctc aggcgcaatc   2160
acgaatgaat aacggtttgg ttggtgcgag tgattttgat gacgagcgta atggctggcc   2220
tgttgaacaa gtctggaaag aaatgcataa gcttttgcca ttctcaccgg attcagtcgt   2280
cactcatggt gatttctcac ttgataacct tatttttgac gaggggaaat taataggttg   2340
tattgatgtt ggacgagtcg gaatcgcaga ccgataccag gatcttgcca tcctatggaa   2400
ctgcctcggt gagttttctc cttcattaca gaaacggctt tttcaaaaat atggtattga   2460
taatcctgat atgaataaat tgcagtttca cttgatgctc gatgagtttt tctaaatgac   2520
caaacaggaa aaaaccgccc ttaacatggc ccgctttatc agaagccaga cattaacgct   2580
tctggagaaa ctcaacgagc tggacgcgga tgaacaggca gacatctgtg aatcgcttca   2640
cgaccacgct gatgagcttt accgcagctg cctcgcgcgt ttcggtgatg acggtgaaaa   2700
cctctgatga gggccctgga attaattcca catgttaaaa tagtgaagga gcatgttcgg   2760
cacacagtgg accgaacgtg gggtaagtgc actagggtcc ggttaaacgg atctcgcatt   2820
gatgaggcaa cgctaattat caacatatag attgttatct atctgcatga acacgaaatc   2880
tttacttgac gacttgaggc tgatggtgtt tatgcaaaga aaccactgtg tttaatatgt   2940
gtcactgttt gatattactg tcagcgtaga agataatagt aaaagcggtt aataagtgta   3000
tttgagataa gtgtgataaa gtttttacag cgaaaagacg ataaatacaa gaaaatgatt   3060
acgaggatac ggagagaggt atgtacatgt gtatttatat actaagctgc cggcggttgt   3120
ttgcaagacc gagaaaaggc tagcaagaat cgggtcattg tagcgtatgc gcctgtgaac   3180
attctcttca acaagtttga ttccattgcg gtgaaatggt aaaagtcaac cccctgcgat   3240
gtatattttc ctgtacaatc aatcaaaaag ccaaatgatt tagcattatc tttacatctt   3300
gttattttac agattttatg tttagatctt ttatgcttgc ttttcaaaag gcctgcaggc   3360
aagtgcacaa acaatactta aataaatact actcagtaat aacctatttc ttagcatttt   3420
tgacgaaatt tgctattttg ttagagtctt ttacaccatt tgtctcccac ctccgcttac   3480
atcaacacca ataacgccat ttaatctaag cgcatcacca acattttctg gcgtcagtcc   3540
accagctaac ataaaatgta agctttcggg gctctcttgc cttccaaccc agtcagaaat   3600
cgagttccaa tccaaaagtt cacctgtccc acctgcttct gaatcaaaca agggaataaa   3660
cgaatgaggt ttctgtgaag ctgcactgag tagtatgttg cagtcttttg gaaatacgag   3720
tcttttaata actggcaaac cgaggaactc ttggtattct tgccacgact catctccatg   3780
cagttggacg atatcaatgc cgtaatcatt gaccagagcc aaaacatcct ccttaggttg   3840
attacgaaac acgccaacca agtatttcgg agtgcctgaa ctatttttat atgcttttac   3900
aagacttgaa attttccttg caataaccgg gtcaattgtt ctctttctat tgggcacaca   3960
tataataccc agcaagtcag catcggaatc tagagcacat tctgcggcct ctgtgctctg   4020
caagccgcaa actttcacca atggaccaga actacctgtg aaattaataa cagacatact   4080
ccaagctgcc tttgtgtgct taatcacgta tactcacgtg ctcaatagtc accaatgccc   4140
tccctcttgg ccctctcctt ttcttttttc gaccgaatta attccatggc agacatctgt   4200
gaatcgcttc acgaccacgc tgatgagctt taccgctggg ccattctcat gaagaatatc   4260
```

```
ttgaatttat tgtcatatta ctagttggtg tggaagtcct aatatcggtg atcaatatag   4320
tggttgacat gctggctagt caacattgag ccttttgatc atgcaaatat attacggtat   4380
tttacaatca aatatcaaac ttaactattg actttataac ttatttaggt ggtaacattc   4440
ttataaaaaa gaaaaaaatt actgcaaaac agtactagct tttaacttgt atcctaggtt   4500
atctatgctg tctcaccata gagaatatta cctatttcag aatgtatgtc catgattcgc   4560
cgggtaaata catataatac acaaatctgg cttaataaag tctataatat atctcataaa   4620
gaagtgctaa attggctagt gctatatatt tttaagaaaa tttcttttga ctaagtccat   4680
atcgactttg taaaagttca cattagcata catatattac acgagccaga aatagtaact   4740
tttgcctaaa tcacaaattg caaaatttaa ttgcttgcaa aaggtcacat gcttataatc   4800
aacttttta aaaatttaaa atactttttt atttttattt tttaaacata aatgaaataa    4860
tttatttatt gtttatgatt accgaaacat aaaacctgct caagaaaaag aaactgtttt   4920
gtccttggaa aaaaagcact acctaggagc ggccaaaatg ccgaggcttt catagcttaa   4980
actctttaca gaaaataggc attatagatc agttcgagtt ttcttattct tccttccggt   5040
tttatcgtca cagttttaca gtaaataagt atcacctctt agagttaacc tatactaaaa   5100
tttatgccag ttaactatga gataagcaag tatcatctca tttcattacc tgaagtcgag   5160
taaacagaaa atccaattgt tgatgaacct caatgactta gaactatcta tcggcagatc   5220
atataaagag gatttaggta cctagaggac tgtacctgga gtatatatat atatatatat   5280
atattatctc aactatagtc catagaggtt tctttcttga ggccttaaac tgctaaagaa   5340
tgatattggt ggaatgcaag caccaagcgc tcttcttgcg tgactgttca tatacttcaa   5400
accaagaatg taactggcat tgacccatcc aaaaccttca gtagctgccc ctttaaagtc   5460
agcaccttga ttaccgtatt ctgcttcaac acgatgagga tctgttcctc ttgtgacatc   5520
atattttca accacaatac cattataatc gacaaaagcc tttgtcatca tgaaaagcca    5580
tctataagct agcctattcg ttacagttaa ataaccataa gaacggaggc cttcccaagc   5640
aagaatttga tggggtgccc aaccaaatgg atagtcccat tgtctaattg gtctcgaaat   5700
agaaattggg cctcgagaac gctccgtaca tgcagctaaa cctccaagca tctctaactt   5760
gggtagtgct ttctccacca ttttctgtgc ttgctccttc gtggcaagtc cagcccataa   5820
tgcccagaat gtagttgcgg attcgtatga cgttctgtgc ttgatttttg tgttgtagtc   5880
aaagaaaagg tccggttaaa cggatctcgc attgatgagg caacgctaat tatcaacata   5940
tagattgtta tctatctgca tgaacacgaa atctttactt gacgacttga ggctgatggt   6000
gtttatgcaa agaaaccact gtgtttaata tgtgtcactg tttgatatta ctgtcagcgt   6060
agaagataat agtaaaagcg gttaataagt gtatttgaga taagtgtgat aaagttttta   6120
cagcgaaaag acgataaata caagaaaatg attacgagga tacggagaga ggtatgtaca   6180
tgtgtattta tatactaagc tgccggcggt tgtttgcaag accgagaaaa ggctagcaag   6240
aatcgggtca ttgtagcgta tgcgcctgtg aacattctct tcaacaagtt tgattccatt   6300
gcggtgaaat ggtaaaagtc aacccccctgc gatgtatatt ttcctgtaca atcaatcaaa  6360
aagccaaatg atttagcatt atctttacat cttgttattt tacagatttt atgtttagat   6420
cttttatgct tgcttttcaa aaggcctgca ggcaagtgca caaacaatac ttaaataaat   6480
actactcagt aataacctat ttcttagcat ttttgacgaa atttgctatt ttgttagagt   6540
cttttacacc atttgtctcc acacctccgc ttacatcaac accaataacg ccatttaatc   6600
taagcgcatc accaacattt tctggcgtca gtccaccagc taacataaaa tgttgcctcg   6660
```

```
cgcgtttcgg tgatgacggt gaaaaccttt gacacatggg cccaaatgta atcacctggc   6720

tcaccttcgg gtgggccttt ctgcgttgct ggcgtttttc cataggctcc gcccccctga   6780

cgagcatcac aaaaatcgat gctcaagtca gaggtggcga aacccgacag gactataaag   6840

ataccaggcg tttccccctg gaagctccct cgtgcgctct cctgttccga ccctgccgct   6900

taccggatac ctgtccgcct ttctcccttc gggaagcgtg gcgctttctc atagctcacg   6960

ctgtaggtat ctcagttcgg tgtaggtcgt tcgctccaag ctgggctgtg tgcacgaacc   7020

ccccgttcag cccgaccgct gcgccttatc cggtaactat cgtcttgagt ccaacccggt   7080

aagacacgac ttatcgccac tggcagcagc cactggtaac aggattagca gagcgaggta   7140

tgtaggcggt gctacagagt tcttgaagtg gtggcctaac tacggctaca ctagaagaac   7200

agtatttggt atctgcgctc tgctgaagcc agttacctcg gaaaaagagt tggtagctct   7260

tgatccggca aacaaaccac cgctggtagc ggtggttttt ttgtttgcaa gcagcagatt   7320

acgcgcagaa aaaaaggatc tcaagaagat cctttgattt tctaccgaag aaaggcccac   7380

ccgtgaaggt gagccagtga gttgattgca gtccagttac gctggagtct gaggctcgtc   7440

ctgaatgata tcaagctt                                                 7458
```

```
<210> SEQ ID NO 16
<211> LENGTH: 41
<212> TYPE: DNA
<213> ORGANISM: artificial
<220> FEATURE:
<223> OTHER INFORMATION: oligonucleotide primer

<400> SEQUENCE: 16

actcacacca tggcagacat ctgtgaatcg cttcacgacc a                         41


<210> SEQ ID NO 17
<211> LENGTH: 44
<212> TYPE: DNA
<213> ORGANISM: artificial
<220> FEATURE:
<223> OTHER INFORMATION: oligonucleotide primer

<400> SEQUENCE: 17

actcacaggg cccatgtgtc aaaggttttc accgtcatca ccga                      44


<210> SEQ ID NO 18
<211> LENGTH: 42
<212> TYPE: DNA
<213> ORGANISM: artificial
<220> FEATURE:
<223> OTHER INFORMATION: oligonucleotide primer

<400> SEQUENCE: 18

actcacaggg ccctggaatt aattccacat gttaaatagt ga                        42


<210> SEQ ID NO 19
<211> LENGTH: 31
<212> TYPE: DNA
<213> ORGANISM: artificial
<220> FEATURE:
<223> OTHER INFORMATION: oligonucleotide primer

<400> SEQUENCE: 19

actgtgccct ccatggaatt aattcggtcg a                                    31


<210> SEQ ID NO 20
<211> LENGTH: 18
<212> TYPE: DNA
```

<213> ORGANISM: artificial
<220> FEATURE:
<223> OTHER INFORMATION: oligonucleotide primer

<400> SEQUENCE: 20
gaattcccgg ggagctca 18

<210> SEQ ID NO 21
<211> LENGTH: 23
<212> TYPE: DNA
<213> ORGANISM: artificial
<220> FEATURE:
<223> OTHER INFORMATION: oligonucleotide primer

<400> SEQUENCE: 21
caattggtcg acgctctccc tta 23

<210> SEQ ID NO 22
<211> LENGTH: 50
<212> TYPE: DNA
<213> ORGANISM: artificial
<220> FEATURE:
<223> OTHER INFORMATION: oligonucleotide multiple cloning site

<400> SEQUENCE: 22
aattccccgg atccacgcgt gagctcccgg gtcgacgcgg ccgcgcgggg 50

<210> SEQ ID NO 23
<211> LENGTH: 26
<212> TYPE: DNA
<213> ORGANISM: artificial
<220> FEATURE:
<223> OTHER INFORMATION: oligonucleotide primer

<400> SEQUENCE: 23
cgggatccat gaccacgctg gccggc 26

<210> SEQ ID NO 24
<211> LENGTH: 40
<212> TYPE: DNA
<213> ORGANISM: artificial
<220> FEATURE:
<223> OTHER INFORMATION: oligonucleotide primer

<400> SEQUENCE: 24
gccgtcgacg tgcaatatct ggcttgagat aatgaaaggc 40

<210> SEQ ID NO 25
<211> LENGTH: 31
<212> TYPE: DNA
<213> ORGANISM: artificial
<220> FEATURE:
<223> OTHER INFORMATION: oligonucleotide primer

<400> SEQUENCE: 25
cgggtcgacc tgaattctga ggtgagacgc c 31

<210> SEQ ID NO 26
<211> LENGTH: 12
<212> TYPE: DNA
<213> ORGANISM: artificial
<220> FEATURE:
<223> OTHER INFORMATION: oligonucleotide linker

<400> SEQUENCE: 26
aatccggtac cg 12

<210> SEQ ID NO 27
<211> LENGTH: 14
<212> TYPE: DNA
<213> ORGANISM: artificial
<220> FEATURE:
<223> OTHER INFORMATION: oligonucleotide linker

<400> SEQUENCE: 27
ggatcccggt accg 14

<210> SEQ ID NO 28
<211> LENGTH: 29
<212> TYPE: DNA
<213> ORGANISM: artificial
<220> FEATURE:
<223> OTHER INFORMATION: oligonucleotide primer

<400> SEQUENCE: 28
cgggatccat ggccgaagcg ccccaggtg 29

<210> SEQ ID NO 29
<211> LENGTH: 33
<212> TYPE: DNA
<213> ORGANISM: artificial
<220> FEATURE:
<223> OTHER INFORMATION: oligonucleotide primer

<400> SEQUENCE: 29
gccgtcgacg gcctgacacc cagctatgtg tcg 33

<210> SEQ ID NO 30
<211> LENGTH: 36
<212> TYPE: DNA
<213> ORGANISM: artificial
<220> FEATURE:
<223> OTHER INFORMATION: oligonucleotide

<400> SEQUENCE: 30
atccagtgac gattagcacc gtcacgctta gatatg 36

<210> SEQ ID NO 31
<211> LENGTH: 37
<212> TYPE: DNA
<213> ORGANISM: artificial
<220> FEATURE:
<223> OTHER INFORMATION: oligonucleotide

<400> SEQUENCE: 31
tcgacatatc aaagcgtgac ggtgctaatc gtcactg 37

<210> SEQ ID NO 32
<211> LENGTH: 64
<212> TYPE: DNA
<213> ORGANISM: artificial
<220> FEATURE:
<223> OTHER INFORMATION: oligonucleotide

<400> SEQUENCE: 32
cagtgacgat tagcaccgtc acgcttagat atagtgacga ttagcaccgt cacgcttaga 60
tata 64

<210> SEQ ID NO 33
<211> LENGTH: 72
<212> TYPE: DNA
<213> ORGANISM: artificial
<220> FEATURE:

<223> OTHER INFORMATION: oligonucleotide

<400> SEQUENCE: 33
cgcgtatatc taagcgtgac ggtgctaatc gtcactatat ctaagagtga cggtgctaat 60
cgtcactgag ct 72

<210> SEQ ID NO 34
<211> LENGTH: 629
<212> TYPE: DNA
<213> ORGANISM: artificial
<220> FEATURE:
<223> OTHER INFORMATION: Fragment of Bcl-XL promoter containing Pax3 binding site; used in positive controls

<400> SEQUENCE: 34
ctgcaggggg ctccagaagg ccgccttggg ctcggcctca ggaaaaacga ggtctccact 60
gtgggagccc cgacccttct tcctggccgg tggcggggct cagtgcctct ctctcacccc 120
gtctttgtgc gtggggtgcc ggcggccatt gtgtccgggc gcggaatgga ggacctggcc 180
gtcccccagt gctgtgtcca gggcctttgg ggaattcaaa gacaactagc ggtgtttgtg 240
gggggtctcc agcatacgcc tctcggaaaa acccgggagt ggtctttccg aaatcagatc 300
acagatccga ggctgtcttc cccctgtccg cgtccctgcg cgaaaccttg agattcactt 360
ggaagtccct ttagggtttc ggaagcctca tctagggctg gtacttaaat agaaagaaag 420
aaaggagggg tggggggaaa ttacactaaa cccatacctc cgggagagtt ctcctgactc 480
ccagtaggag gcggagagcc aaggggcgtg ctagagcgag gggttgggc tcccgggtgg 540 ctggagcctg cggagcagag agaggccgcc ctcgatctgg tcgatggagg aaccaggttg 600
tgagggggca ggttcctaag cttcgcaat 629

<210> SEQ ID NO 35
<211> LENGTH: 28
<212> TYPE: DNA
<213> ORGANISM: artificial
<220> FEATURE:
<223> OTHER INFORMATION: oligonucleotide primer

<400> SEQUENCE: 35
caggatccct gcagggggct ccagaagg 28

<210> SEQ ID NO 36
<211> LENGTH: 33
<212> TYPE: DNA
<213> ORGANISM: artificial
<220> FEATURE:
<223> OTHER INFORMATION: oligonucleotide primer

<400> SEQUENCE: 36
gcacgcgttc atgaattgcg aagcttagga cct 33

<210> SEQ ID NO 37
<211> LENGTH: 585
<212> TYPE: DNA
<213> ORGANISM: artificial
<220> FEATURE:
<223> OTHER INFORMATION: Fragment of Msx2 promoter containing Pax3 binding site; used in positive controls

<400> SEQUENCE: 37
tctacctaaa ttccctgctg aggagctctc aggggggttt cctccagctc cctccggatt 60
tgtctgccca gttggaggtt tgatctgcct tatccctcct tcccacagcg cacaggtaaa 120

```
aaaagaaaat gagctcagag aggtgccatc ttttgcccga agtcacacag cgaatgtcca    180

cggattggag ggcagtggtg gaattcctgg cggcccttgg acgcccattt gtctgcccgc    240

ttctgatacc cgggttcgga gaataggcct ctaacaagcg gcccattaga aggaattgtc    300

actcctccgg gagtgaggtt gtcccattag ggcgaattgt cattcctcct ggagcgaggt    360

tgtcctgctc cgcgaaggct gagtgccggg ccgagagcaa ttaacgcggc tccggcgcgg    420

gcagccgcct ctgccccggg cagcgggggc ggggcgcccg gcgcggctgg agccggtcac    480

ccggcgcagc cccttccccc ggagcccgcc tttcatctcc ccgcgcctgg cgcctacccg    540

cagccctggc ccgtctacag ccttctctgc ccctccccct gcccc                    585


<210> SEQ ID NO 38
<211> LENGTH: 42
<212> TYPE: DNA
<213> ORGANISM: artificial
<220> FEATURE:
<223> OTHER INFORMATION: oligonucleotide primer

<400> SEQUENCE: 38

cgggatccga tatctctacc taaattccct gctgaggagc tc                        42


<210> SEQ ID NO 39
<211> LENGTH: 38
<212> TYPE: DNA
<213> ORGANISM: artificial
<220> FEATURE:
<223> OTHER INFORMATION: oligonucleotide primer

<400> SEQUENCE: 39

cgacgcgtga tatctaaccg tgaagcgttg agcacaga                            38


<210> SEQ ID NO 40
<211> LENGTH: 477
<212> TYPE: DNA
<213> ORGANISM: artificial
<220> FEATURE:
<223> OTHER INFORMATION: Fragment of Trp-1 promoter containing Pax3
      binding sites; used in positive controls

<400> SEQUENCE: 40

aagctttgta gagtaatcat gtattccaaa ctcaggctta catttgaatg ttggctacat     60

atgtatgagt tttcaacttc caggagaaaa cgtctcttta aaagagaaca accaaaagct    120

aacagaaata caagtgtgac attggcctta gttcgaccaa gaagcaattc atcttgtttc    180

ttcctttgtg gtatacagat aagaaaaata aaatcactac aacgaagcaa aatctcttca    240

gcgtctctaa tacatcttcc aaatcagtgt gtctgacctt ttcttaagac tttaaccatc    300

acaaggaaac cagtggggag ggagtcatgt gctgcctagt agttaaaggg caggagaatt    360

cactggtgtg agaagggatt agtgagagct ggaagagagg accagcccct cccagtgtga    420

ggaatctggc ttgggattta ctgtctggca gaaaatctct tcgggcaatt aacagct       477


<210> SEQ ID NO 41
<211> LENGTH: 39
<212> TYPE: DNA
<213> ORGANISM: artificial
<220> FEATURE:
<223> OTHER INFORMATION: oligonucleotide primer

<400> SEQUENCE: 41

cgggatccga tatcaagctt ttaccactgt gccttctcc                            39
```

<210> SEQ ID NO 42
<211> LENGTH: 35
<212> TYPE: DNA
<213> ORGANISM: artificial
<220> FEATURE:
<223> OTHER INFORMATION: oligonucleotide primer

<400> SEQUENCE: 42
cgacgcgtga tatcagctgt taattgcccg aagag 35

<210> SEQ ID NO 43
<211> LENGTH: 20
<212> TYPE: DNA
<213> ORGANISM: artificial
<220> FEATURE:
<223> OTHER INFORMATION: oligonucleotide

<400> SEQUENCE: 43
gtaaacaaca acatgttgac 20

<210> SEQ ID NO 44
<211> LENGTH: 31
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (7)..(17)
<223> OTHER INFORMATION: n is a, c, g, or t

<400> SEQUENCE: 44
acaacannnn nnnnnnnata aacatgttta c 31

<210> SEQ ID NO 45
<211> LENGTH: 21
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (8)..(14)
<223> OTHER INFORMATION: n is a, c, g, or t

<400> SEQUENCE: 45
tgtttacnnn nnnntgttta c 21

<210> SEQ ID NO 46
<211> LENGTH: 1013
<212> TYPE: DNA
<213> ORGANISM: Artificial
<220> FEATURE:
<223> OTHER INFORMATION: Fragment of Gab-1 intronic sequence present in mouse genomic library and containing FKHR binding sites

<400> SEQUENCE: 46
atctgccgtt gagtctgagg ctcgtcctga atgatatcaa gcttgaattc gtcctggcat 60
ccgtagtatc agacatgaca tactgcgtgc ctcatgtgga aggtgctgtc atctgaccag 120
gccttcatta ctacggtgcc ttcctaaaac tcagataaaa atggaaactg acccaagagg 180
cagccccggg gtccctggcc acagtgtccc tcagagtcag tcagtctgca agcgctcttt 240
aacttcaaat accattcaaa ctgttatcgc atatttactt agctctgcag tttctaacaa 300
acccaccaaa caggacgagc tagtctgaat tgacgagcca gtctacatta tacaatatac 360
cagggagcca gctgctcctg ggtcagacaa gtcaggacaa gggctgaaag agttaaagct 420

-continued

```
cactacatac acctgaaggc agcctctgca gattcacttg tgtggaaatg gttttacccc    480

caaaacaggg agagcccaac cacccctaaa aaggctgcat gtgtccccac aaataccaac    540

cgagctgctg tgattgacaa cacacacata agaaagcaac aacaaaaaaa gcatttgagc    600

ttcgcctatg atatctgacg taccccctaaa taagtcttcc ttgggtctgg taaaggtaac   660

gcattctgaa gagattttca gtaattagtc atcgccgctg cgcccccagc acgctatcag    720

cttaaacttg ggctgggagc cagcactgtt ttatgacctg aataaactgt tttactctca    780

tgcatgtact tgttgaagag tgagatttca tatctaccac cctcacgggt gtcggagagg    840

acagcccagc agtcaaattt gcagcgcttt cataacttgc accctgtgca gccatgtgag    900

agcacgcgag aaaatacact ctatacagag aagaggattt ctgaatgata tcaaggtgtc    960

agcataaaca cacatggatc aataagaact tcacaatgat atttattgtc aca          1013


<210> SEQ ID NO 47
<211> LENGTH: 33
<212> TYPE: DNA
<213> ORGANISM: artificial
<220> FEATURE:
<223> OTHER INFORMATION: oligonucleotide primer

<400> SEQUENCE: 47

cgtgaaggtg agccagtgag ttgattgcag tcc                                  33


<210> SEQ ID NO 48
<211> LENGTH: 31
<212> TYPE: DNA
<213> ORGANISM: artificial
<220> FEATURE:
<223> OTHER INFORMATION: oligonucleotide primer

<400> SEQUENCE: 48

cgtgccgatc aagtcaaaag cctccggtcg g                                    31


<210> SEQ ID NO 49
<211> LENGTH: 21
<212> TYPE: DNA
<213> ORGANISM: artificial
<220> FEATURE:
<223> OTHER INFORMATION: oligonucleotide primer

<400> SEQUENCE: 49

cagtccagtt acgctggagt c                                               21
```